US012770725B2

(12) United States Patent
Mousseau et al.

(10) Patent No.: US 12,770,725 B2
(45) **Date of Patent: *Oct. 20, 2026**

(54) SYSTEMS, DEVICES AND METHODS FOR SECURING AND TRACKING DRUG DISPENSING DEVICES

(71) Applicant: 3D BRIDGE SOLUTIONS INC., Vancouver (CA)

(72) Inventors: Gary Mousseau, Waterloo (CA); Karima Bawa, Vancouver (CA); Jason Tyler Griffin, Kitchener (CA)

(73) Assignee: 3D Bridge Solutions Inc., Vancouver (CA)

( * ) Notice: Subject to any disclaimer, the term of this patent is extended or adjusted under 35 U.S.C. 154(b) by 154 days.

This patent is subject to a terminal disclaimer.

(21) Appl. No.: 18/900,047

(22) Filed: Sep. 27, 2024

(65) Prior Publication Data

US 2025/0022567 A1 Jan. 16, 2025

Related U.S. Application Data

(63) Continuation of application No. 18/315,215, filed on May 10, 2023, now Pat. No. 12,131,812, which is a continuation of application No. 17/674,715, filed on Feb. 17, 2022, now Pat. No. 11,688,499, which is a continuation of application No. 17/090,748, filed on Nov. 5, 2020, now Pat. No. 11,289,182.

(60) Provisional application No. 63/062,359, filed on Aug. 6, 2020, provisional application No. 62/930,876, filed on Nov. 5, 2019.

(51) Int. Cl.

| | |
|---|---|
| ***G16H 20/13*** | (2018.01) |
| ***A61J 7/04*** | (2006.01) |
| ***G06F 21/62*** | (2013.01) |

(52) U.S. Cl.

CPC ............ *G16H 20/13* (2018.01); *A61J 7/0427* (2015.05); *G06F 21/6245* (2013.01)

(58) Field of Classification Search

CPC ..... G16H 20/13; G06F 21/6245; A61J 7/0427

See application file for complete search history.

(56) References Cited

U.S. PATENT DOCUMENTS

| | | | | |
|---|---|---|---|---|
| 6,068,156 | A | 5/2000 | Liff et al. | |
| 9,731,853 | B2 | 8/2017 | Akdogan et al. | |
| 9,798,859 | B2 | 10/2017 | Yodfat et al. | |
| 10,231,077 | B2 | 3/2019 | Raduchel et al. | |
| 11,289,182 | B2 * | 3/2022 | Mousseau | G16H 40/67 |
| 11,688,499 | B2 * | 6/2023 | Mousseau | G06F 21/606 700/231 |
| 12,131,812 | B2 * | 10/2024 | Mousseau | G06F 21/44 |

(Continued)

*Primary Examiner* — Michael Collins

(74) *Attorney, Agent, or Firm* — Norton Rose Fulbright Canada LLP; Maya Medeiros

(57) ABSTRACT

Systems and methods for controlling and tracking computer devices using a secure communication path between a central database and a device control-file watchdog program. One or more device control-files can be generated to control, limit and track a computer device using a device control-file watchdog program. The system sets limits on the computer device to ensure the user operating the computer device stays within a restricted set of usage limitations. The device control-file watchdog program protects the one or more device control-files and additionally can report on all activities performed by the computer device to the central database.

20 Claims, 14 Drawing Sheets

(56) References Cited

U.S. PATENT DOCUMENTS

| | | | |
|---|---|---|---|
| 2002/0070226 | A1 | 6/2002 | Liff et al. |
| 2003/0055406 | A1 | 3/2003 | Lebel et al. |
| 2005/0240305 | A1 | 10/2005 | Bogash et al. |
| 2007/0185615 | A1 | 8/2007 | Bossi et al. |
| 2014/0324216 | A1 | 10/2014 | Beg et al. |
| 2017/0173262 | A1 | 6/2017 | Veltz |

* cited by examiner

SYSTEMS, DEVICES AND METHODS FOR SECURING AND TRACKING DRUG DISPENSING DEVICES

CROSS-REFERENCE TO RELATED APPLICATIONS

The application is a continuation of U.S. application Ser. No. 18/315,215 filed May 10, 2023 which is a continuation of U.S. Pat. No. 11,688,499 issued on Jun. 27, 2023 which is a continuation of U.S. Pat. No. 11,289,182 issued on Mar. 29, 2022 which claims the benefit of and priority to U.S. Provisional Application No. 62/930,876 filed Nov. 5, 2019 and U.S. Provisional Application No. 63/062,359 filed Aug. 6, 2020 the contents of which are hereby incorporated herein by reference.

FIELD

Embodiments relate to the creation of a secure closed-loop system for the distribution and usage of prescription drugs with protection of the computer files encoding prescriptions, including dosage requirements and the monitoring of drug consumption described in the files. The embodiments further relate to control of access to dispensing devices containing drugs and the subsequent tracking of the daily usage.

INTRODUCTION

There is a need for control of the use of drugs or supplements. There is a need for the control of use of potentially addictive drugs by people who are addicts or people who may be susceptible to becoming addicted. This is an example and there is a need to control the delivery of other types of drugs. A person may not want to ingest a drug or may want to ingest too much of the drug. For example, people who are addicted to drugs are often required to attend a pharmacy or other medical facility (usually on a daily basis) to receive their prescription and to consume it under the supervision of the pharmacist or other health care professional. This exercise is expensive and cumbersome and puts unnecessary strain on the health care system.

People can engage in double-doctoring and/or can try to have their prescriptions filled at multiple pharmacies. These problems extend beyond opioids into sleeping pills, Ritalin™, Concerta™, benzodiazepines, barbiturates, cannabinoids, anabolic steroids and psychostimulants, other stimulant type medications and any other drug that might be highly sought after. There is a need for better tracking of drug distribution and usage, such as for potentially addictive drugs, for example.

There is also need for a system that can generate tracking data for drug compliance reports. Whether they are taking a solid pill, receiving insulin from a pump or receiving an inhaled medication, they often need help and guidance to stay on top of their drug consumption times and frequency. In some cases missing a drug dose can be fatal and will kill some patients.

Systems might have limited security for loading and dispensing drugs. They attempt to restrict access of the user after they have left the pharmacy with drugs in hand. They also allow the patient to control dispensing and set up their own access methods. Additionally, systems might not ensure that communications and files are secure and encrypted between the patient and the tracking system, which can leave the patient and dosage information exposed and vulnerable.

SUMMARY

Embodiments described herein relate to a method of creating, modifying and tracking a dosage rule file between a database and a drug watchdog program running on a dispensing device.

Embodiments described herein relate to a computer implemented method of securing and tracking a dispensing device and a dosage rule file using a central server and a drug watchdog program running on the dispensing device. The method can involve at a central server having a hardware processor with an interface and a non-transitory memory storing a database, authorizing a login using the hardware processor to match credentials of the user against a database of authorized users stored in the non-transitory memory and receiving dispensing device identification for the dispensing device for storage in the non-transitory memory; generating a dosage rule file by receiving input data at the interface from the authorized user and encoding at least drug consumption information, identification of the drug consumer, and additional authorized users into machine readable instructions for a drug watchdog program; identifying a destination dispensing device to receive the dosage rule file using the hardware processor to access the dispensing device identification in the non-transitory memory; establishing a secure communication link to encrypt messages exchanged with the dispensing device with encryption keys to confirm the identification information of the dispensing device; transmitting, using the secure link, the dosage rule file to the destination dispensing device; at the destination dispensing device having a hardware processor and a non-transitory memory storing the drug watchdog program and the dosage rule file, executing the dosage rule file and the drug watchdog program using the hardware processor to access the non-transitory memory, and upon execution, the drug watchdog program continuously running on the destination dispensing device and reading the dosage rule file to: open a compartment of dispensing equipment to receive drugs matching the drug consumption information in the dosage rule file; detect closure of the compartment and drug provisioning of the dispensing device; upon authorizing bio-identity input, send a provisioned stage reached message to the central server to program the processor to a provisioned stage; receive a begin deployment command from the central database to program the processor to a deployment stage of the dispensing device; activate timers upon deployment on the dispensing device to control release of the drugs contained in the compartment for the drug consumer; and encrypt messages using the encryption keys; and send the encrypted drug consumption messages for decryption by all authorized users to the central database upon expiration of at least one of the timers.

In some embodiments, the method involves at the central server, providing the interface to receive the input from the authorized user to generate the completed dosage rule file.

In some embodiments, the method involves detecting a connection from a selected dispensing device to a user's computer system; providing, to the authorized drug dispenser, the interface on the central server in order to generate the completed dosage rule file; upon detecting the finishing of the completed dosage rule file, using the selected dispensing device's identification received from the dispensing device through its connection to the user's computer, to establish the secure channel to encrypt all messages exchanged between the dispensing device and the central server; and transmitting the completed dosage rule file to enable the provisioning of the dispensing device.

In some embodiments, the method involves at the destination device running the drug watchdog program, establishing a secure data communication path with the central server by using the dispensing device's identification to select encryption keys; and receiving an indication from the central server over the secure data communication path that the dosage rule file is ready for transmission to the destination dispensing device, the completed dosage rule file encrypted using encryption keys linked to the dispensing device identification.

In some embodiments, the method involves, at the destination dispensing device, establishing a secure communication link between the compartment and the hardware processor for data exchange, opening the compartment by sending control messages to the compartment of the dispensing device over the secure communication link, wherein the compartment of the dispensing device is separate from the hardware processor of the dispensing device.

In some embodiments, the method involves identifying the destination dispensing device as having dispensing equipment separate from the hardware processor of the dispensing device running the drug watchdog program, the dispensing equipment comprising the compartment, and encoding an identifier for the drug dispensing equipment in the dosage rule file.

In some embodiments, the opening of the compartment requires a confirming status message from the central server to instruct the drug watchdog to perform an unlock procedure.

In some embodiments, the method involves, at the central server, allowing multiple dispensing devices to be in a provisioned stage, and sending a begin deployment command to only one dispensing device assigned to the same drug consumer at a time.

In some embodiments, the method involves, at the central server, detecting that a deployed dispensing device has run out of drugs and sending a begin deployment command to the next provisioned dispensing device for the same drug consumer.

Embodiments described herein relate to a computer implemented method of securing and tracking a dispensing device and a dosage rule file by an authorized drug dispenser using one or more central servers for managing dispensing devices and a drug watchdog program running on the dispensing device. The method involves: at a hardware processor coupled to a non-transitory memory storing a prescription database of authorized users, authorizing a login using the hardware processor matching the credentials of the user against the prescription database of authorized users stored in the non-transitory memory to create an authorized drug dispenser; searching by the authorized drug dispenser for prescription information using the hardware processor to access the prescription database stored in the non-transitory memory, the authorized drug dispenser linked to a drug consumer's identity; creating a dosage rule file encoding the prescription information, the drug consumer's identity, drug consumption information and additional authorized users for the dispensing device into machine readable instructions for the drug watchdog program that can be downloaded to the dispensing device; establishing a secure data communication path with the central server used for managing dispensing devices, by using the hardware processor to determine identification of the dispensing device to select encryption keys; encrypting the dosage rule file using encryption keys linked to the dispensing device identification; exchanging with the central server over the secure communication path the dosage rule file; at the dispensing device having a hardware processor and a non-transitory memory storing the drug watchdog program and the dosage rule file, executing the dosage rule file and the drug watchdog program using the hardware processor to access the non-transitory memory, and upon execution, the drug watchdog program continuously running on the dispensing device and reading the dosage rule file to: open a compartment of dispensing equipment to allow drugs to be inserted matching the drug consumption information in the dosage rule file; detect closure of the compartment and drug provisioning of the dispensing device; upon authorizing bio-identity input from the drug consumer, sending a confirmation message to the central server to enter a provisioned stage; receive a begin deployment command from the central server that commences the deployment stage; activate timers upon deployment on the dispensing device to allow the controlled release of the drugs contained in the compartment; and send drug consumption messages and alert messages for decryption by all authorized users, using the selected encryption keys to the central database when the timer expires.

In some embodiments, creating the dosage rule file involves moving the prescription information from the prescription database to the central server that is used for managing dispensing devices.

In some embodiments, opening of the compartment requires a confirming status message from the central server informing the drug watchdog to perform an unlock procedure.

In some embodiments, the expiration of the activated drug dose timers to allow the release of a drug dose, also includes one or more indications including modifying the display of LED lights, displaying a message on a screen, the playing of auditory sounds and the sending one or more message to the drug consumer using a configured communication method.

In some embodiments, an alert message transmitted from the dispensing device to the central server is relayed from the central server to the drug consumer using one or more configured communication methods.

In some embodiments, an alert message within the dispensing device is sent directly to the drug consumer's computer device using one or more configured communication methods.

In some embodiments, the decryption of messages by all authorized users further includes the ability for one of the authorized users to modify the dosage rule file.

In some embodiments, the method involves, at the destination dispensing device, establishing a secure communication link between the compartment and the hardware processor for data exchange, opening the compartment by sending control messages to the compartment of the dispensing device over the secure communication link, wherein the compartment of the dispensing device is separate from the hardware processor of the dispensing device.

In some embodiments, the method involves identifying the destination dispensing device as having drug dispensing equipment separate from the hardware processor of the dispensing device running the drug watchdog program, the drug dispensing equipment comprising the compartment, and encoding an identifier for the drug dispensing equipment in the dosage rule file.

Embodiments described herein relate to a computer system for securing and tracking a dispensing device and a dosage rule file. The system can involve a central server having a hardware processor with an interface and a non-transitory memory storing a database, the interface to generate and provide a completed dosage rule file encoding at least a drug consumer's identity, drug consumption information and authorized users for a dispensing device into machine readable instructions for the drug watchdog program, the completed dosage rule file encrypted using encryption keys linked to the dispensing device identification; a dispensing device having a hardware processor and a non-transitory memory storing drug watchdog program running on the dispensing device, the hardware processor executing the drug watchdog program and upon execution, the drug watchdog program continuously running on the destination dispensing device to: establish a secure data communication path with the central server by using the dispensing device's identification to create an encrypted channel; verify that at least one authorized user is in possession of the identified dispensing device by changing the state of the dispensing device and requiring the authorized user to verify that state; receive an indication from the central server within the received status message over the secure communication path that the completed dosage rule file is ready for download after the authorized user is verified; exchange the completed dosage rule file with the central server to enable the provisioning of the dispensing device; wherein the hardware processor executes the completed dosage rule file and upon execution, the drug watchdog program reading the dosage rule file to: open a compartment of dispensing equipment to allow drugs to be inserted matching the drug consumption information in the dosage rule file; detect closure of the compartment and drug provisioning of the dispensing device; upon authorizing a biometric input from a drug consumer, sending a confirmation message to the central server to enter a provisioned stage of the dispensing device; receive a begin deployment command from the central server that commences the deployment stage of the dispensing device; and activate timers upon deployment on the dispensing device to allow the controlled release of the drugs contained in the compartment; and send drug consumption messages for viewing by all authorized users, using the selected encryption keys to the central server when the timer expires.

In some embodiments, the destination dispensing device establishes a secure communication link between the dispensing equipment and the hardware processor for data exchange to open the compartment by sending control messages, wherein the dispensing equipment is separate from the hardware processor running the watch dog program.

Embodiments described herein relate to a method of creating, modifying and tracking a dosage rule file between a database and a drug watchdog program running on a dispensing device.

Embodiments described herein can provide a method that can involve, at a central database, authorizing a login by matching the credentials of the user against a database of authorized users. The method involves allowing the authorized user to modify or create the dosage rule file, the dosage rule file linked to at least the identification of a drug consumer, the dosage rule file encoding at least drug consumption information, the drug consumer's identity, and additional authorized users for this dispensing device. The method involves identifying a destination dispensing device to receive the dosage rule file through dispensing device identification information linked to credentials provided by the authorized login. The method involves encrypting messages exchanged with the dispensing device with encryption keys linked to the identification information of the dispensing device. The method involves downloading, using the encryption keys, the dosage rule file to enable provisioning of the dispensing device, wherein the dosage rule file configures the drug watchdog program to: open a compartment of the dispensing device to allow drugs to be inserted matching the drug consumption information in the dosage rule file; detect the closure of the compartment to indicate provisioning of the dispensing device; activate timers upon provisioning on the dispensing device to allow for controlled release of the drugs contained in the compartment; and send drug consumption messages for viewing by all authorized users, the messages encrypted using the encryption keys, to the central database when at least one of the timers expires.

In an aspect, embodiments described herein relate to a method of creating, modifying and tracking a dosage rule file between a central database and a drug watchdog program running on a dispensing device. The method, involves, at a central database authorizing a login by matching the credentials of user against a database of authorized users.

The method involves allowing the authorized user to generate a dosage rule file encoding at least the drug consumer's identity, drug consumption information and additional authorized users for this dispensing device. The method involves identifying a destination dispensing device to receive the dosage rule file through the reception of dispensing device identification linked to the credentials provided by the authorized login.

The method involves encrypting messages exchanged with the dispensing device using encryption keys linked to the identification information of the dispensing device. The method involves downloading, using the encryption keys, the dosage rule file to enable provisioning of the dispensing device, wherein the dosage rule file configures the drug watchdog program to: open a compartment of the dispensing device to allow drugs to be inserted matching the drug consumption information in the dosage rule file; detect the closure of the compartment to indicate provisioning of the dispensing device; activate timers upon provisioning on the dispensing device to allow the controlled release of the drugs contained in the compartment; and send drug consumption messages for viewing by all authorized users, using the encryption keys, to the central database, when at least one of the timers expires.

In an aspect, embodiments described herein relate to a method of creating, modifying and tracking a dosage rule file between a central database and a drug watchdog program running on a dispensing device. The method involves, at a central database, creating an authorized user by verifying a dispensing device coupled to the user's computer and permitting a login; permitting the authorized user to generate a completed dosage rule file containing at least the drug consumer's identity, drug consumption information and additional authorized users for this dispensing device; identifying a destination dispensing device to receive the completed dosage rule file through the reception of dispensing device identification provided by the authorized login; using the identification information of the dispensing device to select encryption keys to be used to encrypt messages exchanged with the dispensing device; downloading, using the selected encryption keys, the dosage rule file to enable the provisioning the dispensing device. The dosage rule file configures the drug watchdog program to: open a compartment of the dispensing device to allow drugs to be inserted matching the drug consumption information in the dosage rule file; detect the closure of the compartment to indicate provisioning of the dispensing device; activate timers upon provisioning on the dispensing device to allow the controlled release of the drugs contained in the compartment; and send drug consumption messages for viewing by all authorized users, using the selected encryption keys, to the central database when the timer expires.

The method can involve creating, modifying and tracking a dosage rule file between a central database and a drug watchdog program running on a dispensing device. The method can involve, at a drug watchdog program, detecting a connection from a selected dispensing device to a user's computer system. The method can involve permitting a login by the user to create an authorized drug dispenser. The method can involve allowing the authorized drug dispenser to use an interface provided through the connection to generate a completed dosage rule file, containing at least the drug consumer's identity, drug consumption information and additional authorized users for this dispensing device, on the connected dispensing device. The method can involve initiating a separate connection to the central database when the authorized drug dispenser has finished the completed dosage file. The method can involve using the separate connection to provide the selected dispensing device's identification in order to select encryption keys to be used to encrypt messages exchanged between the dispensing device and the central database. The method can involve exchanging the completed dosage rule file with the central database to enable the final provisioning of the dispensing device. The dosage rule file configures the drug watchdog program to: open a compartment of the dispensing device to allow drugs to be inserted matching the drug consumption information in the dosage rule file; detect the closure of the compartment to indicate provisioning of the dispensing device; activate timers upon provisioning on the dispensing device to allow the controlled release of the drugs contained in the compartment; and send drug consumption messages for viewing by all authorized users, using the selected encryption keys to the central database when the identified user confirms the removal of drugs when the timer expires.

The method can involve creating, modifying and tracking a dosage rule file between a central database and a drug watchdog program running on a dispensing device. The method involves, at a drug watchdog program, detecting a connection from a selected dispensing device to a user's computer system. The method can involve allowing the user to become an authorized drug dispenser, by accepting a login at a central database when it confirms the identification information of the connected dispensing device. The method can involve providing, to the authorized drug dispenser, an interface on the central computer in order to generate a completed dosage rule file containing at least the drug consumer's identity, drug consumption information and additional authorized users for this dispensing device. The method can involve detecting the finishing of the completed dosage rule file and using the selected dispensing device's identification received from the dispensing device through its connection to the user's computer, to select encryption keys to be used to encrypt all messages exchanged between the dispensing device and the central database. The method can involve exchanging the completed dosage rule file with the central database to enable the final provisioning of the dispensing device. The dosage rule file configures the drug watchdog program to: open a compartment of the dispensing device to allow drugs to be inserted matching the drug consumption information in the dosage rule file; detect the closure of the compartment to indicate provisioning of the dispensing device; activate timers upon provisioning on the dispensing device to allow the controlled release of the drugs contained in the compartment; and send drug consumption messages for viewing by all authorized users, using the selected encryption keys to the central database when the timer expires.

In another aspect, embodiments described herein provide a method of creating, modifying and tracking a dosage rule file between a central database and a drug watchdog program running on a dispensing device. The method can involve, at a drug watchdog program, establishing a secure cellular data communication path with a central database by using the dispensing device's identification to select encryption keys. The method can involve sending secure periodic polling messages to a central database using the confirmed encryption keys to update the dispensing device's status. The method can involve receiving an indication from the central database within the received status message that a completed dosage rule file, containing at least the drug consumer's identity, drug consumption information and additional authorized users for this dispensing device, is ready for download. The method can involve exchanging the completed dosage rule file with the central database to enable the provisioning of the dispensing device. The dosage rule file configures the drug watchdog program to: open a compartment of the dispensing device to allow drugs to be inserted matching the drug consumption information in the dosage rule file. The drug watchdog then detect the closure of the compartment to indicate the next step in provisioning of the dispensing device can take place; activate timers upon provisioning on the dispensing device to allow the controlled release of the drugs contained in the compartment; and send drug consumption messages for viewing by all authorized users, using the selected encryption keys to the central database when the timer expires.

Embodiments relate to the creation of a secure closed-loop system for the distribution and usage of prescription drugs. The embodiments include the protection of the computer files that encode instructions defining a prescription, including dosage requirements and the monitoring of drug consumption described in the files. The embodiments further include the control of assigning drugs to a patient, overall access to those drugs and the subsequent tracking of the usage.

In an aspect, there is provided a method of controlling and tracking a dosage rule file between a central database and a drug watchdog program running on a dispensing device. The method involves, at a central database, authorizing a login by verifying user login data using one or more authentication means; creating a dosage rule file containing at least drug consumption information and additional authorized users for this dispensing device; displaying tracking information from the dispensing device for the additional authorized users; initiating a secure link between the central database and the drug watchdog program by creating and using a shared encryption key; downloading over the secure link the dosage rule file and other messages related to operation of the dispensing device, wherein the dosage rule file configures the drug watchdog program to: open a main compartment of the dispensing device using an unlock mechanism to allow drugs to be inserted into the main compartment; detect the closure of the main compartment using the locking mechanism and allowing a controlled release of the drugs contained in the main compartment; and send feedback messages to the central database of activities detected on the dispensing device.

In another aspect, there is provided a method of controlling and tracking a dosage rule file between a central database and a drug watchdog program running on a dispensing device. The method involves, at a drug watchdog program, detecting a connection to a drug dispenser's computer; verifying a login by a drug dispenser's to permit access to the dispensing device; using an interface to generate a dosage rule file; initiating a secure link between the drug watchdog program and the central database by creating and using a shared encryption key; uploading to the central database over the secure link the dosage rule file and other messages related to operation of the dispensing device, wherein the dosage rule file configures the drug watchdog program to: open a main compartment of the dispensing device using an unlock mechanism to allow drugs to be inserted into the main compartment; detect the closure of the main compartment through a locking mechanism and allowing the controlled release of the drugs contained in the main compartment using an ejection mechanism; and send feedback messages to the central database of activities detected on the dispensing device.

In some embodiments, the authenticating means is a connection to an authenticated dispensing device.

In some embodiments, the authenticating means matches login information to data received from one or more governing body of professionals and government organizations.

In some embodiments, the drug consumption information includes the number of drugs to be inserted into the dispensing device.

In some embodiments, an additional authorized user can also have the dosage rule file updated and downloaded to the dispensing device.

In another aspect, there is provided a method of controlling and tracking a dispensing device for delivery of prescription drugs for a drug consumer using a dosage rule file for configuring a drug watchdog program to control the dispensing device. The method involves generating a login procedure to establish an authorized drug prescriber and an authorized drug dispenser by matching credentials for authorized drug prescriber and the authorized drug dispenser to data encoding drug prescribers and drug dispensers; generating the dosage rule file for the drug consumer containing at least drug consumption information based on input from an authorized drug prescriber and identification information received from a drug consumer; receiving a request from an authorized drug dispenser to match a drug consumer's identification information to the identification information in the dosage rule file; authenticating at a central database an attached dispensing device with one or more messages exchanged with a drug watchdog program running within the dispensing device; downloading, using one or more of the messages, the dosage rule file to the dispensing device for use by the drug watchdog program, wherein the dosage rule file configures the drug watchdog program to: block all attempts by other programs running on the dispensing device to perform file commands on the dosage rule file; use the drug consumption information within the dosage rule file to time the release of drugs contained within the dispensing device through a drug ejector; and provide feedback messages of all activities that take place at the dispensing device to the central database.

In some embodiments, the authorized drug prescriber and the authorized drug dispenser use a biometric input as part of creating a login procedure at the central database.

In some embodiments, taking identification includes using biometric information from the drug consumer.

In some embodiments, the drug dispenser matches the drug consumer's information by taking biometric information from them.

In some embodiments, the authenticating of the dispensing device takes place by sending a manufactured serial number when exchanging one or more messages.

In some embodiments, the authenticating of the dispensing device takes place using public and private encryption keys that were pre-loaded during the manufacturing process.

In some embodiments, the authenticating of the dispensing device also requires a physical connection to a computer within the drug dispenser's location.

In some embodiments, the authenticated dispensing device also requires the creation of a separate encryption key that is used for all data exchanges with the central database.

In some embodiments, the authenticating of an attached dispensing device can also include the ability to detect the type and number of drugs within the drug dispensing device to ensure ample supply is present for the next dose.

In some embodiments, the authenticating of an attached dispensing device can also include the ability to detect that there should be ample drugs still available inside the device and refusing to allow more drugs to be added.

In some embodiments, the feedback can also include detection of unauthorized activity upon the file or damage to the file to allow for re-acquisition of the file if needed.

In some embodiments, the feedback can also include detection of unauthorized attempts to access the contents of the dispensing device.

In some embodiments, the restricting of access on the prescription file also includes the ability to update the dosage rule file should an authorized change be needed to the original dosage rule file.

In some embodiments, the feedback also includes providing GPS location information when a change is detected.

In some embodiments, the feedback also includes detecting a missed dosage and sending GPS coordinates.

In some embodiments, the feedback also includes photographic information taken each time a single dose of drugs are ejected for the drug consumer.

In some embodiments, the feedback also includes ingestion information when a signal is received based on ingestion of the drug dosage within the stomach of a drug consumer.

In some embodiments, the ingestion information comes from a device that is worn on the body of the drug consumer.

In some embodiments, the signal is generated by two or more compounds that when mixed with stomach acids generate a detectable signal from within the drug consumer's stomach.

In some embodiments, the one or more messages and feedback message are transmitted over a cellular network.

In some embodiments, the one or more messages and feedback messages are transmitted using a WiFi communication method.

In some embodiments, the one or more messages and feedback messages are transmitted using a Bluetooth communication method.

In some embodiments, the one or more messages and feedback messages are transmitted using a USB connection.

In another aspect, there is provided a method of using a dosage rule file to configure a drug watchdog program on a drug dispensing device and a central database to track and control the use of prescription drugs. The method involves authorizing a drug prescriber and a drug dispenser at a central database through a secure login procedure; permitting the authorized drug prescriber to create a dosage rule file containing drug consumption requirements on the central database; requiring an authorized drug prescriber to acquire an identity for a drug consumer and associating the identity to the dosage rule file within the central database; permitting an authorized drug dispenser to search for the dosage rule file with the identity provided by the drug consumer; sending search match results from the central database to an authorized drug dispenser confirming that the dosage rule file was located for the drug consumer; opening a data communications connection between the dispensing device and the central database; securely downloading the authorized dosage rule file into the dispensing device using one or more messages; allowing the authorized drug dispenser to access a drug containment area within the dispensing device to receive the prescribed drugs; and using the drug consumption information within the authorized dosage rule file to guide the dispensing device in permitting drugs to be dispensed for the matching drug consumer.

In another aspect, there is provided a method of using a drug watchdog program working within a dispensing device to control and regulate the use of prescription drugs. The method involves, within the dispensing device, detecting a connection to a computer system that is located within a drug dispenser's facility; opening a connection to a central database to establish an encryption key for creating a secure communication path; receiving confirmation over the secure connection path that an authorized dosage rule file containing operating parameters will be downloaded for use by the drug watchdog program; permitting access to a main containment area to allow the drug dispenser to place a quantity of drugs to be consumed; detecting the closing of the main containment area and locking the main containment area to stop any further access to the main containment area; using the operating parameters within the authorized dosage rule file by the drug watchdog program to control the dispensing device, wherein the dosage rule file configures the drug watchdog program to: stop all file access attempts by other programs on the authorized dosage rule file; use the operating parameters within the authorized dosage rule file to time the release of drugs contained within the dispensing device; send secure messages to a central database regarding all activities that are detected by dispensing device. The dosage rule file can encode the operating parameters as machine readable instructions for the drug watchdog software. The operating parameters can relate to the dispensing device and related dispensing equipment. The dosage rule file can encode the operating parameters so that the drug watchdog software can read the dosage rule file to control the dispensing device and related dispensing equipment using the encoded operating parameters.

In another aspect, there is provided a method of controlling and tracking a dispensing device for delivery of prescription drugs by an authorized drug dispenser using a dispensing device. The method involves connecting a dispensing device to a drug dispenser's computer; establishing an authorized drug dispenser by exchanging credentials with the dispensing device to create an authorizing login procedure; generating, by the authorized drug dispenser, a dosage rule file for a drug consumer containing at least drug consumption information and the quantity of drugs to be placed into the dispensing device based on information provided by the drug prescriber; receiving identification information from the drug consumer by the authorized drug dispenser to include within the dosage rule file; inserting drugs matching the amount of drugs indicated in the dosage rule file into main compartment of the dispensing device; provisioning the dispensing device by securely downloading the dosage rule file by the authorized drug dispenser to a drug watchdog program running on the dispensing device and closing the main compartment to a locked position; wherein the dosage rule file configures the drug watchdog program to: only open the main compartment by an authorized drug dispenser performing the authorizing login procedure; use the drug consumption information within the dosage rule file to time the release of drugs contained within the dispensing device; detect any attempts to break into the dispensing device and report messages on the detection to a central database, and provide feedback messages of all activities that take place at the dispensing device to the central database.

In some embodiments, taking identification from the drug consumer includes using biometric information from the drug consumer.

In some embodiments, the dosage rule file also contains or encodes biometric information from the drug consumer.

In some embodiments, the time release of drugs also requires a biometric input from the drug consumer.

In some embodiments, a failsafe procedure is provided to the drug consumer to release one or more additional dosages of drugs should a failure be detected when attempting to dispense a drug at the appointed time release period.

In another aspect, there is provided a method of using a drug watchdog program working within a dispensing device to control and track the use of drugs. The method involves, at a dispensing device, detecting an authorized connection to a computer system using one or more approved connection methods; authorizing access over the approved connection to a drug dispenser using their credentials to create an authorizing login procedure; permitting access to a main containment area to allow the authorized drug dispenser to place a quantity of drugs to be consumed; accepting the download of a dosage rule file that contains at least the timed dosage requirements and the amount of drugs to be placed within the main containment area; detecting the closing of the main containment area and locking it to stop any further access; using the operating parameters within the dosage rule file by the drug watchdog program to guide the daily operation, wherein the dosage rule file configures the drug watchdog program to: stop all file access attempts by other programs on the dosage rule file; use the operating parameters within the authorized dosage rule file to time the release of drugs contained within the dispensing device; send secure messages to a central database regarding all activities that are detected, and only open the main compartment when the authorizing login procedure is successfully executed.

In some embodiments, the taking identification from the drug consumer includes using biometric information from the drug consumer.

In some embodiments, the dosage rule file also contains biometric information from the drug consumer.

In some embodiments, the time release of drugs also requires a biometric input from the drug consumer.

In some embodiments, a failsafe procedure is provided to the drug consumer to release one or more additional dosages of drugs should a failure be detected when attempting to dispense a drug at the appointed time release period.

BRIEF DESCRIPTION OF DRAWINGS

The following detailed description of the invention is better understood when read in conjunction with the included figures. The included figures are intended to illustrate one implementation of the invention for one skilled in the art. These exemplary illustrations are not intended to limit the disclosure to the specific embodiments shown herein.

DETAILED DESCRIPTION OF DRAWINGS

Figure 1:
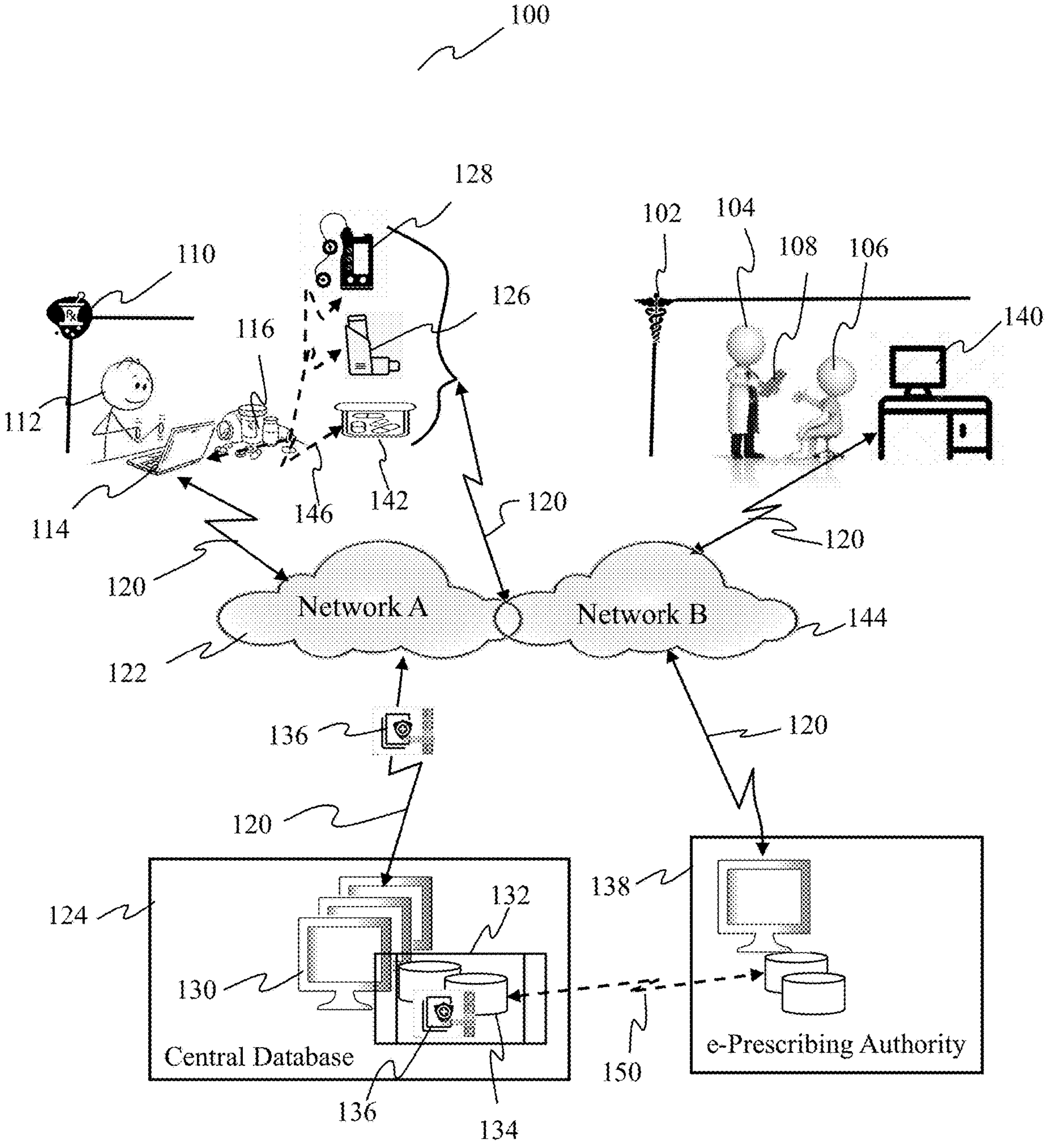
FIG. 1 is an illustration of a network overview showing drug prescribers and drug dispensers.

Embodiments described herein provide a system and method for tracking and controlling devices and operations involved in the processes of prescribing drugs and the distribution and consumption of those drugs is provided.

Embodiments further describe the feedback of information to multiple connected systems to communicate accurate information about the distribution and use of any drug that needs this advanced tracking system. The embodiments described can support clinical drug trials when tracking and control of new drugs is necessary, for example. The embodiments can support the senior citizen population where several health issues can cause problems with taking medications consistently and safely, as another example. The embodiments can be used for different drugs, supplements, and other controlled substances. Patients might forget if they have already taken their medications or might overdue their medications on purpose.

Several embodiments are possible when using the system to control a wide-range of medical devices. The system has a central server with one or more hardware processors and non-transitory memory storing central databases. There can be a secure connection between the central database and the one or more processors of the central server, and the drug watchdog program. This system also allows for feedback and reporting of all trackable events on the drugs being consumed from those devices.

Medical devices can have several embodiments and can be built using many potential methods. They might dispense a wide range of physical pills, liquid compounds and vapour compounds. In some embodiments they are a single physical device with all communications equipment, control firmware and dispensing equipment. The dispensing equipment can be drug dispensing equipment, such as a compartment or container for drugs. The dispensing device can integrate dispensing equipment. The dispensing device can be separate from the dispensing equipment and have a secure communication path with the dispensing equipment for data exchange and control commands to actuate the dispensing equipment, for example. The dispensing device and dispensing equipment can involve multiple components connected by secure communication paths or channels for message exchange. The dispensing device can be referred to as a controllable medical device with dispensing equipment that can be controlled or actuated by control commands or messages. In other embodiments one or more systems (e.g. computer hardware processors and non-transitory memory storing instructions) make up the controllable medical device. In this application the term "dispensing device" can be used to identify the one or more computers that make up all needed functional elements of the secure, controllable and monitorable dispensing of drugs.

The dispensing device can have a hardware processor that executes and runs the watchdog software stored in non-transitory memory. The dispensing device (having drug watchdog software stored in non-transitory memory) can be associated with dispensing equipment for the drugs. The dispensing equipment can include a compartment for drugs that can be controlled and monitored by the dispensing device using the drug watchdog software and dosage rule file. The dispensing device can integrate the dispensing equipment, for example, and can have an internal communication system for exchange data or messages. The dispensing device (having drug watchdog software stored in non-transitory memory) can be separate from the dispensing equipment (e.g. compartment for the drugs) and in communication over a secure channel to exchange data and control commands. The dispensing device can send commands to the dispensing equipment to actuate components, for example. The dispensing device and the dispensing equipment can also communicate with other components to exchange commands and actuate components of the dispensing equipment. The dispensing equipment can also be referred to as drug dispensing equipment or medical drug dispensing equipment.

The dispensing device can integrate or couple to a computing device with at least one hardware processor, non-transitory memory, and at least one I/O interface, and at least one network interface. The I/O interface can include software and hardware configured to facilitate communications with the processing unit hardware processor and/or communications to user devices, dispensing equipment, or the central server. The hardware can include display screen configured to visually display graphics, text and other data. The memory is configured to store information, including both data and instructions. The instructions which are stored at the memory generally include firmware and/or software for execution by the hardware processor. The memory can store the drug watchdog software and the dosage rule file. The memory can store the drug watchdog software for execution by the hardware processor. The drug watchdog software can read the dosage rule file in the memory.

The central server can run in a closed environment, like an institution or in a cloud environment. The central server runs and manages various databases and collectively these systems are called central database in this application. To highlight the system functions, there are several embodiments presented to illustrate example use cases for the creation of a closed-loop system for controlling devices and operations for delivery of drugs a specific drug consumer (e.g. drugs are prescribed for a drug consumer and only they can access those drugs). This closed-loop system (also referred to as a feedback control system) provides controls and feedback within the system to try to help eliminate errors and thwart attempts to steal or overuse the drugs that are prescribed. The central server couples to the central database. The central server can be referred to as the central database herein for data exchange with other components.

This specific embodiment of a drug monitoring system is built upon a relationship between a central database and a software program which can be referred to as the drug monitor watchdog program, "drug watchdog". The drug watchdog is a specific embodiment of the file watchdog. In some embodiments the drug watchdog runs within many kinds of medical dispensing devices that have specific dosing requirements and require real-time monitoring capabilities.

In other embodiments a direct and secure relationship exists between separate computer systems that allow the specific dosing requirements and real-time monitoring capabilities. Some examples of medical dispensing devices can include tamper-proof dispensing devices, digital insulin injection devices, advanced inhaler devices, intravenous (IV) machines, all referred to as "dispensing devices". The drug watchdog provides a safe distribution point for the prescribed drugs for a given drug consumer.

A dispensing device could be made up of one or more computer devices. In some embodiments the computer device is self-contained and contains the cellular hardware and drug watchdog firmware, the bio-identity components, and the medical dispensing equipment all in one physical housing.

The computer device can have at least one hardware processor, non-transitory memory, and at least one I/O interface, and at least one network interface. The I/O interface can include software and hardware configured to facilitate communications with the processing unit hardware processor and/or communications to related dispensing equipment, or the central server. The hardware can include a display screen configured to visually display graphics, text and other data. The non-transitory memory is configured to store information, including both data and instructions. The instructions which are stored at the memory generally include firmware and/or software for execution by the hardware processor. The memory can store the drug watchdog software and the dosage rule file. The memory can store the drug watchdog software for execution by the hardware processor. The drug watchdog software can read the dosage rule file in the memory.

In other embodiments the cellular hardware and drug watchdog might have the option of decoupling from the medical drug dispensing equipment. In these embodiments there is a secure and impenetrable relationship between the cellular hardware and drug watchdog to the medical drug dispensing equipment. This secure link might be encrypted Bluetooth link, a Near Field Communication (NFC) with a security handshake based on various encryption methods like agile encryption methods. In other embodiments the cellular hardware and drug watchdog are always separate and share a secure and impenetrable link for indicating that a drug can be dispensed once the patient is authenticated.

In those embodiments where the drug watchdog runs on a separate computer from the drug dispensing equipment various close communication methods like Bluetooth, RFID, Near Field RFID (also called NFC) and various 802.11 protocols (also called WiFi) methods could be employed to facilitate communications. Using one of these methods a secure channel can be easily created. In embodiments using NFC for example, one approach is to use NFC Secure Channel. Using a method like Diffie-Hellman is acceptable as NFC inherently does not allow the man-in-the-middle attack. With the symmetric key established, NFC Secure Channel can then be used for communications. In other embodiments using Bluetooth communications there are several security protocols to select from. These include L2CAP, RFCOMM in mode 2 and authentication and encryption services for mode 3. Bluetooth 5 also offers four different security levels where level 4 offers elliptic curve Diffie-Hellman, also known as P-256 which is FIPS (Federal Information Processing Standards) compliant.

The dispensing device acts as both the computer device needing to control the loading of drugs and the authorization to access the drugs contained within the medical drug dispenser. The relationship between the central database and the dispensing device is built upon identification information created for the dispensing device during manufacturing. The drug watchdog uses this identification information to help secure the relationship and exchanging information using this security. Once the dispensing device is provisioned and deployed, the drug watchdog becomes married to a drug consumer and a specific prescription dosage. In one embodiment, this relationship is established through the injection of encryption keys into tamper-proof memory. In another embodiment, this relationship is established through by providing the device a server-based electronic signature in non-volatile memory. In another embodiment the dispensing device generates a public and private encryption key pair and provides this to the server over a physical link, like a USB cable during the manufacturing process.

The drug watchdog is a computer program that might be a standalone program on a computer device, or it is running as just one application of many within an operating system (O/S). The programs goal is to safeguard the dosing and personal information of the drug consumer and to ensure the configuration information ("Dosage Rule File") is not damaged, stolen, hacked or deleted through nefarious means. The drug watchdog can employ several methods to ensure the inputs and messages it is sending to the central database are valid and secure. All communications are secure between the central database and the drug watchdog. Protection ensures the drug watchdog is not running on a cloned system, that is providing similar inputs and outputs to the real dispensing device and who is trying to use confusion and counterfeiting to invade the central database. There are several embodiments to solve this problem.

In one embodiment for example, the dispensing device would use a secure enclave methodology. The secure enclave is a protected environment on the dispensing device that is tamper-proof and where memory cannot be accessed directly. Only protected software running within the secure enclave can access the memory and perform actions with information provided. By locking a public and private encryption key pair into the secure enclave, an encryption method can be employed to ensure only the central database is able to decrypt the data and confirm it is from a known secure source. In this way the secure enclave offers an encryption service to the drug watchdog and it will encryption on its behalf even a small amount of data to ensure the authenticity of the environment. For example, the dispensing device's unique identifier could be signed (encrypted) using the private key of the dispensing device, protected in the secure enclave to valid the source of any given message by the central database.

In another embodiment an electronic signature is provided by the central database and is stored in non-volatile memory at the end of manufacturing. This signature can not be extracted or changed but can be read and provided to the drug watchdog every time it needs to send a secure message to the central database. The electronic signature could be unique for every dispensing device created. These two examples and others can provide an advanced level of confidence that the drug watchdog can verify that the information it is sending to the central database is secure, authorized and that the communication information has not been tampered with.

The process of programming the drug watchdog software is done using prescription information and configuration information to create a grouping of information called the dosage rule file in this application. Whether the drug watchdog is running within the same physical housing or a separate physical housing it always manages the dosage rule file and how it gets accessed. The dosage rule file is a collection of items that can be represented as a continuous file, a collection of parameters in a message or a collection of stored memory parameters in one or more memory locations. The dosage rule file is then managed through the central database by those individuals that have been given rights to access this information. Between the central database and the drug watchdog one or more secure identification measures are employed to ensure complete security and exchange of all information including the dosage rule file.

The overall operation of the system involves three main stages: the authentication stage, the provisioned stage, and the deployment stage. These stages can involve various embodiments. The first stage of authentication confirms the identity of the person wanting to provision and deploy a dispensing device. The provisioned stage is defined as all the steps necessary to reach the deployment stage. The deployment stage is defined as the active dispensing of medication in the dispensing device as instructed by the drug watchdog directly or using a secure relationship to the dispensing equipment.

Provisioning starts with building the dosage rule file and exchanging it between the central database and the drug watchdog. Provisioning continues once the dosage rule file is confirmed and the drug dispensing equipment can be opened for loading. In some embodiments this happens via comments directly from the drug watchdog software to the drug dispensing equipment. In other embodiments the drug watchdog will establish a secure connection to the drug dispensing equipment and issue an open main drug dispensing compartment command. Once opened, the drug dispenser will be allowed to load drugs matching the dosage rule file.

In some embodiments, matching can be confirmed using various pill scanning methods as the drugs are inserted into the dispensing device. For example, the pill itself might have a bar code, Q-code or some printed indicators identifying the exact composition of the pill. There could be an outside covering over each pill that has a code printed on it to identify exactly what the pill is composed of. Some coverings of plastic or blister pack can be used to protect the pill from contamination and make the pill more readily identifiable. In some embodiments some coverings could also include low-frequency RFID tags to make counting and identifying the drugs easier. When inserting the pill would pass through a small scanner on the dispensing device that confirms the correct pills are being inserted into the device.

Once the pills are loaded and confirmed, the drug dispensing equipment can be closed to move to the final step of provisioning. The drug watchdog is informed of this closed state and securely relays this information to the central database. Finally, the provisioning is completed when bio-identity information is successfully provisioned from the drug consumer and the dispensing device enters the provisioned stage. When it enters this stage, the central database is informed via a secure message exchange. Only when the dispensing device is in the provisioned stage can the central database send a begin deployment to move it into the deployment stage.

In this application bio-identity is defined as anything directly related to the drug consumer. Therefore, a person's bio-identity can include biometric information like fingerprints, facial recognition, voice recognition, palm scan, deep vein scan, retina scan and any combination of biomedical data. In this application biomedical data refers to information physically related to the drug consumer. For example, it would include urinalysis results, heart rate results, EKG results, EEG results, blood results, stool analysis, urine test strip results, saliva analysis, tear drop analysis or many other possible identifiable parameters about the drug consumer. Additionally, biomedical or biometric information could include photographic or video information. For example, an initial photograph might be used in front of a drug dispenser to confirm the visual identity of a drug consumer and then subsequent photographs can be compared to it. In another example a photograph might be taken of a drug consumer placing a pill in their mouth this is biometric evidence of drug consumption in some embodiments. In another example a drug consumer takes a photograph of a urine test strip and provides that as a status result from taking their medication. When all the biometric and biomedical data has been collected and confirmed to the drug watchdog's satisfaction and configuration requirements, the dispensing device enters the provisioned stage.

Deployment stage is the process where the drug watchdog program executes the dosage rule file by opening, reading, protecting and processing the information. The central database determines exactly when the dispensing device will enter the deployed stage by sending a secure message indicating it can move to this final stage.

Executing can further involve setting up timers, triggers, hardware interrupts, events and other actions to guide the behaviour of the dispensing device. The guidelines and rules for the prescription are managed and enforced by the drug watchdog after the drugs are secured within the dispensing device. Deployment also includes the drug watchdog providing tracking information for detected events that transpire on the dispensing device. The events can also be detected on other dispensing devices connected to a central database. For example, whenever drugs are consumed, drug low warning messages, dispensing device power issues and many others. Further details on these messages are provided herein.

Authorized health support workers can then see these messages on a connected interface and be warned of alerts when series issues arise. The drugs that are placed in the dispensing device could be in solid, in some embodiments in liquid form, they could also be in a vapour form. In some embodiments the drugs are tablets or in other embodiments the pills are capsules. The capabilities and different types of dispensing devices will provide for a myriad of possible embodiments depending the type of drugs that need to be dispensed.

For the authorization stage, there are several authorization embodiments to confirm which health care professionals are allowed access to the drug monitoring system. The following are just a few of the embodiments that can exist when deploying the system.

In one embodiment a certified doctor and a certified pharmacist are directly granted rights through the creation of a login and password access. This could be done in a private institution, like a hospital, health clinic, drug trial program a seniors' home or in many other embodiments. In another embodiment, the company running the cloud-service offering hosting the central database verifies every person before creating an authorized login and password for them. In these embodiments, one or both involved of the drug prescriber and drug dispenser will log into a central database to have their credentials confirmed.

Once authorized, the doctor might initiate the provisioning process which starts with accessing a user interface (UI) for the creation of a dosage rule file and the pharmacist completes the dosage rule file before it is loaded onto the dispensing device. Either of these individuals can then extend a limited authorization to one or more health care worker to see tracking information and to receive alerts from the dispensing device for a given drug consumer.

In another embodiment an e-prescription system like PrescribeIT™ in Canada, is used by the certified doctor and the certified pharmacist to establish a prescription for the patient. In the United States more regionally-based and product-based solutions for e-prescribing are used like the SilconMesa's solution called DrFirst EPCS Gold 2.0, Allscripts Healthcare Solutions, AdvancedMD, AllegianceMD and many more. Once authorized, the provisioning stage can begin with the building of the dosage rule file by interfacing to the e-prescribing software to extract the prescription information to sending it securely to the correct dispensing device using the central database. A national service like PrescribeIT™ in Canada is created by using information from governing bodies for doctors and pharmacists to ensure every person in the e-Prescribing system is authorized. In these embodiments the doctor may, or may not initially be involved with the use of the e-Prescribing service. In this embodiment the pharmacist would then use their credentials to create and finish of the dosage rule file on their own. The pharmacist can also add security access information for the doctor and other health care providers through the dosage rule file before it is loaded onto the dispensing device.

In another embodiment there are no legal credentials held by the central database. In one embodiment the pharmacist connects a dispensing device to their computer to establish the authentication stage. With the dispensing device attached they are able to login to the central database by the fact that the dispensing device user has a known, verified dispensing device attached. In this embodiment the central database is then able to communicate to the dispensing device through the user's computer. This conversation then allows interrogation of the dispensing device to ensure it is known and available for deployment to a new user. This person can then create a login/password for themselves to access information for this specific dispensing device. In some embodiments, if this dispensing device owner then uses a consistent login/password they can see all the dispensing devices they have used this same authentication process with.

Once authenticated using this embodiment, the authorized user can then start the provisioning stage. The first step in provisioning is accessing a UI for the creation a dosage rule file. They also can add other people who can change the dosage rule file and see the tracking information. In this embodiment any person can use the dispensing device to manage drug consumption and monitor that drug consumption for a patient. As mentioned, this could be a health care work, a child, a spouse or a loved one caring for a sick friend. They might even add information about the insurance company providing the financial support for the medication so that certain limited information can be provided back to them. Such management might be very important for a person with Alzheimer's disease for example.

The next embodiment is similar to the previous example. In this embodiment there is also no credentials kept on the central database. The pharmacist or loved one connects a dispensing device to their computer and then only talks to the dispensing device from their own computer. The authentication stage is employed by creating a secure login/password access to this dispensing device. If a login has already been created, they can re-enter this same login value to gain access. In the case of a non-professional health care or loved one using the dispensing device a bypass password can be created. If the dispensing device is totally empty of drugs then perhaps after a few failures the dispensing device would open regardless.

In this embodiment, the first steps of provisioning involve the person building the dosage rule file directly on the dispensing device. In turn the dispensing device talks to the central database on their behalf to upload the dosage rule file. As in other embodiments, the user can then add additional people to see the contents of this dispensing device. This could also include providing the additional users with their own login/password to view data and messages generated by this dispensing device on the central database. The central database verifies all the information and the state of the dispensing device before allowing it to be opened. In this embodiment any person can use the dispensing device to manage drug consumption and monitor that drug consumption for a patient. As mentioned, this could be a health care work, a child, a spouse or a loved one caring for a sick friend. Such management might be very important for a person with Alzheimer's disease for example. These and other embodiments are possible when following the steps laid out in this drug management system.

In another embodiment of authentication, the person using the dispensing device connects to the central database and enters a piece of required identification information associated to the dispensing device. This could be a serial number, a unique code or a manufactured identifier on the dispensing device. The central database first verifies the identification information and attempts to communicate to the dispensing device over a cellular network. In this embodiment the dispensing device supports a wide area cellular network communication, a private wireless local area network, or a public access WiFi addressable location.

When communication is established it sends a message to the dispensing device to immediately perform a change in state. In some embodiments, this change in state could be to illuminate some LED lights in a unique pattern, in other embodiments it could be to make a series of beeps and in another embodiment it could display a number on a screen or some other action that requires a visual confirmation. The person planning on using the dispensing device can then enter the unique change in state presented by the dispensing device at the central database to pass the authentication stage. If their input matches what the central database has sent to the dispensing device, they are considered authenticated and can work with that dispensing device to start provisioning and create a dosage rule file.

In some embodiments this change in state could be performed more than once to ensure the person who has logged onto the central database is indeed in possession of a valid dispensing device. Once the person finishes the dosage rule file it can be downloaded to the dispensing device and the dispensing device will open for the loading of the drugs. Once closed a bio-identity input can then be collected and verified and the dispensing device can enter the provisioned stage. Only in the provisioned stage can the central database can move the drug watchdog into the deployed stage.

The overall system operation is controlled through a shared central database that tracks a dispensing device and allows the owner of the dispensing device to monitor drug consumption. In some embodiments the system is used by certified drug prescribers and drug dispensers. Different embodiments will be illustrated showing how drug prescribers and drug dispensers can coordinate their activities to create a safe and secure system for prescribing drugs. In these embodiments the coordination between prescribers and dispensers is essential when dealing with high risk drugs. In other embodiments the owner of a dispensing device can be anyone offering support services to a drug consumer. In these embodiments the drug consumer might have need for advanced control and monitoring of all drug consumption for greater protection. For example, in the case of a person with Alzheimer's disease, an addict, even a young child, or a teenager where such protections could save their life.

In those embodiments where a drug prescriber is involved in the system they could be a nurse practitioner, a dentist, a physician, optometrist, pharmacist, or other persons who are authorized to issue a prescription Within this application when the term prescriber or drug prescriber are used they refer to any person that has authority to prescribe drugs to a patient. However, the system is flexible so that the drug prescriber does not have to be involved at the initial stage of drug prescribing. In some embodiments the drug prescriber might use legacy methods to provide a prescription to a drug consumer. In turn the drug consumer seeks out a drug dispenser to receive the prescribed drugs.

In many embodiments these prescriptions are filled by a drug dispenser, which could be a doctor, a pharmacist, a dentist, emergency medical technician (EMT), home care aides, midwife, nurse or other individuals who are authorized to fill a prescription or dispense drugs. In some embodiments the system is used by a person acting as a proxy for the drug dispenser in order to provide additional protection for a patient. In these embodiments this person might be a health care worker, a family member or a relative taking care of a patient. In these embodiments the user of the system might have received a prescription from a pharmacist and has placed this prescription within a dispensing device on behalf of the drug consumer.

Within this application when the term dispenser or drug dispenser are used, they can refer to any person that is authorized to provide and monitor the physical drugs to a patient. The person could be working in a professional and registered capacity, or they could be working on behalf of drug consumer to help protect them from inappropriate drug consumption. The drug prescriber and the drug dispenser are both focused on managing a patient. Patients are individuals that are in need of (or claim to be in need of) having a drug prescribed and/or dispensed to them. In this application the patient needing drugs can be referred to as a drug consumer.

A shared central database ("central database") is defined as a common hub where prescribers and dispensers coordinate their activities. In this application the term central database and central server can both be used to refer to the control point for all dispensing devices. Effectively the central server houses the central database in a computing environment. The central database may also work in conjunction with a regional or national e-prescribing system like the PrescribeIT™ system. The central database could also be behind a secure firewall, e.g., within a pharmacy or within a doctor's office. This could be within a hospital or running as a cloud-computer service offering. Wherever the central database is located the prescribers and the dispensers have secure access where prescriptions for drug consumers and tracking information on their consumption are securely stored.

In one embodiment the shared database is implemented as a web service capable of allowing Internet web browsers to access an interface to submit, examine and execute prescriptions and consumption information. In one embodiment customized Electronic Medical Record (EMR) software within a doctor's office and Pharmacy Management Software (PMS) within a Pharmacy can inter-communicate with the central database to upload prescriptions that can be used for dosage rule files. These same links also allow status, alerts and feedback information to be sent back to the EMR and PMS systems to help track and monitor drug consumers.

In another embodiment a central database is populated with authorized individuals from an organization like the College of Physicians and Surgeons of Ontario (CPSO), or Health Canada, the Medical Counsel of Canada, U.S. Department of Health and Medical Services, American College of Physicians or similar regulatory bodies around the world. In this embodiment this master database is a starting point for any prescriber or dispenser to acquire and create an authorization login to the central database. In another embodiment a hospital might establish who has privileges to prescribe and dispense drugs. In this embodiment internal administrative hospital staff might populate the central database for use within the hospital for prescribers and dispensers that have hospital privileges. In another embodiment the drug watchdog on the dispensing device creates login rights for the drug prescribers and drug dispensers. In this embodiment the drug watchdog running on the dispensing device acts as an extension of the central database to ensure proper authentication procedures are followed. In this embodiment the drug dispenser creates one or more authorization login privileges within the dispensing device when it is first provisioned for use by a drug consumer. Then the dispensing device securely uploads these authorization logins to the central database for later use by drug prescribers, drug dispensers and other health care professionals.

In another embodiment login privileges and authentication is established by the system when a drug prescriber and drug dispenser match their identity with a list of all known identities within the central database. Once populated with information as described earlier the prescriber and dispenser provides several matching information elements. In some embodiments the matching information could include one or more of their full name, practise name and address. In other embodiments it could also include a license to practise identifier and/or login code.

Once a drug prescriber or drug dispenser is identified there could be additional security requirements to further protect against fraud, identity theft and attempts to abuse the system. In some embodiments additional security questions might be required that only the prescriber or dispenser would be able to answer. For example, in this embodiment they might be asked to input the street name they were born on, the name of their first school or the name of their first pet. These and other personal questions provide a unique way to hamper someone trying to steal or abuse another person's login.

In another embodiment the prescriber or dispenser would be required to provide a biometric using either the dispensing device's biometric reader, or through a compatible biometric reader. In these embodiments a fingerprint, retina scan, facial scan or some other biometric value would be taken at the local location and uploaded to the central database. Once uploaded it is added to the login credentials and each time the prescriber or dispenser login they have to provide the same biometric. Each time the prescriber's or dispenser's identity is matched they become an authorized user within the central database system.

Once authentication is established, the first step of provisioning starts with the creation and management of the prescription and configuration information for the dispensing device. The creation is facilitated through a UI provided to one or more of the owners of the dispensing device. This information is collected into a single file called the "dosage rule file" within this application. Although traditionally seen as a physical file this might also be viewed as a collection of information that is exchanged in a message as a single parsable message.

In an example embodiment, a Java Object Notation (JSON) message carrying all the elements of the dosage rule file is exchanged between the central database and the dispensing device.

There are several embodiments for the creation, management and modification of the dosage rule file. In one embodiment the dosage rule file is created within the dispensing device by the drug dispenser at the time of provisioning for a drug consumer. In another embodiment the dosage rule file is created by the drug dispenser on the central database and downloaded securely to the dispensing device. In another embodiment a drug prescriber creates the dosage rule file on the central database, and it is later located by a drug dispenser and downloaded to the dispensing device.

However the dosage rule file is created, it will contain information related to the prescription, how the drugs should be taken and a set of configuration settings for how the dispensing device should work with the drugs. The table 1 illustrates some illustrative examples of the fields and values within the dosage rule file.

TABLE 1

| | |
|---|---|
| Name of Drug | Rx Identification |
| Commonly Used Drug Name | Secondary Name |
| Prescriber's Name, Address, Phone | Contact Information |
| Prescriber's Official ID reference number | From Oversight Body |
| Patient Name, Address, Phone | Identification of Patient |
| Patient Email or Cell Number | Alerts for Patient Allowed |
| Patient Health Card Number | SIN (Canada) or SSN (USA) |
| Dosage, strength information | Perhaps Specific Drug |
| Frequency of dose guidelines | Times per day |
| Specific Dosing Time for Each Slot | Array of Slot actions |
| Start time for Drug Dispensing | Day: Hour: Minute |
| Number of pill per dose | 1 to 'N' pills per dose |
| Minimum spacing for each dose | Min. Gap time (used for 'extra' dosage) |
| Sleep hours to avoid dosage | 'hh:mm' to 'hh:mm' times spread |
| Picture is required for final provisioning | Of Picture input required in file for patient |
| Picture approval required | Frequency of approval (days, weeks, month) |
| Picture is required at every dose taken | picture proof is required to get more drugs |
| Extra Dosage Allowed-Patient driven | Number per day |
| Time needed between two doses | Minutes or hours |
| Maximum doses allow | Max total per day |
| Should continuous missed doses halt further usage? | Yes or No |
| IF YES: Number of continuous doses missed before halting? | Number of doses (numeric value) |
| How long after notification before considering drug missed? | <Hours and Minutes, i.e. XX:YY> |
| Maximum Refills Allowed | May allow auto refill |
| Food, Drink and Empty Stomach guidelines | Important Requirements |
| General Comments for Patient on Usage | Comments for Printing |
| Maximum dose before refill allowed | Overlap guidelines |
| Minimum remaining before warning | Warning light turns on |
| Send Warning Message if dose missed? | Yes or No |
| Max Time after missed dose for a message | Minutes or Hours |
| Identification of Drug Dispenser-if known | Name and ID of person |
| Password for Drug Prescriber | And Contact Info |
| Password for Drug Dispenser | And Contact Info |
| Password for Other Health Support | And Contact Info |
| Drug Insurer Information, Update Permission | Email Address for Information |
| Details about Drug Dispenser | License Number, etc. |
| <Other Various Configuration Choices> | <Many Embodiments> |

This is an example of a set of configuration elements that can be encoded in a dosage rule file. There are many other embodiments for the types of fields that could be present within the dosage rule file and available to a drug prescriber to select from.

Once connected to the central database the drug prescriber device will have an interface to guide them to fill in the necessary information. This includes a help menu in case there is any confusion on the fields provided. In some embodiments some of the fields will be optional, for example if the prescriber answers no to the question: 'Send Warning Message if dose missed?' then they will not have to answer the question "max time after missed dose for a message". Not every possible field is listed in table 2, table 2 is illustrative of some of the expected fields.

The authorized user for the dispensing device can also add other authorized users. As illustrated by table 1 the authorized user can add a drug prescriber, for example a doctor. It could also involve adding a healthcare support worker, like a nurse or a person with power of attorney. Further there could be insurer information added so that the insurance company that is paying for this drug treatment is kept appraised of the patient's compliance.

Various biometric and biomedical requirements can also be added to the dosage rule file. The example of a picture requirements is shown but the system could include urinalysis results, blood testing results (for example a diabetic blood test), heart rate, EKG, EEG or many other possible tests. The system might require approval of the biomedical information. This approval might come daily, weekly, monthly or in some embodiments after every single dose taken.

In some embodiments other more complex configuration options might be allowed perhaps related to location issues and GPS functionality. The prescriber might need to understand if the drug consumer is roaming outside of their city or country.

Fields like the dosage, the frequency of use, maximum drugs remaining before refill, sending a warning message if a dose is missed and similar configuration elements will be used by the dispensing device to help guide its behaviour. The dosage rule file contains all the fields found within a drug prescription but with certain additional components to support function of the dispensing device.

In some embodiments the exact time and action for every available slot or drug within the dispensing device is carefully listed to guide every action on every given day. Also shown in this example is the actual start time when dispensing should commence.

In some embodiments the drug prescriber or the drug dispenser must halt all drug consumption if too many continuous doses of the drug have been missed. In this embodiment the drug consumer has failed to perform the necessary bio-identification procedure to extract the drugs when the dispensing device has informed them their dose is due. The dosage rule file can also indicate the length of time that must pass before the available drug doses is considered missed. In some embodiments the dosage rule file also contains separate access codes or passwords for viewing information provided by the dispensing device at the central database. In some embodiments this could include a login and password and in other embodiments just a password. In some embodiments an email address, cell phone number or other contact numbers could be present. In these embodiments when email addresses or cell phone numbers are present it is possible to send alert messages and alarms to a wide range of health care providers if something were to go wrong with the dispensing device or the drug consumer working with the dispensing device.

Additionally, in some embodiments the dosage rule file can contain license and tracking information on the drug dispenser. In several embodiments that follow the drug dispenser holds a great deal of power and trust in the deploying all forms of drugs and in some embodiments high-risk drugs. Inputting this information can also assist in allowing a drug dispenser to see all the dispensing devices they have deployed in the field.

The dosage rule file is also linked to a specific drug consumer via their unique identification. In Canada for example this identification could be their health card number, a passport number, a driver's license or even a social insurance number (SIN). In the USA, for example, this could be a drug consumer's social security number (SSN), a driver's license, a state issued identity card, an insurance health card number or even a passport number. This identification can be used in a variety of embodiments within the system. In some embodiments this number will be used by the drug dispenser to locate a dosage rule file created by a drug prescriber when requested by the drug consumer trying to get their prescription filled.

In other embodiments the identity information can be used to ensure this same drug consumer does not try to thwart the system and go to multiple drug dispensers to get their prescription filled multiple times. In other embodiments this identification is used to ensure the same patient has multiple dispensers to enable the hot-swap option for ensuring a continuous drug supply. In other embodiments this identity is also used by governing bodies or government agencies to confirm who is using certain kinds of high-risk drugs. Contact identification like an email address and cell phone number could also be present so the system can alert the patient should their drugs be getting low and they have failed to take notice of the warning provided by the dispensing device. Other alerts could be sent to indicate the power on the dispensing device is low and it needs to be plugged in for recharging.

In some embodiments a drug consumer might not have proper identification. Perhaps they are homeless, they do not have identification with photo and address information present, they could be a new immigrant, or not have official ID for many other possible reasons. In this embodiment it is possible for the drug prescriber to possess a dispensing device or a compatible biometric reader for the sole purpose of taking a biometric from the drug consumer and uploading it to the central database. The biometric then becomes associated with the dosage rule file and in some embodiments, it gets uploaded to the dispensing device for drug dosage authorization. Once this is done the drug consumer will perform the same step at the drug dispenser's location in order to be matched to a dosage rule file. In severe cases of drug abuse and drug addiction these types of extreme measures are necessary to reduce abuse associated with high risk drugs. In other embodiments the system requires that a biometric be taken from every drug consumer and uploaded by the drug prescriber.

In other embodiments the drug prescriber only takes the information they can easily acquire, even just a name of the drug consumer. However, in this embodiment the drug dispenser will always take a biometric and the central database must scan all current and past dosage rule files to ensure this drug consumer is not trying to abuse the system.

Another element of the system is when the drug consumer picks a drug dispenser to fill their prescription and locate or create their dosage rule file. In some embodiments the drug dispenser works directly with a dispensing device to create the dosage rule file with the information provided by the drug prescriber. In some embodiments the original prescription from the doctor was on a handwritten prescription pad, in other embodiments this could be a computer printed prescription from the doctor's office. In this embodiment after completing the dosage rule file on the dispensing device, the dispensing device will upload this information to the central database once the drug dispenser finishes the full provisioning of the dispensing device and it enters the provisioned stage.

In other embodiments the drug dispenser has created login rights at the central database and will create the dosage rule file directly within the central database. In this embodiment once the dosage rule file is created, it is securely downloaded to the dispensing device.

In some embodiments the dispensing device is connected to the drug dispenser's computer and in other embodiments the information is received via another communication path. In some embodiments the drug dispenser has created the dosage rule file on the central database and has been pre-selected by the drug prescriber. In this embodiment the drug dispenser could have a list of dosage rule files under their login name already.

In those embodiments where the drug dispenser has to find a dosage rule file on the central database, they will search for the dosage rule file in several ways. In one embodiment, they might search for the partially built dosage rule file by using the drug prescriber's name or special identification number given to them by the drug consumer. In another embodiment they use the drug consumer's name or specific identification to search for all dosage rule files listed to this drug consumer. In another embodiment they can search using both the drug prescriber and the drug consumer's information. In another embodiment they take the biometric of the drug consumer and it matches the biometric to the dosage rule file. In yet another embodiment the dosage rule file is automatically posted to the drug dispenser's login profile by the drug prescriber at the request of the drug consumer.

There are several embodiments that allow the central database to determine how a drugs within dispensing devices can be assigned to drug consumers. Since the dispensing device and central database keep track of all dosage rule files in all dispensing devices, and the drugs contained within the dispensing devices it takes full charge of the dispensing device's activities.

In one embodiment, a drug consumer can not take their dosage rule file or a dispensing device to another drug dispenser to get refilled. In other embodiment, the drug consumer can also not take their prescription to another drug dispenser to have it filled as they will be flagged by the central database and it will not let the drug dispenser proceed with provisioning.

In another embodiment, the drug consumer is able to be in possession of two or more dispensing devices with the same drug in them. In this embodiment only one dispensing device actively deployed and dispensing drugs for them. Once the first dispensing device is empty of all drugs would the second dispensing device receive a command from the central database to deploy. Once deployed it will then take over and provide drugs to the drug consumer, thus ensuring a continuous supply of drugs. This process is called the hot-swap method and the central database who counts and tracks all drug consumption (taken and missed doses), can control this operation.

With the drug dispenser selected, dosage rule file downloaded, and the drugs loaded, the drug consumer must provide a bio-identity to the drug dispenser to complete the provisioning process. In some embodiment part or all of the bio-identity already associated with the dosage rule file when the biometric was taken for initial drug consumer identification. In these embodiments the biometric could be uploaded and used by the dispensing device. In other embodiments the drug consumer must manually enter their bio-identity into the dispensing device with the drug dispenser watching. This bio-identity will be used later to allow access to their daily dose of drugs held within the dispensing device.

When the drug watchdog is running on a separate computer from the drug dispensing device the biometric will be collected on the computer running the drug watchdog to allow authorization of all drugs to be extracted.

In some embodiments the bio-identity could be only a biometric and in other embodiments it could include biomedical information. Examples of biometric data would include a fingerprint, retina scan, heart rhythm or some other unique property that is inherent to the drug consumer. In other embodiments the drug consumer could have a subdermal implant that provides a unique identification held only by that person. Many other embodiments are possible including facial recognition, vein scan and other bio-centric techniques.

To change dispensing devices for a specific prescription the drug consumer would have to get the same drug prescriber involved who created the dosage rule file in the first place. The drug prescriber will assist in releasing their relationship to any current dispensing devices and a specific drug dispenser. In some embodiments where the dispensing device develops a mechanical problem or defect the drug dispenser can swap the existing drugs between dispensing devices within their secure location.

In some embodiments the bio-identity will use a secure enclave method for storing and matching the biometric. In some embodiments a biometric enrollment method is used to extract key identifying features of the individual from his or her biometric input. An algorithm can then be built from original input and used to confirm subsequent biometric inputs on that system. In this embodiment, a new input is simply provided to the biometric algorithm, that encapsulates the key identifying features of that individual, for reconfirmation that the biometric matches the original. In this embodiment the biometric itself is not stored on the dispensing device, just an algorithm that is created by the original biometric. When this algorithm is executed with input from the biometric reader it produces a match or no match answer. This method can be used by smartphone and small devices with limited computing resources and a high need for security.

In another embodiment the original biometric is stored in a secure enclave and protected from tampering. Then when subsequent biometric inputs are received, they can be passed to the secure enclave who performs hidden operations on the biometric to match the two. The secure enclave is tamperproof to protect the data elements storing the drug consumers identity.

Once deployed the drug watchdog and dispensing device cannot be re-assigned through another drug dispenser or to any other location. There could be a dangerous collection of drugs within the dispensing device and these are the responsibility of the drug dispenser. In those embodiments where the drug watchdog is running on a separate computer system, it is possible for one drug watchdog to manage several dosage rule files with corresponding drug dispensing equipment. In this example configuration the drug watchdog associates a dosage rule file to a specific piece of drug dispensing equipment and maintains a secure relationship with that drug dispensing equipment separately from all others. These separate, secure relationships are used to ensure accurate of drug consumption through the drug dispensing equipment.

In some embodiments the drug watchdog protects the dosage rule file (or the information that makes up the dosage rule file information) and keeps it encrypted when stored on the dispensing device. This 'at rest' encryption might use a dynamically generated encryption key held within a secure enclave. It could also receive an 'at rest' encryption key from the server over that secure link. In these embodiments, it is only decrypted when it is in active use to dispense drugs.

In other embodiments the dosage rule file can be encrypted using encryption keys linked to the dispensing device identification. The encryption limits and restricts all access to the dosage rule file by other programs and an attempt to hack into the dispensing device to modify the dosage rule file would fail as the stored copy of the dosage rule file is encrypted. Attempts to modify the dosage rule file would result in damage and a new copy (also encrypted) would have to be downloaded from the central database.

In other embodiments where the drug watchdog is running on a dispensing device with other programs doing additional operations, the drug watchdog will stop and block any read, write, delete or modify actions by these programs. The drug watchdog can also report on all activities related to the dispensing device itself. This includes when it dispenses drugs and any attempts to break into the tamper-proof area that holds the drugs, or unauthorized activity monitored by the watchdog software. In some embodiments the watchdog software reports back on the GPS location and if the drug consumer fails to take their drugs or if the dispensing device has been tampered with it can report back with a warning that something could be wrong. Cellular connections as discussed above are established in several ways.

In other embodiments the secure connection is created via an onboard cellular connection that is possible over 3G and 4G networks. In these embodiments embedded cellular OEM chipsets are used to provide 3G, 4G, LTE and WiFi (802.11) type communication options to the dispensing device. In other embodiments the drug watchdog is contained within a wearable lanyard or support device which contains the 3G and 4G cellular link equipment. In other embodiments a cellular phone is running the drug watchdog and it supports 3G and 4G communications back to the central database. In yet other embodiments a smart watch or wearable computer is running the drug watchdog and it is controlling the drug dispensing equipment.

In some embodiments these options are important when a drug consumer takes the dispensing device with them from the drug dispensing location. In these embodiments the drug consumer may or may not have connectivity at home or may be homeless. These cellular methods can be used in conjunction with USB or Bluetooth connections or as an alternative. In some embodiment even if the dispensing device is connected via USB or Bluetooth to a drug dispenser's computer it still opens a secure cellular connection and uses both the cellular connection and the computer connection to provide verification over two connection routes. These embodiments exist to further reduce efforts to thwart the system and reduce abuse by drug consumer to take more drugs then they are prescribed.

When it is time to reload the dispensing device, it must be empty or nearly empty of all drugs and not currently deployed for a drug consumer. Since the number of physical drugs entered matches the prescription, the drug watchdog and the central database know precisely when the drugs contained in the dispensing device are completed. In some embodiments, the dosage rule file will allow for some overlap, to allow for "topping up" the number of drugs in the dispensing device to ensure a drug consumer does not run out. The overlap would be configurable, and in many embodiments might be a single digit number from 0 to 9 for example.

In other embodiments the central database allows the consumer to have two or more dispensing devices with the exact same drug in them. The central database, who is tracking every drug consumed or missed, determines when the first dispensing device is empty of drugs will deploy the second dispensing device for active use.

There are also embodiments where any unused drugs might be as a result of skipping one or more doses on a given day. The drug prescriber might require these drugs to be accounted for and the drug consumer is not allowed to have additional medication. This information can be encoded in the dosage rule file and the drug watchdog detects the missed doses and can halt the deployment of the dispensing device if the drug consumer does not follow the dosing guidelines. In these embodiments, where drugs are left over in the dispensing device when it is returned, it is up to the drug dispenser to decide whether to destroy these drugs or include them in the next refill of the dispensing device and reduce the overall amount added.

The central database will keep track of the number of dosages it actually ejects (has remaining) for a drug consumer and will be able to notice anomalies in the totals. Any such irregularities can then be reported to government officials to act upon, should a drug dispenser be suspect of not following drug consumption and drug dispensing guidelines. Drug dispensers will not be allowed to destroy drugs contained within the dispensing device. The drug dispenser will be allowed to 'top up' the existing amount to match the next dosage requirements or they will have to send the leftover drugs back to the manufacturer for destruction.

In those embodiments where the drug dispenser connects to the central database from their computer, they might use a public network like the Internet. In those embodiments where a public network like the Internet is used a secure socket layer (SSL) connection might be initially used to create a private and secure link to the central database. On top of the SSL connection the central database and drug watchdog can establish their own private security method for enhanced security. If an Internet web browser is used a special extension to the browser could be used to facilitate this conversation between the computer and the dispensing device.

An encryption process is deployed between the central database and the drug watchdog to encrypt the dosage rule file before it is exchange between the central database and the drug watchdog. As mentioned in some embodiments the central database sends the dosage rule file to the central database and in other embodiments it receives the dosage rule file from the central database. In embodiments where the drug watchdog is running on a separate computer, the encryption method can be extended directly to the drug dispensing equipment Depending on the embodiment several different types of encryption could be implemented using different processes that best match the requirements of the system. This encryption technique, built at the application layer, creates a strong bond and encoded link between the dispensing device and the central database. This level of security also provides a higher level of protection for the dosage rule file and all the messages exchanged between the central database and the dispensing device. In some embodiments this allows the drug watchdog to keep the information in an encrypted state to protect it from malicious software or other hacking methods. Such a security strategy can be used on top of other lower-level security methods like Secure Sockets Layer (SSL) using both server and client certificates are commonly used to provide very secure communications.

When additional security is required there are many embodiments to implementing a proprietary solution. For example, in one embodiment public-key cryptography might be used. In this embodiment the central database holds the public key for all deployed dispensing devices that are manufactured and released for sale. In this embodiment when the drug watchdog first initializes it detects the lack of a public/private key pair and generates one using several possible embodiments to create a large prime number needed in the generation of the asymmetric encryption keys.

In one embodiment it starts with a number derived from its serial number to search for a large prime number. In another embodiment it might use a number found on its subscriber identity module (SIM) card, like the international mobile subscriber identity value (IMSI) as a starting point to find a large prime number. Then the manufacturer provides the dispensing device's public key to the central database as each dispensing device is built, tested and entered into the system. This public key is then associated to a specific dispensing device via its unique identifier or serial number. This then allows the central database to send encrypted messages to a specific device when it is selected for use. Similarly, the public key for the central database is provided to the dispensing device so it can encode messages sent to the central database. This embodiment for encryption would be useful to implement if the system wanted to use a cellular method for provisioning the dispensing device without connecting it to a drug dispenser's computer. The encryption might involve an agile encryption methodology. In this embodiment there might be several different types of encryption methods to encrypt the data using the public/private key pair. The type of encryption selected might be numbered or change periodically to avoid being discovered.

In another embodiment a seed value might be used to negotiate a shared symmetric key between the two ends. The seed value might be extracted from the computer connecting the dispensing device and the central database for example. In those embodiments where the drug watchdog runs on a separate computer, the seed value might come from the drug dispensing equipment and it is known to the central database in advance. In another embodiment the seed value is a serial number of the dispensing device that has also been provided to the central database. In this embodiment the seed value would then be used to negotiate a symmetric encryption key used to exchange information. Such seed values are used with negotiation protocols like Diffie-Hellman, SSH (Secure Shell), quantum-safe cryptography and SPEKE (Simple Password Exponential Key Exchange). This embodiment is useful when a computer connection over USB is used to ensure the dispensing device is in a safe and enclosed environment before provisioning with drug. In all cases whether the encryption keys are created during manufacturing, negotiated using various seed values or created based on identification information held within the dispensing device they are always linked or selected based on the specific dispensing device selected to receive a given dosage rule file for a drug consumer.

Once the dosage rule file information is loaded into the dispensing device the drug dispenser can review the information within the dosage rule file at any time. This information will include comments and suggestions from the drug prescriber, dosage information, frequency of drug consumption and any other relevant information. In some embodiments some of this information can be printed off or copied out in order to populate the dispensing device with the correct dosage of drugs.

In some embodiments this information from the dosage rule file is included with all the dosage instructions, drug side effects and warning information for the drug consumer. In other embodiments the drug dispenser can print off information for the drug consumer and affix a prescription brief on the dispensing device, like affixing instructions onto a pill bottle. With the dosage rule file successfully downloaded, the first step in provisioning allows the dispensing device to be opened and loaded with the drugs matching the dosage rule file.

In some embodiments, a portion of the total drugs defined by the prescription are loaded into the dispensing device, for example just a week supply of the drugs. In some embodiments each drug is identified and will be confirmed as it enters the dispensing device. This might involve bar code scanning, using an outer covering with bar code information or other simpler detection mechanisms. The drugs could also be enclosed in a small package that contains a low-frequency RFID tag that can be detected and read by the dispensing device. Once loaded the dispensing device can be closed.

With all these setup steps completed the drug watchdog takes charge of the dosage rule file parameters and moves to the final step of provisioning. To be capable of entering deployment, the drug dispenser must successfully acquire and provision bio-identity information from the drug consumer. In some embodiments this can focus on biometric information and in other embodiments biomedical information can be required from the drug consumer. This biometric information could be biometrics like facial recognition or fingerprint data. In some embodiment this could be voice recognition, deep palm or vein scans or even retina scans. In some embodiments the provisioning of biometric data involves the dispensing device confirming the biometric information is correct by requesting the drug consumer to match the biometric information collected a few times before considering the biometric stage fully provisioned. Only when the central database is told by the drug watchdog that bio-identity information has been confirmed, will the dispensing device enters the provisioned stage. In the provisioned stage it possible for the central database to send a begin deployment command to begin the dispensing of drugs by the dispensing device. The central database makes the final decision when deployment is allowed for the dispensing device.

At different times additional biomedical information may also be required before and during deployment. This information could be used to verify drug consumption or to determine overall health. This could include urine analysis, heart rate results, EKG, EEG, blood test results and other information that must be provided. In some embodiments this is provided directly to the dispensing device and in other embodiments it is provided to the central database through an external device and associated to the dispensing device and drug consumer. In one example, this external machine could be an blood pressure machine capable of external communications, or a person's cell phone that has been associated to the drug consumer. In these embodiments where an external machine is used, the dispensing device would be given a message from central database to finish the provisioning and enter the provisioned stage. The provisioned stage indicates that at any time the central database can send a begin deployment command to being the dispensing of drugs.

Once the biometric and biomedical information is collected and confirmed, the dispensing device enters the provisioned stage. It is only in this stage can the central database send a command to active the deployment stage by the drug watchdog. Entering the deployment stage results in the drug watchdog that is running on the dispensing device to enter normal operation based following the contents of the dosage rule file. The dosage rule file contains a wide range of behavioural information to control operation and trigger special situations related to the use of the dispensing device. The drug watchdog uses the timing subsystem and other subsystems within the dispensing device to regulate the correct consumption of drugs held in the device.

In some embodiments LED lights, auditory sounds, sending a message and various visual aids and displays are included to inform drug consumers when their next dose of drugs can be taken.

In some embodiments the drug consumer has provided cellular information, electronic mail addresses and other mechanisms that can be employed to alert them that a drug dose is ready for consumption. In these embodiments one or more messages from the central database could be sent to inform the drug consumer of an important state change within the dispensing device. For example, a low power problem, an RF coverage problem, a low drugs available warning as well as a next drug dose available indication.

In other embodiments the dispensing device has been configured to send the message directly to the drug consumer using the configured communication mechanism.

Communication methods like USB, Bluetooth, NFC and others could be employed to send a message to a cell phone, a smart watch or some other type of computer-based device. In other embodiments the dosage rule file allows the drug consumer some flexibility if they need an extra dosage of drugs, with maximum amounts set and strictly followed by the drug watchdog. These embodiments and many other embodiments will be highlighted through the figures provided in this application.

In some embodiments it is necessary for the drug prescriber to update the dosage rule file to change the dosage of the medication being taken. This embodiment occurs when a drug consumer and drug prescriber are in communication and the drug consumer needs change their dosage amounts. For example, a patient might phone they doctor and ask for more medication for pain relief or less pain medication for pain relief as they are feeling better. In this embodiment the drug prescriber can change the dosage rule file and request it as an update on the drug consumer's dispensing device. This is possible because the central database has a secure relationship with the dispensing device, even when the dispensing device has been deployed and is being used in the field. In some embodiments the change could be delivered near real-time to the dispensing device. In other embodiments there could be check-in intervals. These embodiments are all possible based on the design of the communications link between the central database and the dispensing device.

For example, if the dispensing device supports a cellular connection, the drug watchdog can checks-in at regular intervals to the central database to request updates and upload any status information. During one of these check-ins the central database can securely send an updated dosage rule file to the drug watchdog on the dispensing device once a connection is established. In other embodiments the cellular link is always open and exchanging information. In other embodiments where the dispensing device is using a USB connection and is being plugged in a computer each evening for recharging, the update would be when the computer is activated and a connection can be established.

As mentioned during the deployment of the dispensing device a wide range of tracking messages are relayed to the central database over the secure connection using the encryption keys selected. The messages include the exchange of the dosage rule file, including updates to the dosage rule file. In those embodiments where a network like the Internet message formats can be employed to carry these messages. Data exchanges in a format called JavaScript Object Notation (JSON) can be used for device to device communication using HTTP or HTTPS.

In these embodiments in the header of the HTTP message the dispensing device identifier will be present for every message. This allows the central database to select the correct encryption key to decode the message. In these embodiments the dispensing device acts as a client device on the Internet and must initiate communication to the central database running as the server. Responses to HTTP queries must be encoded using the correct encryption key for a specific dispensing device. Security is maintained as the payload of the message will not be intelligible when the sending does not have the correct encryption keys. In other embodiments other data payload formats can be used to carry the dispensing device identification value in front of all other encrypted data. Similarly, the dispensing device identification would be left unencrypted in these other methods to provide a method to lookup the encryption key.

All exchanged messages would have several categories depending on the nature of the message and its intent. Table 2 below shows one embodiment for the division of the messages and their categorization. In this embodiment each message will be built with four distinct components as illustrated in table 2 below: <device identifier><message-version><message-length><payload data>

TABLE 2

| Header | | | |
|---|---|---|---|
| Device | Identifier/Serial Number | | |
| Message Version | Message Length | | Message Priority |
| Message Payload | | | |
| Code | Meaning | Data Elements | Priority |
| Sent by Central Database: | | | |
| A-1 | Start Provisioning process | Dosage parameters for provisioning, opens main compartment | Medium |
| A-2 | Erase legacy data, clean system | Data to erase (dosage rule file and/or tracking data) | High |
| A-3 | Download of drug monitor required | Time parameters, new release number | High |
| A-4 | Drug monitor program data | Encode and compressed device code | High |
| A-5 | Update to dosage parameters | Update parameters, change state diagram, do NOT open main compartment | High |
| A-6 | Configuration Started | Returns back status, contains count of remaining drugs | High |
| A-7 | Display LED Pattern for verification | Displays for 30 seconds, sends confirmation back | High |
| A-8 | Overrule Requested, immediately | Sends back confirmation and totals of drugs inside | High |
| A-9 | Biomedical Input Received | Proceed to full Provisioned Stage, biomedical input validated | High |
| A-10 | Biomedical Input Validated | Biomedical data received has been approved | High |
| A-11 | Biomedical Input Rejected | Biomedical data rejected, stop all provisioning | High |
| A-12 | Start Deployment | Start deployment, dispense drug following configuration | High |
| A-13 | Stop Deployment | Stop deployment (many possible reasons) | High |
| A-14 | Force Drug Dose | Forces the extraction of a drug dose (perhaps biometric failure has occurred) | High |
| Received at Central Database: | | | |
| B-1 | Poll Message-any changes to report? | Holds open TCP/IP connection if possible | Low |
| B-2 | Dosage Rule File Contents present | Encoded and compressed dosage rule file | Medium |
| B-3 | Status message during provisioning | Details on drug consumer, problems or issues (allow to open, yes/no) | Medium |
| B-4 | Provisioned Stage Reached | Number of Drugs in device (bio-identity collected) | Medium |
| B-5 | Provisioning Started, door closed | Number of Drugs in device (unit closed), waiting on bio-identity collection | Medium |
| B-6 | Drug dose consumed | Timing, delay to dose, drugs remaining | Medium |
| B-7 | Drug dose missed | Elapsed time, time of day, location, other data | Medium |
| B-8 | Drug doses low | Drugs remaining | Medium |
| B-9 | Drugs exhausted | Total time since last dose | High |
| B-10 | Battery Low | Current Battery Level | Medium |
| B-11 | Battery Dead | Drugs remaining | High |
| B-12 | Forced Entry | Probability of success | High |
| B-13 | Computer Login | Success or Failure | High |
| B-14 | Login Failures | Total number of continuous failures | High |
| B-15 | Login Blocked | Max Failures | High |
| B-16 | Overrule Response | Opened Successfully, status | High |

TABLE 2-continued

| | | | |
|---|---|---|---|
| | | and total drugs still inside | |
| B-17 | Biomedical Data Received | Data and data type attached for review | High |
| B-18 | Stomach consumption info | Time confirmation of actual drug ingestion | Medium |
| B-19 | Photo of consumer | Digital picture of drug consumer at dosage | Medium |
| B-20 | Audio Played | Time to Take Drugs message Played | Low |
| C-1 | DEBUG Message | Operational Issue, or code issue | Low |
| C-2 | DEBUG Request | Sever might request debug data from a part of memory? | Low |

Embodiments shown in Table 2 provide one example of a set of messages to be exchanged between the drug watchdog running on the dispensing device and the central database. There will be messages that are sent by the central database, labelled as 'A' messages and messages to be received by the central database, labelled as 'B' messages. Additional message classes are also possible, for example class 'C' message are shown as DEBUG messages for solving low-level operational issues. In some cases a message type might go in either direction, like the dosage rule file payload present message. Each message carries a header with the message version, message length and a priority. In different embodiments the number and size of the data elements might vary. In other embodiments the data elements might use a compression algorithm to reduce the overall size of the message and increase the efficiency of the system. When using cellular communications, it is always a consideration to have smaller data payloads to increase success of message delivery. The final messages B-20, B-21 and B-22 are included for embodiments where the dispensing device supports advanced tracking and audio services.

A portion of the messages exchanged in table 2 relate to special events that take place inside the dispensing device. These might include battery low, battery exhausted, poor RF coverage or cellular communications, low drug levels and many others. In some embodiments to assist the drug consumer, the dispensing device can produce auditable sounds to help guide and warn the user of important issues. The sounds could be noises like beeps and rings, or it could be computer spoken words or recordings.

For example, beeps or rings could be used for indicating the next drug dose is available, drugs in the dispensing device are running low, the battery needs changing and other such issues. Such embodiments might be valuable for an individual with a visual impartment that cannot see LED lights blinking and flashing. In some embodiments the drug consumer has provided cellular phone numbers and email address information so that alert messages can be sent to notify them of important status information regarding their dispensing device. Messages could inform them that the dispensing device needs to be plugged in for recharging, or they need to replenish their drug supply or that a regular drug dose is ready for consumption are just a few examples of the messages that can be sent.

Some embodiments involve the bio-identity operations in the provisioning stage and in the deployment stage can include visual and biological inputs for verification in addition to biometric data. These inputs can take place in many ways to help health care professionals determine how the drug consumer is doing and whether they are taking their medications.

In some embodiments performing the biomedical steps can mean the difference between receiving your next dose of drugs or not receiving the next dose of drugs. In some embodiments the biomedical steps might occur when a drug consumer is initially provisioning their dispensing device. In other embodiments the biomedical input is required at different stages of the drug dosage period. In other embodiments the biomedical input is required both at the provisioning stage and the drug dosage period. There are several functions for these biomedical inputs.

For example, it could be possible to stop a drug consumer from extracting their medication but then not actually taking the medication. The drug consumer might sell their medication (illegally) for money, storing smaller doses to combine into a larger dose, or they might be avoiding the medication. In another example the biomedical data might indicate the drug consumer needs more medication or less medication to do have an improved impact and avoid any harm. Improving patient outcomes is a goal of the health care field. If there are potential ways to maximize patient outcomes using a camera, or biomedical collection methods they are covered under these collection mechanisms.

In one biomedical embodiment the dispensing device can support the ability to use additional resources to collect drug ingesting information to make decisions about drug access. In these embodiments the drugs being consumed have been formulated with additional chemical compounds that when ingested react with the acids within the stomach to create a signal. These compounds are in use today and can provide feedback to the dispensing device as to whether the drug consumer has actually taken their drugs and not sold them for profit.

In this embodiment the dispensing device might use a communication method like Bluetooth or Near Field Communication (NFC) to exchange messages with a wearable device. The device to detect that consumption has taken place could be form of an advanced watch, a ring, a bracelet, a band around the stomach or belt detection device or any other item that is worn or is in close proximity to the body (referred to as a "wearable device") to detect when a drug has been consumed and ingested. When dealing with addiction issues it is essential that maximum controls be in place to limit abuse. In another embodiment, the wearable device might communicate to a mobile device, and the mobile device can then relay the information with the drug consumer's identification and the dispensing device's identification to the central database. In another embodiment the wearable device might communicate to the central database itself.

In this embodiment the worn device can pick up the signal from the stomach during drug consumption. Thanks to the feedback and control of the central database, the drug consumer will be motivated to ensure their wearable device picks up this signal or they will not be able to get their next dose of drugs. In one embodiment once the signal is received the wearable device relays a message to the dispensing device that relays it onto the central database. In another embodiment the wearable device relays it through a cell phone or similar device to the central database with the drug consumer identification and the dispensing device's identification. In another embodiment the wearable device sends the information directly to the central database with the drug dispenser's identification and the dispensing device's identification. Then the central database authorizes the next dose of medication when the time elapses for such mediation within the dispensing device. Since the success or failure of taking a given drug is relayed to the central database, all authorized persons or organizations that are monitoring a given drug consumer will be made aware of their progress.

This closed-loop method allows for even greater monitoring of drug consumption and drug abuse.

In another biomedical embodiment, the provisioning and deployment involves camera or sensor devices, and can involve photo or video data. In some embodiments the dispensing device has a built-in camera feature. In this embodiment a very small camera, similar to those used in a smartphone or in some embodiments even smaller are present within the physical housing the dispensing device. In other embodiments an external camera, like one on a smartphone, may be used to satisfy the biomedical requirements of the system.

In those embodiments where the drug watchdog is running on a device with a camera, for example a smartphone, it is possible for the drug watchdog to use this camera to satisfy the biomedical requirements of the system.

In these embodiments, the camera can be used to take a photograph or video of the drug consumer at different stages of the process. In one embodiment the drug dispenser is told that a photograph or video is required of the drug consumer as part of the provisioning process. In one embodiment this is used to augment the biometric input method at the final stage of provisioning. Once provisioning is complete and the drug consumer takes the deployed dispensing device home, they might have to take a picture of themselves with the drug in their mouth each time they eject a dose of drugs for consumption. The photographs can be compared to a stored image (e.g. photo captured and stored at the provisioning stage) to ensure the correct patient took the photograph and that the drug has been placed into the drug consumer's mouth. In another embodiment, the original picture at provisioning is not required but only a picture each time a dose of drug is extracted from the dispensing device for consumption. These types of choices can be made when the dosage rule file is constructed to help guide the drug dispenser's actions when performing the final steps of provisioning.

In another embodiment, the camera is external to the dispensing device like a digital camera, a smartphone, a tablet, a laptop of some other external device. In one of these embodiments, once the external device takes the photo or video they could be uploaded to the dispensing device via Bluetooth, USB, NFC or some other communications means. In another embodiment, once the external device takes the photo or video it might be uploaded directly to the central database. The photo or video can be timestamped and identified by the patient identification and the dispensing device's identification. The goal of these embodiments is to acquire one or more photographs or videos in order to ensure that the actual drug consumer interacting with the dispensing device is ingesting their medication. The photograph also provides a historical record that the correct drug consumer is taking the drugs correctly. The photographic or video content can be uploaded to the central database, and a review can be performed by a recognition system or an authorized health care worker, drug prescribers drug dispensers or other authorized persons at any time during the drug consumption period.

In yet another embodiment, urinalysis information can be collected and used to determine whether the patient is taking their medication. Analyzing urine can provide different key indicators on a patient. In some embodiments, an external device is used and the results can be relayed through the dispensing device. The use of portable urinalysis devices with Bluetooth support is an example embodiment of an external device. In an embodiment the dispensing device can receive and analyze the urine sample directly. In other embodiments the external urinalysis device can talk directly with the central database. In this embodiment the urinalysis results are included with the patient identification and if necessary the dispensing device identification to ensure the central database logs the information with the correct patient.

As with other biomedical input, there are several embodiments for handling urinalysis results. In one embodiment before the dispensing device could be deployed by the drug dispenser to the drug consumer, they would provide a urinalysis result. This final step before deployment would be added to the provisioning of the biometric input. This would establish a baseline result for further urinalysis outputs to compare against to help the health care professional determine the effect of the medication on the patient. In other embodiments a baseline might not be required and perhaps only occasional urinalysis results are required by the drug consumer. In these embodiments the dosage rule file might indicate that the drug consumer must provide a urine sample just once a week to ensure the effects of the drugs being consumed are not harming the patient. In another embodiment a urine test strip is used and photographed by the drug consumer after consumer drugs. This photograph might then be uploaded to the central database either directly or through the dispensing device.

In other embodiments the biomedical input could be related to a blood analysis, to a heart monitor analysis, EKG, EEG, saliva analysis, a breath analysis or some other biomedical test directly involving the drug consumer. In all these tests a baseline can be taken from drug consumer and relayed to the central database. In some embodiments an external device is used and the information is relayed to the dispensing device using USB, Bluetooth, WiFi, NFC or some communication method. In another embodiment the external device can communicate directly with the central database and provide the patient identification and if necessary the dispensing device identification. In yet other embodiments, the dispensing device is customized with internal hardware and software to analyze blood samples, receive heart monitor results, receive breath analysis results and other results and pass them to the central database directly.

To reinforce the central database's authority and control over the dispensing device, it alone can send the Start Deployment and Stop Deployment command to the dispensing device. It can perform these actions only after receiving the Provisioned Stage Reached message from the dispensing device. In other embodiments there could be protection for the drug consumer should a biometric input problem take place. If a drug consumer become panicked about their drugs, they might be able to call a professional who can immediate force a dose of medication from the central database to the drug watchdog.

Turning now to FIG. 1 there is an illustration 100 of a network overview showing drug prescribers 104 and drug dispensers 112. The drug prescriber 104 is a licensed professional who can write prescriptions for drug consumers 106. They might be working in many possible locations 102, like doctor's offices, hospitals, clinics, emergency departments or similar health care locations. These professionals 104 could be a nurse practitioner, a dentist, a pharmacist, a physician or any other person who is authorized to issue prescriptions. In some embodiments, especially in environments like a dentist's office, paper prescriptions are often used 108.

In other embodiments prescriptions are written out on computers 140 either within the drug prescriptions office using a Electronic Management System (EMS) or externally on another remote system. In some embodiments, a central database 124 used, which has a series of processors 130 providing an interface 132 to one more datum storage solutions 134. Such hosted systems can offer many features including accessing from any location, storage backup and recovery of data to avoid catastrophic loss.

In other embodiments, the drug prescriber 104 might use an e-Prescribing Authority to create and store prescriptions for drug consumers 106. In this embodiment these prescriptions may or may not be handed to the drug consumer 106 to hand-carry to a drug dispenser 112. The computer 140, 114 could be a desktop computer, a laptop computer, a tablet computer, a smartphone or any computer system capable of allowing input of prescription information through a specialized application or through a web browser. In some embodiments the computer 140, 114 opens a connection over a data communication pathway 120 over one or more networks 122, 144 to specialized health care focused computers 124, 138 and in some embodiments to government agencies to deal and track all prescriptions that are created. In Canada for example the PrescribeIT™ system 138 has been established to improve the safety and trackability of prescriptions.

Following different embodiments the traditional prescription information will be included into a larger set of data called the dosage rule file 136. Since each step of a prescription's creation and fulfillment carry essential information this information will form parts of the dosage rule file 136. The system allows the drug prescriber 104 to participate in the computerization and increase safety created by using the central database 124, 138. In those embodiments where the drug prescriber 104 uses a computer 140 to build their prescription it will be placed along side a larger set of usage and dosage information for the drug consumer 106. In some embodiments the computer 140 connects to a regional or national e-prescribing service 138 like PrescribeIT™ in Canada. When both the drug prescriber 104 and drug dispenser 112 use a common e-prescription service 138 the overall prescription system is considered safer. In these embodiments the central database 124 can communicate 150 with the e-prescribing service 138 to acquire prescription information for a drug consumer 106. For example, Canada's PrescribeIT™ system offers a REST (Representational State Transfer) API for the sole purpose of allowing EMS and Pharmacy Management Software (PMS) integration options to the national prescription registry.

In this application prescriptions are filled by drug dispensers 112. These same individuals are also involved with the provisioning of the dispensing device 126, 128, 142. Drug dispensers 112 are tasked with the responsibility of completing the dosage rule file 136 related to the drugs 116 they are dispensing. Drug dispensers 112 could be doctors, pharmacists, dentists, emergency medical technicians (EMT), home care aides, midwives, nurses or any other individuals who are authorized to fill prescriptions. Their intention is to ensure that drug prescriptions are followed precisely, for the safety by the drug consumers 106. The central database 124 can also be referred to as the central server 124 (with hardware processor and non-transitory memory).

Embodiments described herein relate to a computer implemented method of securing and tracking a dispensing device 126, 128, 142 and a dosage rule file 136 using a central server 124 and a drug watchdog program running on the dispensing device 126, 128, 142. The method can involve at a central server having a hardware processor with an interface 132 and a non-transitory memory storing the database 124, authorizing a login using the hardware processor to match credentials of the user against the database 124 of records for authorized users stored in the non-transitory memory and receiving dispensing device identification for the dispensing device 126, 128, 142 for storage in the non-transitory memory. The method can involve generating a dosage rule file 136 by receiving input data at the interface 132 from the authorized user and encoding at least drug consumption information, identification of the drug consumer, and additional authorized users into machine readable instructions for a drug watchdog program. The dosage rule file 136 can encode operating parameters for the dispensing devices 126, 128, 142 (and related dispensing equipment). The method can involve identifying a destination dispensing device 126, 128, 142 to receive the dosage rule file 136 using the hardware processor to access the dispensing device identification in the non-transitory memory. The method can involve establishing a secure communication link to encrypt messages exchanged with the dispensing device 126, 128, 142 with encryption keys to confirm the identification information of the dispensing device 126, 128, 142. The method can involve transmitting, using the secure link, the dosage rule file 136 to the destination dispensing device 126, 128, 142. The destination dispensing device 126, 128, 142 can have a hardware processor and a non-transitory memory storing the drug watchdog program and the dosage rule file 136. The destination dispensing device 126, 128, 142 can execute the dosage rule file 136 and the drug watchdog program using the hardware processor to access the non-transitory memory, and upon execution, the drug watchdog program continuously running on the destination dispensing device The destination dispensing device 126, 128, 142 can and reading the dosage rule file to: open a compartment of dispensing equipment to receive drugs matching the drug consumption information in the dosage rule file 136. The destination dispensing device 126, 128, 142 can detect closure of the compartment and drug provisioning of the dispensing device; upon authorizing bio-identity input, send a provisioned stage reached message to the central server 124 to program the processor to a provisioned stage. The destination dispensing device 126, 128, 142 can receive a begin deployment command from the central database to program the processor to a deployment stage of the dispensing device 126, 128, 142; activate timers upon deployment on the dispensing device 126, 128, 142 to control release of the drugs contained in the compartment for the drug consumer; and encrypt messages using the encryption keys; and send the encrypted drug consumption messages for decryption by all authorized users to the central server 124 upon expiration of at least one of the timers.

In some embodiments, the method involves at the central server, providing the interface 132 to receive the input from the authorized user to generate the completed dosage rule file 136. In some embodiments, the method involves detecting a connection from a selected dispensing device 126, 128, 142 to a user's computer system; providing, to the authorized drug dispenser, the interface 132 on the central server in order to generate the completed dosage rule file 136. Upon detecting the finishing of the completed dosage rule file 136, using the selected dispensing device's identification received from the dispensing device 126, 128, 142 through its connection to the user's computer, to establish the secure channel to encrypt all messages exchanged between the dispensing device 126, 128, 142 and the central server 124 or database 124, and transmitting the completed dosage rule file 136 to enable the provisioning of the dispensing device 126, 128, 142.

In some embodiments, the method involves at the destination dispensing device 126, 128, 142 running the drug watchdog program, establishing a secure data communication path with the central server 124 by using the dispensing device's identification to select encryption keys; and receiving an indication from the central server over the secure data communication path that the dosage rule file is ready for transmission to the destination dispensing device, the completed dosage rule file encrypted using encryption keys linked to the dispensing device identification.

In some embodiments, the method involves, at the destination dispensing device 126, 128, 142, establishing a secure communication link between the compartment and the hardware processor for data exchange, opening the compartment by sending control messages to the compartment over the secure communication link. The compartment of the dispensing device can be separate from the hardware processor of the dispensing device.

In some embodiments, the method involves identifying the destination dispensing device 126, 128, 142 as having dispensing equipment separate from the hardware processor of the dispensing device 126, 128, 142 running the drug watchdog program. The dispensing equipment having the compartment, and encoding an identifier for the drug dispensing equipment in the dosage rule file.

In some embodiments, the opening of the compartment requires a confirming status message from the central server 124 to instruct the drug watchdog to perform an unlock procedure.

In some embodiments, the method involves, at the central server 124, allowing multiple dispensing devices 126, 128, 142 to be in a provisioned stage, and sending a begin deployment command to only one dispensing device 126, 128, 142 assigned to the same drug consumer at a time.

In some embodiments, the method involves, at the central server 124, detecting that a deployed dispensing device 126, 128, 142 has run out of drugs and sending a begin deployment command to the next provisioned dispensing device 126, 128, 142 for the same drug consumer.

Embodiments described herein relate to a computer implemented method of securing and tracking a dispensing device 126, 128, 142 and a dosage rule file 136 by an authorized drug dispenser using one or more central servers 124 for managing dispensing devices and a drug watchdog program running on the dispensing device 126, 128, 142. The method involves: at a hardware processor coupled to a non-transitory memory storing a prescription database of authorized users, authorizing a login using the hardware processor matching the credentials of the user against the prescription database of authorized users stored in the non-transitory memory to create an authorized drug dispenser. The method can involve searching by the authorized drug dispenser for prescription information using the hardware processor to access the prescription database stored in the non-transitory memory, the authorized drug dispenser linked to a drug consumer's identity; creating a dosage rule file encoding the prescription information, the drug consumer's identity, drug consumption information and additional authorized users for the dispensing device into machine readable instructions for the drug watchdog program that can be downloaded to the dispensing device 126, 128, 142. The method can involve establishing a secure data communication path with the central server 124 used for managing dispensing devices, by using the hardware processor to determine identification of the dispensing device to select encryption keys; encrypting the dosage rule file using encryption keys linked to the dispensing device identification. The method can involve exchanging with the central server 124 over the secure communication path the dosage rule file. The dispensing device 126, 128, 142 having a hardware processor and a non-transitory memory can store the drug watchdog program and the dosage rule file, and execute the dosage rule file 136 and the drug watchdog program using the hardware processor to access the non-transitory memory. Upon execution, the drug watchdog program continuously running on the dispensing device 126, 128, 142 and reading the dosage rule file 136 to: open a compartment of dispensing equipment to allow drugs to be inserted matching the drug consumption information in the dosage rule file 136. The dispensing device 126, 128, 142 can detect closure of the compartment and drug provisioning of the dispensing device. Upon authorizing bio-identity input from the drug consumer, the dispensing device 126, 128, 142 can send a confirmation message to the central server 124 to enter a provisioned stage. The dispensing device 126, 128, 142 can receive a begin deployment command from the central server that commences the deployment stage, and activate timers upon deployment on the dispensing device to allow the controlled release of the drugs contained in the compartment. The dispensing device 126, 128, 142 can send drug consumption messages and alert messages for decryption by all authorized users, using the selected encryption keys to the central database 124 when the timer expires.

In some embodiments, creating the dosage rule file 136 involves moving the prescription information from the prescription database to the central server 124 that is used for managing dispensing devices. In some embodiments, opening of the compartment requires a confirming status message from the central server informing the drug watchdog to perform an unlock procedure. In some embodiments, the expiration of the activated drug dose timers to allow the release of a drug dose, also includes one or more indications including modifying the display of LED lights, displaying a message on a screen, the playing of auditory sounds and the sending one or more message to the drug consumer using a configured communication method.

In some embodiments, an alert message transmitted from the dispensing device 126, 128, 142 to the central server 124 is relayed from the central server to the drug consumer using one or more configured communication methods.

In some embodiments, an alert message within the dispensing device 126, 128, 142 is sent directly to the drug consumer's computer device using one or more configured communication methods.

In some embodiments, the decryption of messages by all authorized users further includes the ability for one of the authorized users to modify the dosage rule file.

In some embodiments, the method involves, at the destination dispensing device 126, 128, 142, establishing a secure communication link between the compartment and the hardware processor for data exchange, opening the compartment by sending control messages to the compartment of the dispensing device over the secure communication link. The compartment of the dispensing device 126, 128, 142 is separate from the hardware processor of the dispensing device 126, 128, 142.

In some embodiments, the method involves identifying the destination dispensing device 126, 128, 142 as having drug dispensing equipment separate from the hardware processor of the dispensing device running the drug watchdog program, the drug dispensing equipment comprising the compartment, and encoding an identifier for the drug dispensing equipment in the dosage rule file.

Embodiments described herein relate to a computer system for securing and tracking a dispensing device 126, 128, 142 and a dosage rule file 136. The system can involve a central server 124 having a hardware processor with an interface and a non-transitory memory storing a database, the interface 132 to generate and provide a completed dosage rule file encoding at least a drug consumer's identity, drug consumption information and authorized users for a dispensing device into machine readable instructions for the drug watchdog program, the completed dosage rule file encrypted using encryption keys linked to the dispensing device identification. The system has a dispensing device 126, 128, 142 having a hardware processor and a non-transitory memory storing drug watchdog program running on the dispensing device 126, 128, 142, the hardware processor executing the drug watchdog program. Upon execution, the drug watchdog program continuously running on the destination dispensing device to: establish a secure data communication path with the central server 124 by using the dispensing device's identification to create an encrypted channel; verify that at least one authorized user is in possession of the identified dispensing device 126, 128, 142 by changing the state of the dispensing device 126, 128, 142 and requiring the authorized user to verify that state; receive an indication from the central server 124 within the received status message over the secure communication path that the completed dosage rule file is ready for download after the authorized user is verified. The dispensing device 126, 128, 142 exchanges the completed dosage rule file with the central server 124 to enable the provisioning of the dispensing device. The hardware processor executes the completed dosage rule file and upon execution, the drug watchdog program reading the dosage rule file to: open a compartment of dispensing equipment to allow drugs to be inserted matching the drug consumption information in the dosage rule file; detect closure of the compartment and drug provisioning of the dispensing device. Upon authorizing a biometric input from a drug consumer, the dispensing device 126, 128, 142 sends a confirmation message to the central server 124 to enter a provisioned stage of the dispensing device dispensing device 126, 128, 142 and receive a begin deployment command from the central server 124 that commences the deployment stage of the dispensing device. dispensing device 126, 128, 142. The dispensing device 126, 128, 142 activates timers upon deployment on the dispensing device 126, 128, 142 to allow the controlled release of the drugs contained in the compartment. The dispensing device 126, 128, 142 can send drug consumption messages for viewing by all authorized users, using the selected encryption keys to the central server when the timer expires.

In some embodiments, the destination dispensing device 126, 128, 142 establishes a secure communication link between the dispensing equipment and the hardware processor for data exchange to open the compartment by sending control messages. The dispensing equipment can be separate from the hardware processor running the watch dog program.

The drugs 116 within the dispensing device 126, 128, 142 could be in a physical form, a liquid form, a vapour form or some combination, for example a liquid that is expelled as a vapour. There are many electronic insulin pump devices 128 that allow a separately worn arm band to feed real-time information to the pump device 128 for patient dosing. Such a device can be guided by a dosage rule file that is managed by a drug watchdog. Similarly, digital electronic inhaling devices 126 exist that can benefit from a managed dosage rule file that sets limits on how much a patient can use the inhaler 126 and the medication it contains. Further devices could include IV machines, electronically controlled Peripherally Inserted Central Catheter (PICC) type devices and other advanced medical dispensing devices.

Various forms of dosage rule files 136 are downloaded to match the type of dispensing devices 126, 128, 142 being used with the drug consumer 106. Amounts, quantities and measures are designed by the system to match specific methods used to measure and insert the drugs 116 into the dispensing devices 126, 128, 142.

In those embodiments where the drug watchdog program is running on another computer system, the drug dispenser 112 might first verify the drug consumer 106 has the necessary drug dispensing application on that computer system. The drug dispenser 112 might had the drug consumer 112 a wearable lanyard, or a drug dispensing wand or even verify a drug dispensing App is loaded on their smartphone. In these embodiments the central database 124 is given the contact information for communicating with the drug watchdog. The drug watchdog must then validate that it is in communication with the correct drug dispensing equipment 126, 128, 142.

As mentioned, there are times that prescriptions can be filled by doctors within their offices, especially in very small communities or when free samples are available. Depending on the environment and country many other names could be used for these individuals. Drug dispensers 112 might be located in many possible locations 110. They could be in a hospital, in a pharmacy, at a person's home, in an emergency department, in a doctor's office or anywhere where drugs 116 are kept for physical distribution.

There are several embodiments for drug prescribers 104, drug dispensers 112 and dispensing devices to communicate to the one or more networks 122, 144. In some embodiments the drug prescriber 104, drug dispenser 112 and dispensing device 126, 128, 142 are connected 120 to a network 122, 144 that is capable of reaching the same central database 124, 138. In other embodiments, it is possible the drug dispenser 112 must communicate to both an e-Prescribing Authority 138 first and then finish the provisioning and deployment of the dispensing device 126, 128, 142 on the central database 124.

They might be on the same network 122, or on different networks like Network A 122, and Network B 144 that can reach the same computer system 124, 138. In some embodiments a wireless network, like Network B 144 goes through a public network Network A 122, like the Internet to reach the central database 124 or e-Prescribing Authority 138. In other embodiments the computer 130 running the central database 124 might have multiple connections 120 to different networks 122, 144. In some embodiments the network 122 is a publicly available network like the Internet. In other embodiments it could be a closed private network within a hospital. The common central database 124 is used to manage the dispensing devices 126, 128, 142, control dosage rule files 136 and collect all tracking information when deployed. Drug prescriber 104 and drug dispenser 112 have different choices as to how they participate with the central database 134 in the creation of the dosage rule file 136 and the viewing of tracking information provided by the dispensing device 142.

To facilitate the involvement of the drug prescriber 104 and drug dispenser 112 a user-friendly interface 132 is provided to the central database 134 for inputting the drug consumers' 106 prescription and for locating a drug consumers' 106 prescription. In some embodiments drug prescribers use Electronic Medical Record (EMR) software to manage patients and build prescriptions. Many of these EMR software systems are capable work working with external e-prescription services. Similarly, in some embodiments drug dispensers use a Pharmacy Management Software (PMS) product to manage their business. Many of these EMS systems are capable of working with external e-prescription services. These user friendly, business software solutions are built for extensibility and have application program interfaces (APIs) to enable extension to support a solution like a drug tracking dispensing device described in this patent.

Connections from client computer systems 112, 126, 128, 140, 142 to the serving computer system 124, 138 can use many different wired and wireless networks and network protocols. Above the physical connections to wired 122 and wireless networks 144 many embodiments use standard Internet protocols, like a transport control protocol and Internet protocol (TCP/IP), hyper-text transfer protocol (HTTP) and secure HTTP to facilitate the communication necessary to work with the central database 124 and e-Prescribing Authority 138.

To provide a user interface (UI) for the drug prescriber 104 and drug dispenser 112, 112, 140 might use an Internet capable browser to facilitate the interface into the central server's database system 132. The UI can be used to create and modify parameters of the dosage rule file. The central database 124 might be a cloud-computer offering which facilitates access to a data storage area 134 available in a wide geographic region. In this embodiment a secure communication protocol like secure socket layer (SSL) would be used to create a secure link to the central database storage 134. Such storage is where the dosage rule file 136 is created and exchanged with the dispensing device 126, 128, 142.

In other embodiments custom protocols and programs are used to create a secure communication path to the central database 124. Communications methods for the dispensing devices 126, 128, 142 could also involve both wired and wireless connections. In some embodiments the dispensing device 126, 128, 142 may also support local connections 146 to the drug dispenser's computer 114. Connections 146 like universal serial bus (USB), and short-range Bluetooth, could allow for a secure connection safely within the drug dispenser's facility 110. As mentioned in other embodiments the connections from client computer systems 112, 126, 128, 140, 142 might go to an e-prescribing cloud server 138. Interconnections 150 from this e-prescribing system 138 to the central database 124 would be accomplished through computer-to-computer communications 150 using message exchanges following formats like JSON over HTTP or HTTPS.

Figure 2:
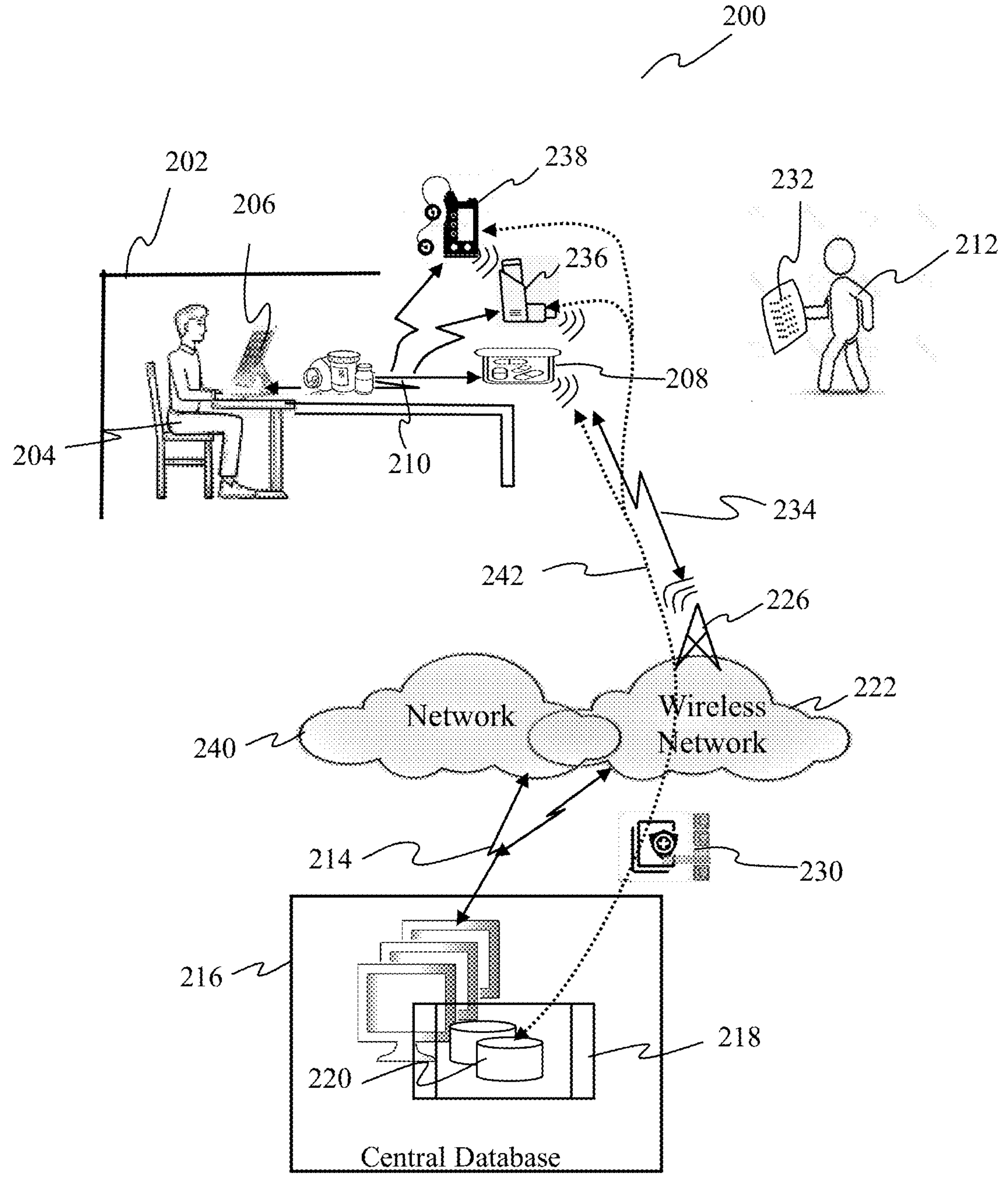
FIG. 2 shows an embodiment of a network overview showing the use of a tamper-proof dispensing device in a wireless network.
Figure 3:
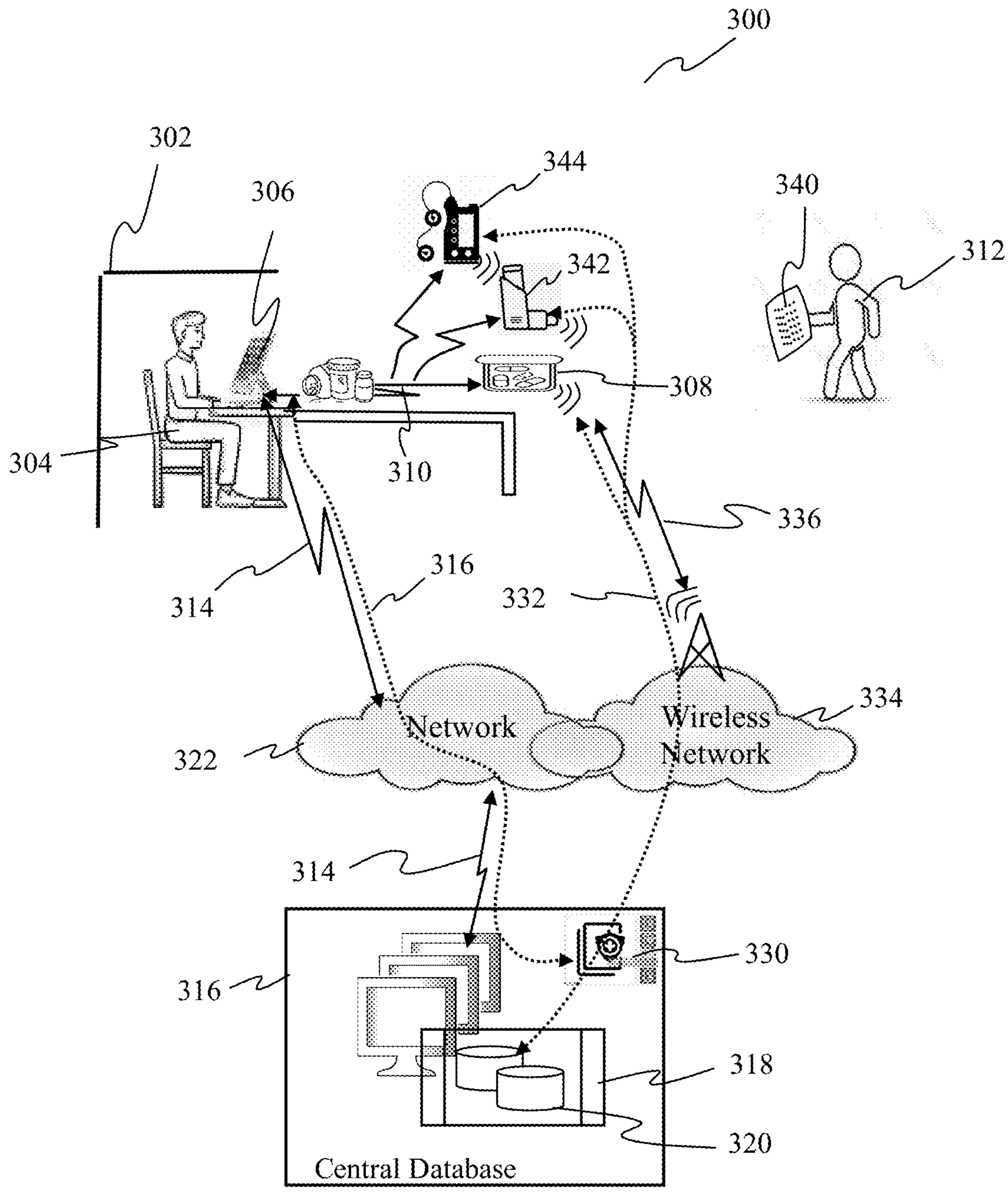
FIG. 3 shows another embodiment of a network overview showing the use of a tamper-proof dispensing device.

The different embodiments for creating the dosage rule file 136 and working with the dispensing device 126, 128, 142 are highlighted in FIGS. 2 and 3. The focus is creation of the dosage rule file 136 and the different ways the drug prescriber 108 and drug dispenser 112 can participate.

When a drug consumer 106 visits a drug prescriber 104 in their facility 102, the drug prescriber 104 has two choices. In one embodiment they are willing and able to use the central database 124 or an e-prescribing service 138. In another embodiment they are not initial able to use the central database 124 or e-prescribing service 138.

In those embodiments where the drug prescriber 108 can login into the central database 124 or e-prescribing service 138 they are authorized initially through licensing boards and professional bodies and are matched to licensed practitioners through name, identification, association certificates, addresses and/or other specified information when they create their login and password profiles. Once connected and through the authorization stage, the drug prescriber 104 is then able to start the process of creating a dosage rule file 136 for a drug consumer 106.

The drug consumer's 106 identification is also required with the dosage rule file 136 to ensure accurate accessing of the correct dosage rule file 136 by the drug dispenser 112. Once the dosage rule file 136 is entered into the central database 124 the drug consumer 106 can go to a licensed drug dispenser 112 to have their dosage rule file 136 loaded into a dispensing device 126, 128, 142. The drug dispenser 112 must use their computer 114 to access the central database 124 in order to locate the drug consumer's 106 dosage rule file 136 as entered by the drug prescriber 104. In some embodiments the drug dispenser 112 must first locate the prescription information on the e-Prescribing Authority 138 and request it through the central database 124 over the secure communications link 150.

Once the drug consumer 106 identifies themselves, the drug dispenser 112 can proceed to load the dosage rule file 136 into a specialized dispensing device. Once the dosage rule file 136 is loaded the dispensing device 126, 128, 142 will open. Once the drugs 116 are loaded and the dispensing device 126, 128, 142 is closed the dispensing device 126, 128, 142 enters the final stage of provisioning. With the dispensing device 126, 128, 142 selected and the drug 116 loaded, the drug consumer 106 provides a bio-identity and biomedical information to the dispensing device 126, 128, 142 so the dispensing device 126, 128, 142 can enter the provisioned stage.

Once in the full provisioned stage the central database 124 decides when to issue the begin deployment command. Once in deployment, the drug consumer 106 can receive their daily drugs 116 by proving their biometric before being allowed to remove the drugs 116. In some embodiments the biometric that has already been taken by the drug prescriber 104 may be used along with biomedical data for the dispensing process. This dispensing device is the focus of FIG. 4 which follows.

In some embodiments the drug consumer 106 is only allowed to possess one dispensing device 126, 128, 142 and the central database 124 will block the provisioning process if multiple dispensing devices 126, 128, 142 attempt to provision the same drug consumer 106 with the exact same drug 116. In other embodiments the central database 124 allows multiple dispensing devices 126, 128, 142 to be given to the same drug consumer 106 with the exact same drug 116. In this case the goal is to provide the drug consumer 106 a continuous supply of drugs 116 so they do not accidently run out which could cause a life and death situation in some cases. In this embodiment the central database 124 knows precisely when the last dose is extracted from a given dispensing device 126, 128, 142, and will issue the begin deploy command to a second dispensing device 126, 128, 142 when additional drugs 116 are needed. This is referred to as the hot-swap method of continuous drug 116 supply.

In some embodiments the drug prescriber 104 is not able to use the central database 124 to help initially build the dosage rule file 136. In these embodiments an alternative prescription method is used with the drug consumer 106. In some embodiments this will result in the drug consumer 106 hand-carrying a copy of the prescription to the drug dispenser 112. However, it is possible for the drug dispenser 112 to grant access to the drug prescriber 104 after they have completed the provisioning and deployment steps for the drug consumer 106 and a dispensing device 126, 128, 142. This secure access to the central database 124 will allow the drug prescriber 104 to review the dosage rule file 136 and tracking message for the drug prescriber 104 once the dispensing device 126, 128, 142 is provisioned and deployed in the field. These embodiments are further explored in FIGS. 2 and 3.

Turning to FIG. 2 there is an embodiment of a network overview 200 showing the use of a dispensing device 208, 236, 238, in a wireless network 222. In many embodiments the process starts as the drug consumer 212 enters a drug dispensing location 202 holding their prescription 232 in hand. In other embodiments the drug consumer 212 might be helped by a health-care professional 204, one of their children 204 or a spouse 204 to prepare and load the dispensing device 208, 236, 238.

The dispensing location 202 is capable of working with a dispensing device 208, 236, 238 that is needed to hold the prescription drugs being requested by the drug consumer 212. In some embodiments, these are high-risk drugs that are considered very addictive. In some embodiment they have restrictions placed on their use by governments, insurance companies or drug manufacturers.

In some embodiments the dispensing activity can take place in the same location where the drug prescriber first created the prescription 232. The drug consumer 212 interacts with the drug dispenser 204 in order to acquire the prescribed drugs within a dispensing device 208, 236, 238. In these embodiments the drug consumer 232 is carrying a formal prescription in their hand, making it clear to the drug dispenser 204 that it has not been created by the central database 216 and that a dosage rule file 230 does not yet exist. In these embodiments the drug prescriber has not worked with a compatible e-prescribing system that requires the drug dispenser 204 to complete, as described in FIG. 1. In this illustration the drug dispenser 204 is working alone to help support, protect and ensure better patient 212 outcomes. They can, in the process of creating the dosage rule file 230, add additional health care workers and support staff, including doctors, pharmacists, nurses, on-call assistance and others to help track progress and review feedback messages from the dispensing device 208, 236, 238.

There are several embodiments where a non-licensed person 204 can assists the drug consumer 212 to make use of the dispensing device 208. This person 204 is acting as a proxy for the drug dispenser, in some cases picking up the drugs on behalf of the drug consumer 212 and inserts them into the dispensing device 208, 236, 238. They might have power of attorney (POA), they might have POA for personal care or might be a spouse or loved one with a desire to improve the drug consumer's 212 drug consumption outcome.

In this embodiment the owner 204 of the dispensing device 208 can login into the dispensing device 208 and create a dosage rule file 230 by directly communicating 210 to the dispensing device 208, 236, 238. The steps of creating the dosage rule file 230 are always required in order to provision and deploy the dispensing device 208, 236, 238 and insert the necessary drugs. This could take place in an old age home, a hospital, a patient's 212 home or any location where a computer 206 is available.

In this embodiment the drug consumer 212 is carrying a formal prescription 232, so the drug dispenser 204 has several options to fill the prescription 232. In this embodiment the drug dispenser 204 simply connects 210 a dispensing device 208, 236, 238 to their computer 206 and begins to work directly on creating a dosage rule file 230. The process of connecting an operational and supported dispensing device 208, 236, 238 to their computer 206 creates the beginning of an authenticated relationship to the dispensing device 208, 236, 238. As mentioned, this connection could be over USB, Bluetooth, near field communications (NFC) or some other close-proximity method. The drug dispensing 204 might also use a laptop, tablet or cell phone computer to interface to the dispensing device 208, 236, 238. The goal is to ensure the dispensing device 208, 236, 238 has an authenticated connection 210 to a drug dispenser's 204 computer 206 and no other computer 206 in the vicinity. In some embodiments once connected 210 the drug dispenser 204 might use an Internet browser and an HTTP visual interface to prepare the dosage rule file 230 or in other embodiments they might use a custom program design specifically to work only with these custom build dispensing devices 208, 236, 238.

Before the drug dispenser 204 can start building the dosage rule file 230 and filling the drug dispenser 204 with drugs, they must create a login process. Creating or validating an existing login represents the second step in the authentication stage. This step will ensure that only they can access this dispensing device 208 in future. Creating a new login and password combination can only take place on a dispensing device 208, 236, 238 that has never been used before or that is empty and in an idle, unused state. It is possible that when a given dispensing device 208, 236, 238 has completed its dosing requirements for one drug consumer 212, it could be de-provisioned and given to another drug consumer 212. It could be rented, sold or exchanged between different drug dispensers 204 as needed when it has been de-provisioned.

At no time should other individual be allowed to gain access to the dispensing device 208, 236, 238 to adjust the drug dosage or change any part of the dosage rule file 230. There are several embodiments for the login procedure when gaining access to a dispensing device 208, 236, 238. If the dispensing device 208, 236, 238 has been used before and still contains some number of unused drugs, the drug dispenser 204 will have to use the previous login process already established. If the dispensing device 208, 236, 238 is empty or has never been used before the drug dispenser 204 can just from the beginning to create a new login process. In one embodiment the login process is both a login name and a password. In another embodiment the login process is simply a password or access code for the dispensing device 208, 236, 238.

Once the login process is created the drug dispenser 204 can commence the provisioning of the drug dispenser 208 by building a dosage rule file 230 . . . . The dosage rule file 230 includes details from the prescription 232 information and required information about the drug consumer 212. For example, information components could be a drug consumers 212 identification, health card identification, biomedical requirements, photographic evidence of the drug consumer 212 and operating details for the dispensing device 208, 236, 238.

Once this information is collected, it can be entered through the interface provided by the drug watchdog running on the dispensing device 208, 236, 238 to build the dosage rule file 230. An example of the contents of the dosage rule file have been shown earlier in this application. In this embodiment the addition of the passwords for the drug prescriber, drug dispenser and other health support workers are very important as they get delivered and used by the central database 216 later. Then at a later date when the dispensing device 208, 236, 238 has been provisioned and deployed any of these people will be able to log into the central database 216 and review how the drug consumer 212 is doing with their drug consumption.

In some embodiments the login and password might provide different levels of access and visibility to the dosage rule file 230. For example, the drug prescriber will be able to change the dosage values in the dosage rule file 230 and request it be uploaded back into the dispensing device 208, 236, 238. The drug dispenser 204 will only be able to change the number of pills added to the dispensing device 208, 236, 238 before it is uploaded back into the dispensing device 208, 236, 238. There are cases where the drug consumer 212 has reached the very end of their prescription and only a portion of drugs remain in their prescription 232. Finally, the other health support workers might only be able to see the tracking information provided by the dispensing device 208 after it is provisioned and deployed in the field.

Once the dosage rule file 230 is complete and uploaded to the central database 216, they are reviewed within the data storage area 220 via a user interface (UI) 218, or using advanced computer logic to compare patients, drugs and dispensing devices 208, 236, 238. Checks can be made to allow for different drug dispensing strategies and restrictions. For example. In one embodiment the central database 216 has logic to ensure a drug consumer 212 does not already have a dispensing device 208, 236, 238 assigned to them and dispensing the same drug already. In another embodiment the drug consumer 212 would be allowed to have multiple dispensing devices 208, 236, 238 and only one has been placed into deployed mode by the central database 216. This hot-swap method could be used to ensure a continuous supply of medication is already on hand for very high-risk drug consumers 212.

When the dispensing device 208, 236, 238 is first turned on and connected 210 to a local computer it establishes a link 242 to the central database 216 over a wireless network 222. Base station 226 support and coverage allow for a mobile and portable dispensing device 208, 236, 238 to allow the drug consumer 212 to travel and move around with their drugs.

The central database 216 performs a check on the dispensing device's 208, 236, 238 state to ensure it is known and available for use. It then sends the final all clear to proceed message, the dispensing device 208, 236, 238 will then proceed with login, authorization and the first step of provisioning, which is to create the dosage rule file 230. After the dosage rule file 230 is complete the dispensing device 208, 236, 238 can be opened.

Once the dispensing device 208 is opened, the next part of the provisioning process takes place when the drugs are finally loaded and the dispensing device 208, 236, 238 is closed. With the drug loaded and the dispensing device 208, 236, 238 closed, the final step in provisioning involving the collection and validation of the bio-identity.

Provisioning of the bio-identity requires the drug consumer 212 to provide a bio-identity to the dispensing device 208, 236, 238 to receive their regular dosage of drugs. The bio-identity will include a biometric to access the dispensing device 208, 236, 238 for every dose and might also include biomedical data. As discussed, biomedical data might be required to allows the drug consumer 212 to receive their next dose of their drugs, or in other embodiments it might be needed periodically. In some embodiments the biometric could be a fingerprint, retina scan, heart rhythm or some other unique property that is inherent to the drug consumer 212. In other embodiments the drug consumer 212 could have a sub-dermal implant that provides a unique identification held only by that person 212. Many other embodiments are possible including facial recognition, vein scan and other bio-centric techniques. With such a close relationship between the dispensing device 208, 236, 238 and the drug consumer 212 changing to a different dispensing device 208, 236, 238 does require some steps.

In some embodiments the dispensing device 208 has malfunctioned and just needs to be swapped for a new one. The drug consumer 212 would have to re-visit the drug dispenser 204 to facilitate this. In other embodiments the drug consumer 212 needs a completely different drug and must visit the drug prescriber to make that change. This would then have to be followed by a trip back to the drug dispenser 204 to remove the drugs from their current dispensing device 208, 236, 238 and insert new drugs into the same dispensing device 208, 236, 238 or in some embodiments into a new dispensing device 208, 236, 238. The central database 216 keeps track of all drugs held within the changed dispensing device 208, 236, 238 and the drug dispenser 204 will be told they must return all removed drugs, especially high-risk drugs back to the manufacturer to be destroyed.

Once deployment has taken place, the dispensing device 208, 236, 238 uses its connection 234 to the wireless network 222 to send secure messages 242 to the central database 216. Each of the encrypted messages sent will provide the identity of the dispensing device 208, 236, 238. Since the dosage rule file 230 was already sent during the provisioning stage, the central database 216 has used some of the contents to build authorization login and passwords for drug prescribers, drug dispensers 204 and other health care professions. These added authorized accesses will allow these individuals to look at data for this drug consumer 212 on this specific dispensing device 208, 236, 238 on the central database 216 through the interface 218 provided by the central database 216. These messages will be encrypted using several possible embodiments for creating encryption keys and encrypting messages. The drug watchdog on the dispensing device 208, 236, 238 also encrypts any stored data in memory so that no tampering, copying, modification or malicious damage can take place unnoticed. The drug watchdog software monitors activities on the dosage rule file stored on the dispensing device. Modification or damage to any of the files will result in re-requesting the data from the central database 216.

Drug consumer 212 information can also be added to the dosage rule file 230 to allow for important alerts to be provided to the drug consumer 212. This might involve information about low drug levels, low power levels or other critical information.

Example methods of encryption could be used to negotiate and facilitate the extra protection required. For example, in some embodiments, public-key cryptography might be used. In this embodiment the central database 216 holds the public key for all deployed dispensing devices 208, 236, 238 that are manufactured to be part of the system. The manufacturer provides these public keys to the central database 216 as each dispensing device 208, 236, 238 is built, tested and entered into the system. The public key of the central database 216 is also installed into each dispensing device 208, 236, 238 in a tamper-proof memory. In another embodiment a seed value might be used to negotiate a shared symmetric key between the dispensing device 208, 236, 238 and the central database 216. The seed value might be extracted from the computer 206 connecting 210 the dispensing device 208, 236, 238 and the central database 216 for example. In another embodiment the seed value is a serial number of the dispensing device 208, 236, 238 that has also been provided to the central database 216. The seed value is used to negotiate a symmetric encryption key used to exchange information. Once a secure path 242 is created all messages and dosage rule file 230 can be uploaded to the central database 216.

As mentioned once the dosage rule file 230 is uploaded to the central database 216 the drug prescriber and drug dispenser 204 can review the information and change different parts of it if the drug consumer's 212 needs change. When the central database 216 places the dispensing device 208, 236, 238 into the deployment stage, the dispensing device 208, 236, 238 communicates status messages to the central database 216 on a regular basis. In some embodiments this communication occurs every time a drug is ejected to a drug consumer 212. In other embodiments this communication 242 could occur once a day or every other day. Different embodiments could be configurable and data communication failures at different times could result in cached messages that are saved until data communication paths 234 are re-established. All messages 242 use the negotiated encryption key to ensure that eavesdropping or manipulation of message is not possible.

Turning now to FIG. 3 there is another embodiment 300 of a network overview showing the use of a various dispensing devices 308, 342, 344. In some embodiments the process starts as the drug consumer 312 enters a location 302 that holds prescription drugs. In other embodiments the drug consumer 312 enters with an indication that the provisioning process has already been started by the drug prescriber. Therefore, there are several embodiments that can take place for the drug dispenser 304 as they meet this drug consumer 312.

For example, in one embodiment they could be carrying a paper prescription 340 indicating the drug prescriber has not logged into the central database 316 and started the process of preparing the dosage rule file 330. In another embodiment the drug consumer 312 arrives with a paper with prescription-like information 340 but it simply points to an identification code for the dosage rule file 330 on the central database 316. In another embodiment the drug consumer 312 arrives and just tells the drug dispenser 304 that they have a prescription waiting to be filled on a compatible national or regional e-prescribing service. This indicates to the drug dispenser 304 that the process of creating the dosage rule file 330 has been started. Unlike FIG. 2, in this figure the drug dispenser 304 will connect to the central database 316 or an e-prescribing service using one of several methods.

In FIG. 3 there is also the ability for a non-licensed person 304 to assist the drug consumer 312 when using the dispensing device 308, 342, 344. This person 304 is acting as a proxy for the drug dispenser by collecting the drugs on behalf of the drug consumer 312 and inserts them into the dispensing device 308, 342, 344. They might have power of attorney (POA), they might have POA for personal care or might be a spouse 304 or loved one 304. In these embodiments the owner 304 of the dispensing device 308, 342, 344 logins into the central database 316 and creates a dosage rule file 330 in order to provision the dispensing device 208 and insert the necessary drugs. This could take place in an old age home, a hospital, a patient's 212 home or any location where a computer 206 is available.

In one embodiment the drug dispenser 304 opens a connection 314 through a network 322 with the intention of logging into the central database 316. In one embodiment the drug dispenser 304 has created an authorized login at the central database 316 and is able to use its interface 318 to work with and update the dosage rule file 330. Once the drug dispenser 204 completes work on the dosage rule file 330 the central database 316, it can download the dosage rule file 330 to the correct dispensing device 308, 342, 344 using one of several possible embodiments.

In this embodiment, unlike the examples shown in FIG. 2, the drug watchdog on the dispensing device 308, 342, 344 does much less work with the drug dispenser 304 over the connection 310. In this embodiment, it just needs to receive the dosage rule file 330 not built one itself. In this embodiment the drug dispenser 304 creates a new login at the central database 318 and goes through a verification process to prove they are in possession of a known dispensing device 308, 342, 344. Once they identify the dispensing device 308, 342, 344 and verify they possess it, the dosage rule file 330 can be created and uploaded to the dispensing device 308, 342, 344. This is discussed later in this section.

There are several possible embodiments when either the drug prescriber or the drug dispenser 304 use a login authorized by an external accredited legal entity. In one embodiment an e-prescribing system like PrescribeIT™ in Canada is used to facilitate the online creation and management of prescriptions.

In another embodiment the central database 316 contains the legally authorization codes and confirmation identifiers to enable the authorization stage. In these embodiments various governing bodies for drug prescribers provide detailed information for all known and licensed drug prescribers in a given region or country. This confirms that a given set of drug prescribers are certified and authorized to prescribe drugs to the general public.

For example, in Canada a doctor might acquire their license to practice from the Medical Counsel of Canada. With this license comes a number and identification tracking mechanism. They can use this to create their authorized login and enter prescriptions into the central database 316. For drug dispensers 304 various governing bodies for drug dispenser's 304 provide detailed information for all known and licensed drug dispenser's 304 in a given region or country. This confirms that a given set of drug dispenser's 304 are certified and authorized to dispense drugs to the general public.

When an e-prescribing system is present the central database 316 uses a computer-to-computer method that employs an application program interface (API) to extract prescription information to create the dosage rule file 330. This was discussed in FIG. 1 in greater detail. For example, a system like PrescribeIT™ uses a Java Script Object Notation (JSON) API to facilitate pharmacy management software (PMS) systems 306 to interact with the data stored in the PrescribeIT system. In this embodiment there could be a two-step process. The first step would be to first locate the patient's prescription on the e-prescribing system and import it into central database 316 using several possible methods. The second step would be to augment that information with any other operation parameters required and securely download that information into the drug consumer's 312 dispensing device 308, 342, 344.

Once a drug prescriber is authorized, they can enter prescription information 340 into the central database 316 to begin building the dosage rule file. They can also print out some of this information 340 for the drug consumer 312 to carry to the drug dispenser 304. For the drug dispenser 304 once they have an authorized login to the central database 316, they can search for or create dosage rule files 330 to download into dispensing devices 308, 342, 344.

With an authorized login the drug dispenser 304 has the advantage of connecting 310 the dispensing device 308, 342, 344 or not connecting 310 the dispensing device 308, 342, 344. In the embodiment where they drug dispenser 304 does not connect the dispensing device 308, 342, 344, it is assumed the dispensing device 308, 342, 344 supports another connection 336 alternative like a cellular connection or a WiFi connection 336.

In other embodiments the drug dispenser 304 still connects 310 the dispensing device 308, 342, 344 into the computer 306 to reduce problems with out-of-coverage and loss-of-coverage type radio frequency (RF) issues. When the central database 316 has both wired and non-wired communications 314, 336 it provides maximum success and increased options to ensure the data intended for the dispensing device 308, 342, 344 reaches it as expected. This embodiment could be very helpful in remote communities where cellular coverage 336 is very spotty or non-existent. This embodiment might be very useful in communities that are sparsely served by public Internet access and only pharmacists and large businesses have such connections 314.

Another advantage for connecting 310 the dispensing device 308, 342, 344 to drug dispenser's 304 computer 306 is to create an authorization path to a known, authorized and approved dispensing device 308, 342, 344. In this advantage the central database 316 has not been provided all the information on every licensed drug prescriber and every licensed drug dispenser 304. In this embodiment the drug dispenser 304 connects 310 an authorized and known dispensing device 308, 342, 344 into their computer 306. Only with the dispensing device 308, 342, 344 connected and recognized by the central database 316 will they be able to create a login and password related to this specific dispensing device 308, 342, 344.

In this embodiment the drug dispenser 304 does not enter the identification of the dispenser device 308, 342, 344, as it is already connected and the central database 308, 342, 344 and is in communication 316 with the dispensing device 308, 342, 344. Part of the authorization process involves the central database 316 retrieving that information and assigned it to this drug dispenser 304, this login session and dosage rule file 330.

Once the drug dispenser 304 has logged in successfully to the central database 316 with or without a connected 310 dispensing device 308, 342, 344, they are have passed the authentication stage and are ready to work on the dosage rule file 330.

As discussed already in some embodiments an identified dispensing device 308, 342, 344 must be connected 310 before commencing to the provisioning stage. In some embodiments the dosage rule file 330 has already been partially created and saved at the central database 316 by an authorized and accredited drug prescriber. In this embodiment the drug dispenser 304 must locate the exact dosage rule file 330 for this specific drug consumer 312. In this embodiment the drug consumer 312 must then identify themselves uniquely to the drug dispenser 304 before they can be assigned a dosage rule file 330. This identification must match the partially created dosage rule file 330 created by the drug prescriber.

There are many possible embodiments to ensure an accurate match within the central database 316. In Canada this identification could be their health card number, a passport number, a driver's license or even a social insurance number (SIN). In the USA this could be a drug consumer's 312 social security number (SSN), a driver's license, a state issued identity card or even a passport number. In other countries other unique number-based or name-based identifiers could be used.

In some embodiments the drug consumer 312 is unable to produce the proper identification. This can happen for a number of reasons for example the drug consumer 312 might be homeless and does not possess reliable or accurate photo identification. In this embodiment the drug prescriber has the option of using the dispensing device 308, 342, 344 or a compatible biometric reader to take a biometric from the drug consumer 312 and uploading it to the central database 316 and associated to the dosage rule file 330. When this is done the drug prescriber can then use the drug consumer's 312 name as a stage one identification and the biometric must then be used for a stage two identification. This same biometric information must then be provided to the drug dispenser 304 to retrieve the dosage rule file 330 from the drug dispenser 304. In some countries a sub-dermal implant might be used to hold a unique identifier that acts like a quick RFID identification. Such systems use a form of RFID called near field communication (NFC) to energize and then identify the holder of the sub-dermal implant. These any other forms of identification are possible to confirm to the drug dispenser 304 that the drug consumer 312 standing in front of them is exactly who they claim to be.

Once the drug dispenser 304 receives a valid piece of identification from the drug consumer 312, they can connect 314 to the central database 316 to confirm the identity of the drug consumer 312 and to locate the dosage rule file 330 created for the drug consumer 312. In those embodiments where an identification is lacking the drug consumer's 312 name would be used initially to find the dosage rule file 330 but then a biometric would be needed next to confirm the dosage rule file 330 is for them. In this embodiment the connection 314 takes place through a network 322 that can reach the same central database 316 used by the drug prescriber when they created the dosage rule file 330. The interface 318 works in conjunction with the central database 316 to provide a user-friendly method to search and locate this information.

In another embodiment the drug prescriber has not connected to the central database 316 and there is no partial dosage rule file 330 to find. In this embodiment the drug dispenser 304 must input all the necessary fields using the prescription information 340 brought to them by the drug consumer 312. In many embodiments this decision might be obvious based on the type of prescription form 340 handed to the drug dispenser 304. In this embodiment additional information is entered by the drug dispenser 304, including password or access information for the drug prescriber and other health professionals. This will allow the drug prescriber to modify the dosage rule file 330 at a later time and allow everyone who has access to view the tracking information from this dispensing device 308, 342, 344 provide by the drug watchdog.

Once the dosage rule file 330 is located or created by the drug dispenser 304, it can be downloaded to the correct dispensing device 308, 342, 344. As already discussed in one embodiment the connection 310 to the drug dispenser's 304 computer 306 is used to facilitate this download. This could take place using a connection method 310 like a USB. In another embodiment a method like Bluetooth 310 or NFC 310 might be used. Other embodiments like Bluetooth 310 and NFC 310 might be more useful if the computer 306 is a tablet or smartphone was used in locating and downloading the dosage rule file 330.

In other embodiments the drug dispenser 304 has a dispensing device 308, 342, 344 and has not connected 310 it directly to their computer 306. In these embodiments the dosage rule file 330 is created on the central database 318 and is downloaded using a cellular connection 336. In this embodiment the dispensing device 308, 342, 344 is known (e.g. verified) by the central database 316 to support cellular communications 336 and so secure messages 332 are sent using this communications medium 336.

As already discussed in FIG. 2 the communication between the central database 316 and the dispensing device 308, 342, 344 is facilitated by negotiating an encryption key if one does not already exist. The many possible embodiments for this encryption have been detailed. In all embodiments it is assumed a shared encryption strategy is used between the central database 316 and the dispensing device 308, 342, 344. If an agile encryption strategy is used the central database 316 and the dispensing device 308, 342, 344 will use various embodiments to select which encryption algorithm to use dynamically for each message or for a given deployment period.

When the drug dispenser 304 does not connect 310 the dispensing device 308, 342, 344 to their computer 306, they must go through a verification process with the central database 318. This involves the drug dispenser 304 providing identification information identifying the dispensing device 308, 342, 344 they have in their possession. Once the identification of the dispensing device 308, 342, 344 is confirmed, an encrypted message 336 is sent to the dispensing device 308, 342, 344 over the wireless network 334 to change the state of the dispensing device 308, 342, 344.

In one embodiment this state change might involve illuminating a specific pattern on the LED lights. In another embodiment this state change might involve playing a series of auditory sounds in a pattern. In another embodiment a number, or a phrase could be displayed on a screen provided on the dispensing device 308, 342, 344. Once the state change takes place the drug dispenser 304 must confirm the state change on the central database 318 in order to confirm they are in possession of the correct dispensing device 308, 342, 344. In some embodiments this process could be repeated a few times verify the legitimacy of the drug dispenser 304 and their claims to be wanting to load drugs into a specific dispensing device 308, 342, 344. Once verified the drug dispenser 304 is considered authorized and can then start to build the dosage rule file 330 to start the provisioning process.

Once the dosage rule file 330 is complete it can be securely downloaded over the encrypted wireless channel 332, 316 to watchdog program embedded and running on the dispensing device 308, 342, 344. Before this takes place the dispensing device 308, 342, 344 sends one or more messages 316, 332 about its current status.

In one embodiment, when connected to the drug dispenser's computer 306, this information includes information available from the computer 306 being used to connect 310 to the dispensing device 308, 342, 344. This information will be saved and used to validate drug dispensing 302 locations. In other embodiments these messages will include the current physical contents of the dispensing device 308, 342, 344 and any other status information held by the dispensing device 308, 342, 344.

In some embodiments the dispensing device's 308, 342, 344 current status might not match the status being held by the central database 316. For example, in this embodiment there could be unsent status messages not yet received or processed by the central database 316. The current status would also provide details on the last dosage rule file 330 it contained if there was any. In these embodiments the number of remaining drugs within the dispensing device 308, 342, 344 would also be provided.

In some embodiments this will be the first time it has ever been used and so it has no current status. In some embodiments a status message will be provided that indicates a biometric is required from the drug consumer 312 before the dosage rule file 330 can be downloaded to the dispensing device 308, 342, 344.

The central database 302 also interacts with the drug watchdog to determine if the drug watchdog itself needs upgrading or changing. The drug watchdog within the dispensing device 308, 342, 344 runs along side the operating system (O/S) and any mechanisms used to eject drugs and detect forced entry. If the dispensing device 308, 342, 344 is ready for a new dosage rule file 330 the central database 316 sends the dosage rule file 330 to the drug watchdog running within the dispensing device 308, 342, 344.

With all checks performed between the central database 316 and the drug watchdog on the dispensing device 308, 342, 344 the dosage rule file 330 is downloaded 316, 332 over the selected channel 314, 336 depending on the embodiment. Once this is complete the main compartment of the dispensing device 308, 342, 344 can be opened and the drug dispenser 304 can insert the required drugs into the dispensing device 308, 342, 344.

In some embodiments once the dosage rule file 330 is successfully communicated 316, 332 to the drug watchdog, it automatically opens the receiving compartment on the dispensing device 308, 342, 344 in preparation for drugs to be inserted. In other embodiments the drug watchdog might activate a switch to relieve a locking mechanism so the main compartment can be physically opened by the drug dispenser 304. Once the drugs are inserted by the dispensing device 304 the compartment is closed and the dispensing device 308, 342, 344 can move to the final step of provisioning.

The final step of provisioning involves the collection and verification of the drug consumer's 312 bio-identity. To reach the fully provisioned stage, the drug consumer 312 must first provide a bio-identity input to the dispensing device 308, 342, 344.

As already discussed, the bio-identity will include a biometric input for retrieving every drug dose and potentially one or more biomedical inputs. After successful provisioning of the bio-identity input the dispensing device 308, 342, 344 enters the provisioned stage, which it communicates to the central database 316. Once in the provisioned stage the central database 316 has sole discretion when to begin the deployment phase, which begins the execution of the dosage rule file 330.

The drug consumer 312 now is in a position to consume the drugs within the dispensing device 308, 342, 344 following the exact instructions provided by the drug prescriber. As discussed, the drug consumer 312 will have to provide their bio-identity each time the they want to access the dispensing device 308, 342, 344 to take their next dose of drugs.

During this deployment state the dispensing device 308, 342, 344 communicates status messages to the central database 316 on a regular basis. In some embodiments this communication 316, 332 occurs every time a drug is ejected to a drug consumer 312. In some embodiments the drug consumer 312 might have to provide biomedical data every day to be approved for continued drug doses.

In other embodiments this communication 316, 336 could occur once a day or every other day. Different embodiments could be configurable and data communication failures at different times could result in cached messages that are saved until data communication paths 314, 336 are re-established.

All messages use the negotiated encryption key to ensure that eavesdropping or manipulation of message is not possible. In some embodiments the dispensing device 308, 342, 344 is equipped with cellular capabilities to communicate tracking and usage information in near real-time. In this embodiment one of several cellular OEM chipsets are used to provide 3G, 4G, LTE and WiFi (802.11) type communication options to the dispensing device 308, 342, 344.

In some embodiments these options are important when a drug consumer 312 takes the dispensing device 308, 342, 344 with them from the drug dispensing location 302. In these embodiments the drug consumer 312 may or may not have connectivity at home and in some cases they may be homeless. In other embodiments the dispensing device 308, 342, 344 uses just WiFi either in the drug consumer's 312 home, or at any public, open WiFi hotspot.

Since all messages over this communication path are encrypted the use of public, free Wifi hotspots is not a problem. In other embodiments the dispensing device 308, 342, 344 is plugged into the drug consumer's 312 computer at the end of the day for charging and any outstanding status messages are sent to the central database 316 at this time.

Figure 4:
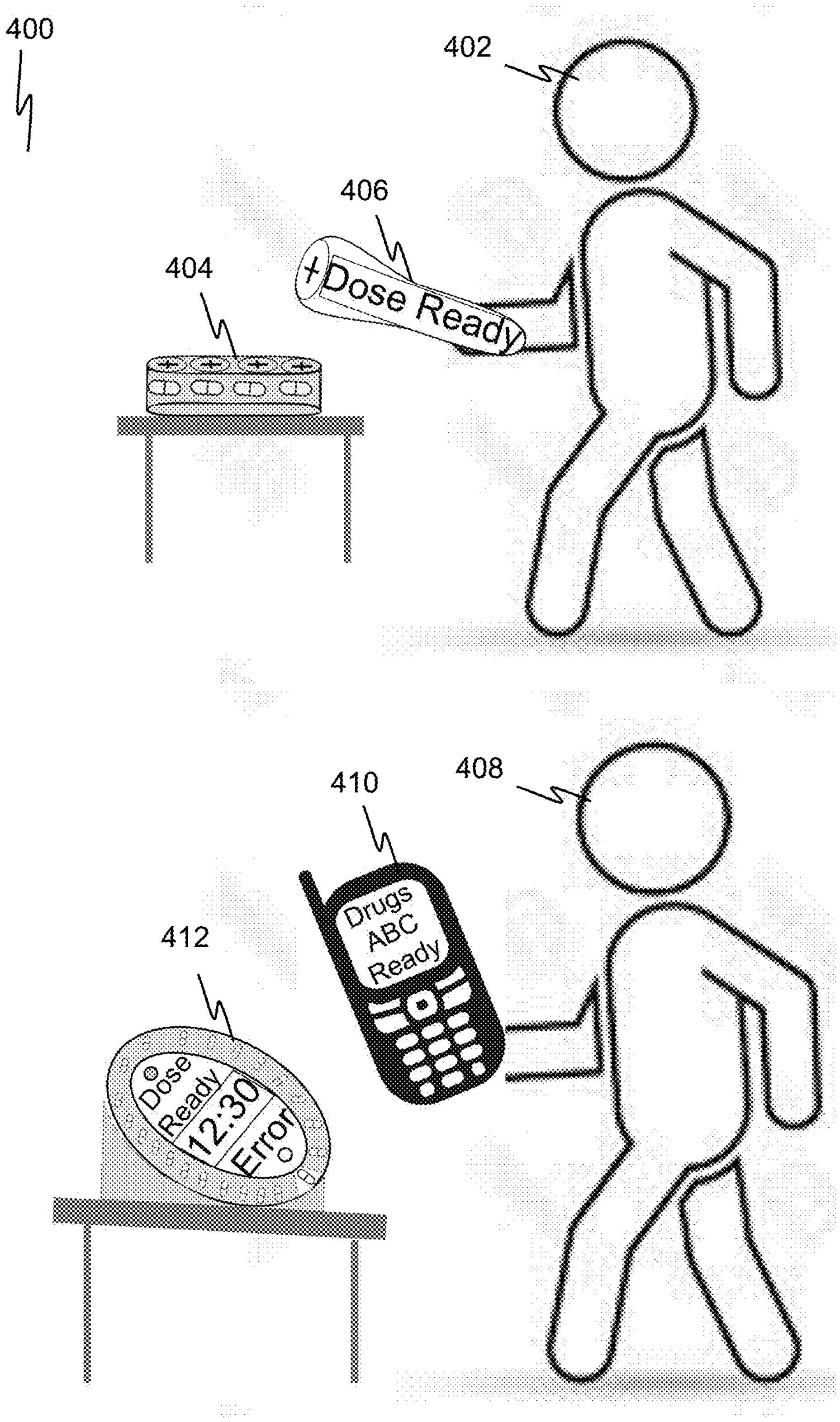
FIG. 4 is an illustration of two embodiments of the drug dispenser being used by a patient for accessing their drugs.

Turning now to FIG. 4 there is an illustration 400 of two embodiments of the drug dispenser being used by a patient for accessing their drugs. These two drug consumer examples 402, 408 show two embodiments where the drug watchdog runs on separate computers 406, 410 from the drug dispensing equipment 404, 412. The drug dispensing equipment 404, 412 can include a compartment for the drugs that has a transceiver to exchange data. The separate computers 406, 410 have hardware processors in communication with the drug dispensing equipment 404, 412 over communication link to exchange data and control commands. For example, separate computers 406, 410 have hardware processors in communication with the drug dispensing equipment 404, 412 to send a control command to open the compartment for the drugs. The drug dispensing equipment 404, 412 can send messages to the separate computers 406, 410 indicating closure of the compartment. The dosage rule file can encode identifiers for the drug dispensing equipment 404, 412. The separate computers 406, 410 with the dosage rule file can use the identifiers to exchange data and control commands. The separate computers 406, 410 can establish a secure communication link to the dispensing device equipment 404, 412 for data exchange to open the compartment by sending control messages, for example. The dispensing device equipment can be separate from a hardware processor running the watch dog program. The dispensing device equipment 404, 412 can also be referred to as dispensing equipment or drug dispensing equipment, for example.

The first embodiment the drug consumer 402 is given an electronic wand 406 that has a hardware processor that runs the drug watchdog software. The wand 406 has non-transitory memory storing the drug watchdog software. The wand 406 receives the drug consumer's 402 biometric information and communications with the central database. The drug watchdog running on the wand 406 is capable of cellular communications and receives the drug dosage file for execution. Before being given to the drug consumer 402, the drug dispenser forms a relationship between the wand 406 and the drug dispensing equipment 404 so that only this unique wand 406 is capable of opening and accessing drugs with the drug dispensing equipment 404.

In this embodiment the wand 406 also provides the user with visual and auditory prompts to take their drugs. It also informs them which slot should be opened and when and only the designated slot will open at the correct time after the drug consumer 402 verifies their identity through the one or more bio-identity requirements.

In other embodiments the wand 406 might be attached and only optionally removed by the drug consumer 402 in those situations where they are traveling around their building or two the grocery store or some specific outing.

To prepare the wand 406 for the drug consumer, the drug dispenser will assign the wand's unique identification 406 to this drug dispensing equipment 404 through the interface provided at the central database. Once the drug dispensing equipment 404 and a specific wand 406 are assigned to a patient, the wand 406 is given the dosage rule file and will work with that drug dispensing equipment 404 to dispense drugs for the drug consumer 402. Communication between the wand 406 and the drug dispensing equipment 404 can be over secure Bluetooth or secure NFC.

In those embodiments where the wand 406 and the drug dispensing equipment 404 are integrated and inseparable, only one identification is required when assigning it to the drug consumer 402.

The second patient shown 408 has downloaded the drug watchdog app to their cell phone 410 and intends to use this as their drug authorization and control center for extracting their drugs from the drug dispensing equipment 412. The biometric reader of the cell phone 410 can then be used by the drug watchdog to verify the drug consumer's 408 identity before releasing drugs. The display and notification systems of the cell phone 410 can also be used to remind the drug consumer 408 to follow their drug regimen.

The first step for the drug dispenser in this embodiment is to select the drug dispensing equipment 412 that is available and matches the type of drugs to be dispensed. The serial number or identification number of the drug dispensing equipment 412 is then assigned to the drug consumer 408 through the central database interface provided.

To prepare the cell phone app 410 to work with the drug dispensing equipment 412, the drug dispenser will provide a unique identification code through the interface of the drug watchdog app on the cell phone 410. This identification code can be generated by the central database and be temporary valid for the duration of the dispensing period, to allow the drug watchdog to register with the central database. The drug dispenser will also provide a private identification code of the selected drug dispensing equipment 412 through this same interface. This value is given out-of-band and is not transmitted through a data communications link. The identification code for the drug watchdog app 410 and the serial number for the drug dispensing equipment 412 are then assigned to the drug consumer 408 to create a secure and unbreakable relationship.

When connecting the drug watchdog app 410 then identifies itself to the central database to receive the dosage rule file and drug dispensing equipment 412 serial number. With both the serial number and the private identification code, the drug watchdog 410 can then connect security to the drug dispensing equipment 412. Using this method there is no chance of a man-in-the-middle attack of the connection process between the drug watchdog app 410, the drug dispensing equipment 412 and the central database.

The drug consumer can then use this drug watchdog 410 with other drug dispensing equipment (not shown) and follow the same process with a drug dispenser to create unbreakable bonds with many types of drug dispensing equipment. The drug watchdog 410 can then assign the drug consumer 408 to greater levels of drug adherence.

Figure 5:
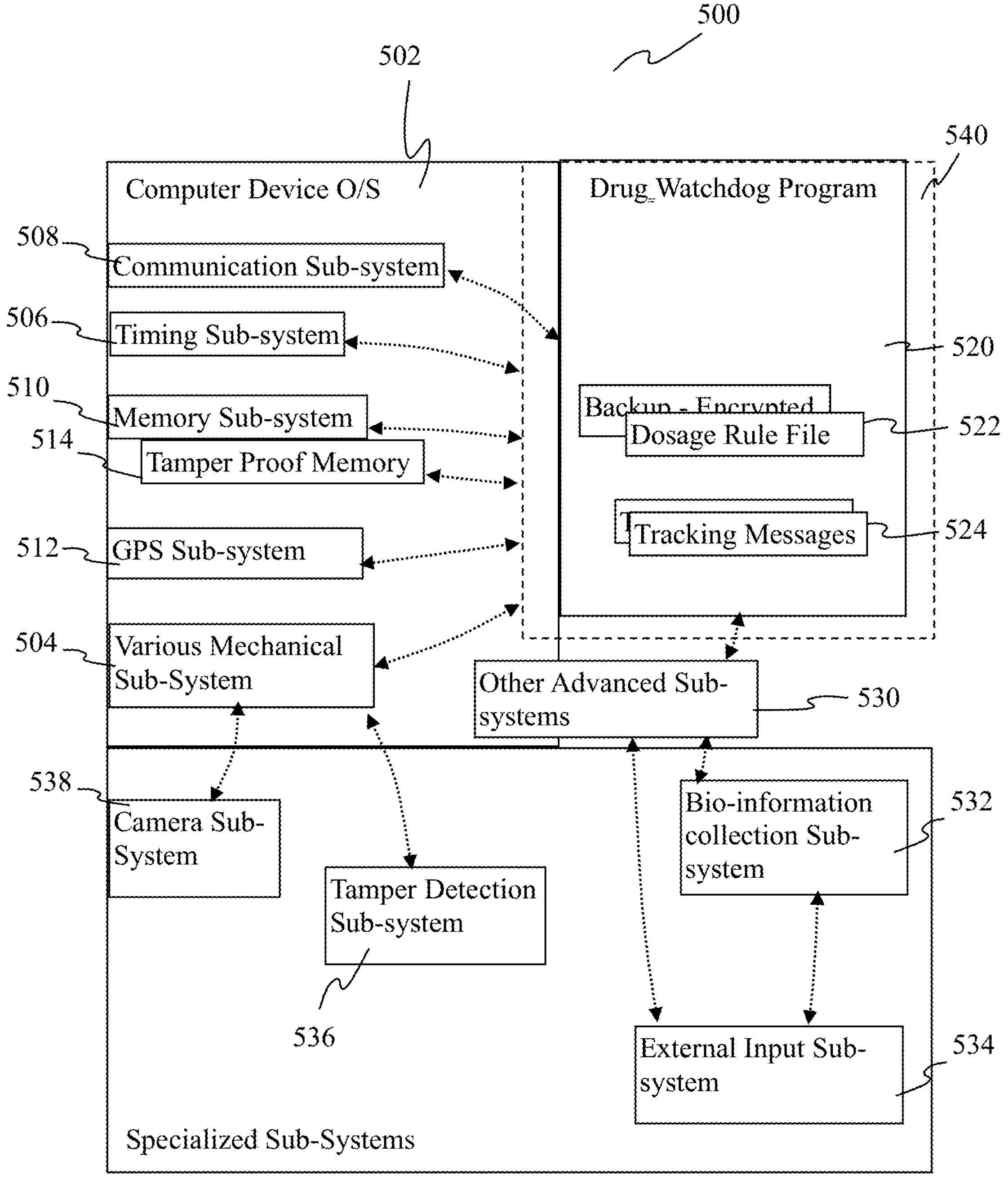
FIG. 5 is a more detailed illustration of a drug watchdog system within a drug dispensing system.

Turning now to FIG. 5 there is a more detailed illustration 500 of a drug watchdog program working within a drug dispensing system 500. In some drug dispensing system 500 embodiments, the drug watchdog program 520 is working within the same physical enclosure 540 as the drug dispensing equipment 502. In other drug dispensing system 500 embodiments, the drug watchdog program 520 communicates through the communication sub-system 508 of the drug dispensing equipment 502 to facilitate the extraction of drugs. In all embodiments the drug watchdog program 520 has control over the dosage rule file 522 and following the instructions within this file to determine who can open and access this file and how it is executed.

The drug dispensing equipment 502 is running a controller piece of software called a computer device O/S (operating system) in this illustration. In some embodiments this software could also be referred to as firmware on an embedded device. The O/S or firmware provides interfaces to a series of sub-systems available for use by one or more programs trying to control the drug dispensing equipment 502. In one embodiment these sub-systems could be reached using application program interface (API) calls. In other embodiments these sub-systems can be linked directly to programs loaded onto the drug dispensing equipment 502. The illustration 500 is provided as an example of one embodiment and other possible sub-systems could be included in other embodiments.

For example, within the mechanical sub-system 504 could be embedded sub-systems like a warning-light sub-system, timer display sub-systems and other sub-systems. This illustration shows just a few possible sub-systems, like the camera sub-system 538, the tamper-detection sub-system 536, the bio-information collection sub-system 532 and its related external input sub-system 534. These and many other specialized features might be present when the drug dispensing equipment 502 is designed and manufactured. There could also be auditory sub-systems for making sounds and a display to display various messages to the drug consumer. Another example could include an accelerometer sub-system, when a given printed circuit board (PCB) includes an accelerometer chip. In the other advanced sub-systems there could be a camera or some other video-capable equipment. Further there could be heartbeat monitors, blood analysis mechanisms or even urinalysis equipment built into the drug dispensing equipment 502. Many other possible enhancements could be included depending on the needs and design goals of the drug dispensing system 500.

The first sub-system listed is the communication sub-system 508. This sub-system would be used to delivery tracking messages 524 and sending or receiving the dosage rule file 522. There have been many possible communication methods discussed for this sub-system 508, include USB, Bluetooth, Ethernet and cellular communications. This sub-system 508 might support just one or many of these types of communication methods for the dispensing device. A sub-system includes computer hardware devices, such as hardware processors and non-transitory memory.

In some embodiments the communication sub-system 508 is used to securely communicate with the drug watchdog program 520 to facilitate the various mechanical sub-systems 504 to dispense drugs. In other embodiments the drug dispensing equipment 502 might have its own biometric sub-system 532 that might be activated and controlled by commands from the drug watchdog program 520.

The communication sub-system 508 is also used to negotiate the encryption key with the central database. The next sub-system illustrated is the timing sub-system 506. The timing sub-system 506 might allow for programs to set timer alarms and be notified when the timer expires. Such timers are often used to indicate the passage of time. Each time the timer sub-system 506 indicates it is time for another drug dose the drug watchdog 520 will go to the bio-identification sub-system 532 to get a biometric confirmation of the accessing person's identity before allowing them to become the drug consumer. Further use of the bio-identification sub-system 532 is possible for biomedical inputs following the dosage rule file's 522 configuration The memory sub-system 510 is the next sub-system shown and is used to store and retrieve information which is local to the drug dispensing equipment 502. When the drug watchdog program 520 is running within the drug dispensing equipment 502, the memory sub-system 510 will be an encrypted back-up copy of the dosage rule file 522, should the drug dispensing equipment 502 fail or have a re-boot occur. The current encryption key would also be saved in a tamper-proof section of the memory sub-system 514. Such tamper-proof memory chips 514 are common on smartcards and other advanced circuits and are often referred to as secure enclave processors 514. The tamper-proof memory sub-system 514 can also be used to store tracking messages 524, encryption keys and other data that needs the highest level of security.

The next sub-system is the GPS sub-system 512 which would be used to retrieve the current GPS co-ordinates on the globe. In some embodiments the drug watchdog 520 uses the GPS co-ordinates in every message to provide real-time tracking of a drug consumer and their whereabouts.

The next sub-system is collection of mechanical sub-systems 504 that could include a camera sub-system 538, a tamper-detection sub-system 536 and many others. In this illustration, the tamper detection sub-system 536 would be used to detect any attempts to forcibly open or break the drug dispensing equipment 502 to steal drugs out.

The mechanical sub-system 504 would be designed to provide control to physically moving parts, LED, auditory and display sub-systems within the drug dispensing equipment 502. Different embodiments might require the movement of a lock to allow the dispensing of a single dose of medication for example. Other embodiments might also involve the opening of a lid to fill the drug dispensing equipment 502 with a full prescription of drugs. At different times the mechanical sub-system is used to illuminate one or more LED lights to inform the drug consumer of a specific state. This might include many different states, for example when to consume drugs, when the power is low, or when wireless coverage is poor to name just a few important state changes.

In the other advanced sub-system 530 two sub-systems are illustrated. First is the bio-identification sub-system 532, which is used to accept bio-identification from a drug consumer using one of many possible methods. In some embodiments the bio-identity sub-system 532 is running in a separate physical housing, like in a cell phone running the drug watchdog 520. In other embodiments the bio-identity sub-system 532 is separate from both the drug dispensing equipment 502 and the drug watchdog program 520 and the communication sub-system 508 must be used to communicate with it.

Embedded bio-identity methods and types could vary between drug dispensing equipment 502, depending on the design and chip set used within the PCB, the type of bio-identity needed for different drugs and drug consumers. In some embodiments the bio-identity sub-system 532 might also include both biometric input and biomedical input options. In some cases, a specialized link to an external input sub-system 534 might be included to collect data from the user. This could include EKG monitors, blood pressure readings, heart rhythms detectors and many other.

Once installed and configured with the correct security information the drug watchdog program 520 communicates with the O/S or firmware running within the drug dispensing equipment 502. The drug watchdog program 520 provides oversight to the operation of the drug dispensing equipment 502.

The drug dispensing equipment's 502 basic operation starts and ends as controlled by the drug watchdog program 520. Broadly speaking, it informs the user when their next pill is required and at the push of a button dispenses the drugs required. The drug watchdog program 520 also creates a tamper-proof and secure environment where a dosage rule file 522 can be securely downloaded and stored in the memory sub-system 510, such that it can't be changed, modified or damaged without being detected.

Another goal of the drug watchdog program 520 is to provide tracking messages 524 for a range of situations and events. These tracking messages might indicate each time a drug is dispensed from the drug dispensing equipment 502 for the drug consumer. In those embodiments where the drug watchdog program 520 is running in a separate computer, these messages are related through the communication sub-system 508 to the drug watchdog program 520 for delivery to the central database. Other messages could indicate if someone is trying to break into the drug dispensing equipment 502. When available, messages about current location from the GPS sub-system 512 would be valuable to understand where the dangerous drugs are, especially in the case where the drug consumer misses a dose and could be in distress or if the dispenser has been stolen.

The drug watchdog program 520 also uses the bio-identification sub-system 532 within the advanced sub-systems 530 section to first memorize the identity of the current drug consumer using a biometric input. The current dosage rule file 522 will be received and targeted to the needs of this specific drug consumer.

When first provisioned by a drug dispenser the drug watchdog 520 might use the mechanical sub-system 504 to open the main door so the entire prescription of drugs can be inserted into the drug dispensing equipment 502. Once initiated the drug watchdog 520 would make use of the timing sub-system 506 to know precisely when the next dose should be dispensed out of the drug dispensing equipment 502. In some embodiments a LED sub-system might be presented to allow the drug watchdog to illuminate a light to tell the user their dosage time has been reached.

There are many other algorithmic procedures that are possible with the sub-systems and computers involved in a drug dispensing system 500 as described. For example if the tamper detection sub-system 516 sends an alarm to the drug watchdog 520 this might trigger the drug dispensing equipment 502 to never open again (until it is re-programmed by the drug dispenser) and to send an immediate message to the central database warning of the intrusion. In another embodiment the drug dispensing equipment 502 might include a terminate drugs sub-system. In this embodiment the drug watchdog 520 might send a message to this sub-system resulting in the release of a liquid substance into the main drug container. The liquid substance would then cause the destruction of all the drugs contained within it so that no unauthorized access would be possible.

There are many other possible sub-systems that could be present to perform advanced functions 530. In one embodiment there is a sub-system 534 to interact with a wearable device that detects whether the drug has been consumed and ingested by the drug consumer. The chemical reaction caused by the drug consumer's stomach acids on the chemicals creates a detectable signal. This signal is then passed through the advanced sub-system component 530 to the drug watchdog program 520 to allow for the next dose of drugs to be ejected. There are many other embodiments possible with the addition of hardware and software components.

Figure 6:
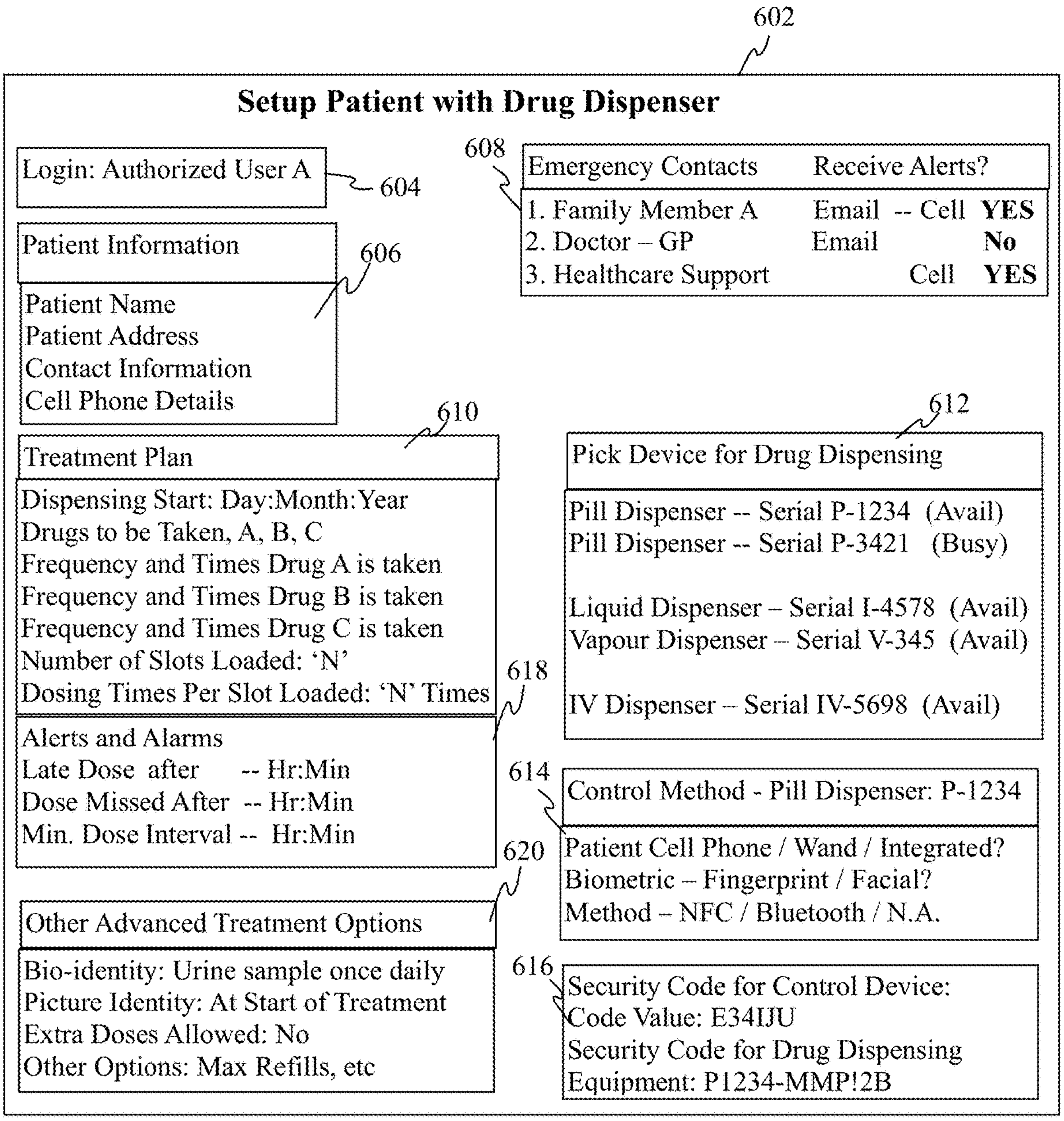
FIG. 6 is one embodiment of a user interface for an authorized user to set up a dispensing device for a patient needing prescription drugs.

Turning to FIG. 6 there is one embodiment of a user interface 602 for an authorized user to set up a dispensing device for a patient needing prescription drugs. There are many possible embodiments for a User Interface (UI) 602 to allow a drug prescriber and a drug dispenser to prepare and complete the assignment of a dispensing device a drug consumer. This illustration 602 represents a simplified single view of a configuration screen that explains the process in general for the drug dispenser. It is not meant to limit in any way all the myriad of other alternative visual approaches and alternative configuration settings that would be possible. The interface 602 can be used to create or modify the dosage rule file encoding the dosage information for controlling the dispensing device (and related dispensing equipment). The dosage rule file can include identifiers for the dispensing device and related dispensing equipment. For example, the dispensing device and dispensing equipment may be separate components and the dosage rule file can indicate an identifier for the dispensing device and dispensing equipment, and can also include communication data to establish a secure communication path, protocols, and message exchange data.

In this example screen the authorized user has logged in and authenticated themselves with the system 604. This might be a doctor, a pharmacist or even a loved one or caregiver wanting to set up the dispensing device for the drug consumer. The patient information 606 section can be very extensive or relatively straightforward. In some cases the information about the patient might come from a Pharmacy Management System (PMS) or an Electronic Medical Records (EMR) system. In other embodiments the information might come from prescription information held at a central prescription database like PrescribeIT™ in Canada.

With the patient selected 606, the authorized user can enter any emergency contacts 608 in this example. There could be family members, doctors, pharmacists, specialists, healthcare professionals, nurses and nursing-home support workers to name a few 608. In this example with each contact a cell phone or email contact could be provided. With this information the authorized user can set up one or more of the contacts to receive alert information 608 should the dispensing device trigger an alert. For example, if a drug dose is late to be consumed, or is late, a dispensing device is running low of drugs or running out of battery life an alert could be sent to many people.

The authorized user can then enter treatment plan information 610 for this patient 606. For this example, a drug dispensing start date is provided to tell the dispensing system when to commence the dispensing program. A list of the drugs to be taken are provided along with their frequency 610.

The dispensing device and/or related dispensing equipment can be referred to as a dispensing machine in some example embodiments. If additional specific times are provided each dispensing slot within the dispensing machine can have a very exact time when it is required to make the dose available for the patient. These times would be based on the number of total slots that are loaded, current shown as 'N' slots 610.

The treatment plan can also include advanced settings for the alerts and alarms that are generated for this patient 618. For example, a dose might be considered late after a certain number of hours and minutes. Similarly, a missed dose might be considered after so many hours and minutes. A minimum dose interval might be added to ensure the patient does not accidently take two doses too close to each other 618.

Finally in the treatment plan could be other advanced treatment options 620. These might include certain parameters that are used less frequent and in some cases for specialized drugs or patients. For example, if the drug being taken is a high-risk opioid then additional bio-identity check or photographic evidence might be requested. In other examples, the drug could be experimental, like a new cancel treatment. In this case perhaps a specialized urine sample is needed once a day to verify the side-effects of the drug on the patient 620.

Once the treatment plan is selected the authorized user can pick a dispensing device to assign to the patient 612. There are many potential embodiments for this section. In this example different types of drug dispensers are listed for the authorized user to pick from. Their status is shown and in other embodiments perhaps only available drug dispensing devices are listed.

Once a dispensing device is selected, additional control information can be verified from the authorized user 614. This might include selecting whether the system uses a cell phone, wand or is full integrated 614. With the control method selected, the type of biometric supported by that method can be determined and required by the drug watchdog program 614. The last step shown in this example is the selection of the communication method between the drug watchdog program to the drug dispensing equipment can be selected as well 614. If an integrated system is used then this would be not applicable (N.A.)

Depending on control method 614, additional security values and codes might be needed 616. If a separate control device is used to run the drug watchdog program, like a cell phone, a code value can be generated by the central database and manually entered into the control device being used. Since all drug dispensing equipment is registered with the central database, a code value for this equipment can be presented by UI to the authorized user to provided to the drug watchdog program 616.

Figure 7:
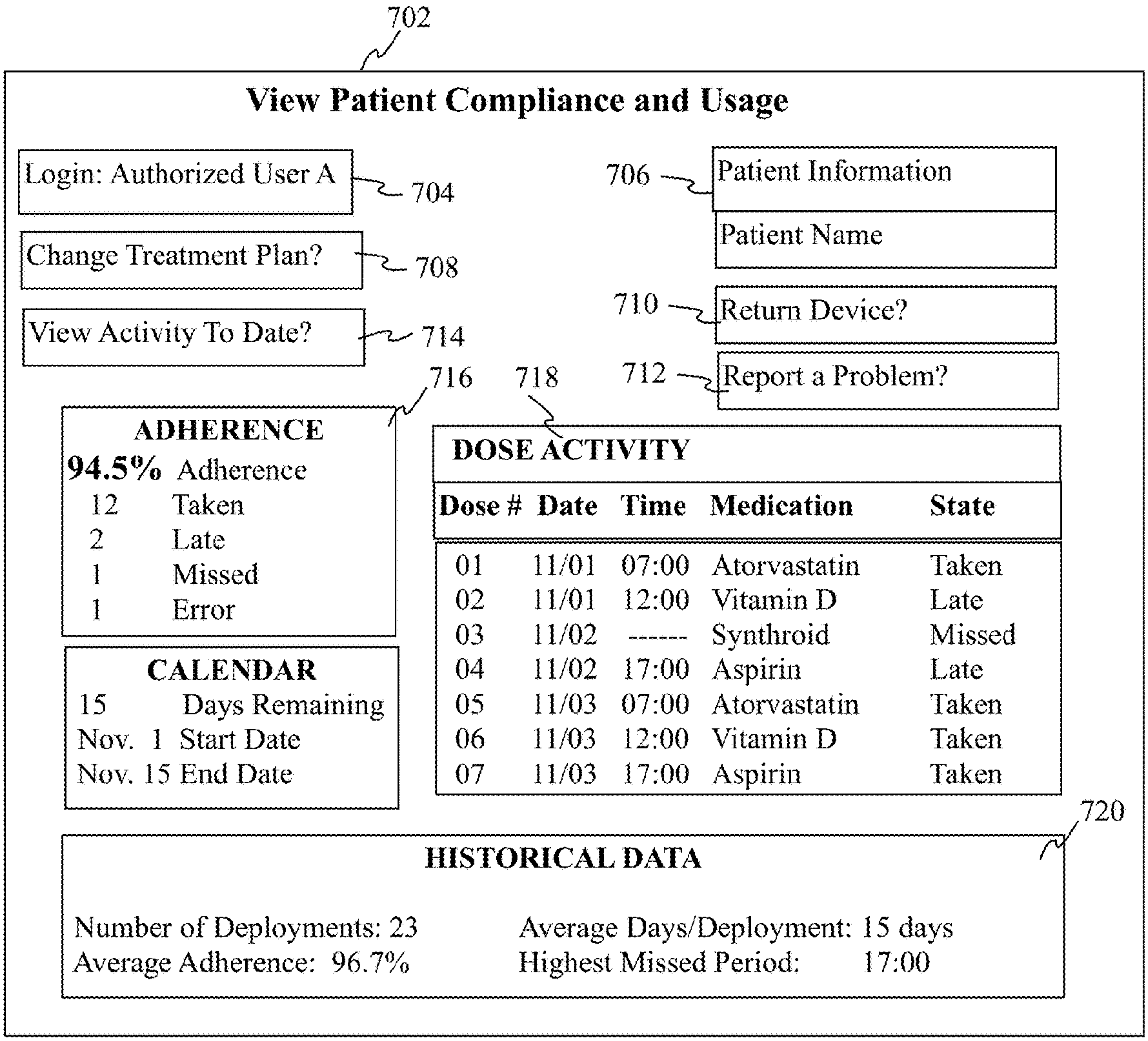
FIG. 7 is one embodiment of a user interface for an authorized user to view patient compliance and usage information for an assigned dispensing device.

Turning to FIG. 7 there is one embodiment of a user interface 702 for an authorized user to view patient compliance and usage information for an assigned dispensing device. There are many possible embodiments for a User Interface (UI) 702 to show an authorized user detailed information and statistics about how a drug consumer is progressing with their drug treatment plan. This illustration 702 represents a simplified single view of message summary screen that depicts a sub-set of all information, current and historical that would be possible. It is not meant to limit in any way all the myriad of other alternative visual approaches and alternative advanced graphic presentation methods that would be possible.

The interface 702 can be used for viewing patient compliance and usage information, and also to allow adjustment of dosage parameters in the dosage rule file.

The interface 702 can be used to create or modify the dosage rule file encoding the dosage information for controlling the dispensing device (and related dispensing equipment) and to view a variety of feedback information provided by the dispensing device and related dispensing device equipment. The interface 702 displays data collected during the secure monitoring of the dispensing device and related dispensing device equipment.

Once logged into the system the authorized user 704 can navigate over to the patient compliance and usage screen 702. First, they will have to pick a patient to review and look at 706. This will bring up their treatment summary information, statistical and historical data. They might be able to perform some actions on the dispensing device 710. The two example actions shown are to return the device 710 or to report a problem with a device 712. Other actions could include forcing a dose to be expelled immediately for the patient, request the biometric be reacquired from the patient and many other actions.

The authorized user 704 might then be given an opportunity to change configurable elements of the treatment plan 708. This might include the time certain drugs are released, the limits on late doses or missed doses and other soft-based configuration settings. Without the dispensing device in hand, they are not able to change the physical elements of the system, for example the number or types of drugs contained in a certain dispensing slot.

The compliance and usage screen 702 might have various adherence displays and statistical numbers for the authorized user 716, 718. In this example, the adherence shows a 94.5% adherence level with 12 doses taken to date, 2 late doses and 1 missed dose 716. The dosing activity is presented as well 718, showing the exact action of each dose slot, time it was released and whether it was missed and has no extraction time 718.

Figure 8:
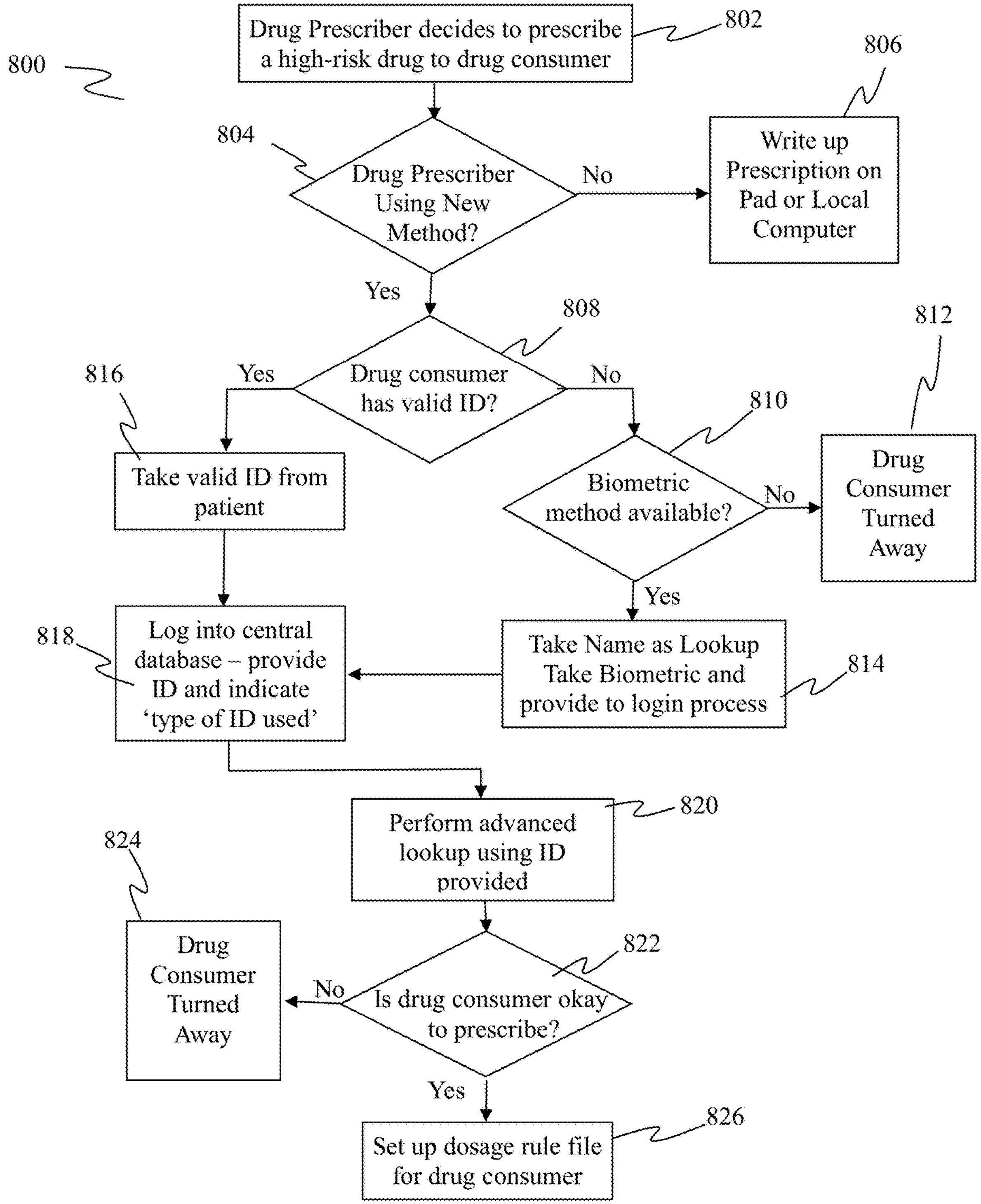
FIG. 8 a dataflow diagram of one embodiment for a drug prescriber to set up a dosage rule file.

Finally, the authorized user might be able to view historical data 720 that shows the patient's overall adherence percentage over many deployments of the dispensing system 720. This example the patient has achieved a 96.7 percentile of adherence with an average deployment of 15 days per dispensing device. It also looks across all data to determine that the highest missed dosing period is 5 μm in the evening. This example is but one of many possible embodiments of what could be presented with all the historical data collected in the system. Turning now to FIG. 8 there is a dataflow diagram 800 of one embodiment for a drug prescriber to set up a dosage rule file. The drug prescriber receives the drug consumer and after examination and discussions decides that the patient could benefit from a high-risk prescription 802.

First the drug prescriber must decide if they are going to use their original prescription method or the newer prescription method using a central database described in this patent 804. In some embodiments this could be related to whether the drug prescriber considers the drug high risk enough to bother with the more elaborate steps involved with working with the central database.

In other embodiments they are not up to speed on newer prescription methods for high risk medications. If they are not going to use the newer method, the drug prescriber writes up the prescription on their traditional customized prescription pad or on their local computer system 806. In some embodiments they might also have a remote prescription computer site they are already working with to prepare prescriptions 806. Advanced e-prescribing solutions like PrescribeIT™ are starting to be used by more and more doctor's offices. This choice will lead the drug consumer to hand-carry their prescription to a drug dispenser to be filled or perhaps present a document indicating they have an e-prescription started.

Alternatively, the drug prescriber is willing and able to work with the new prescribing method for high risk drugs. The first step is for the drug prescriber to request valid identification from the drug consumer 808. If the drug consumer does not have a valid piece of identification, then a specialized biometric method could be used 810. If the biometric is not available, the drug consumer will have to be turned away 812. They might go to a more advanced drug prescriber, a hospital or an advanced clinic where they can use their biometric. In other embodiments they will be faced with acquiring the proper identification of themselves.

If the biometric method is available 814, the name of the drug consumer is taken and used as the primary lookup 814. At the same time the biometric of the drug consumer is also taken 814. In some embodiments a dispensing device is given to the drug prescriber for the sole purpose of capturing biometric. In other embodiments a biometric reader, which is compatible with the dispensing device is used to collect the information. The device that is used is attached to the drug prescriber's computer where it captures and transmits the biometric over the link to the computer. The computer program or browser available to the drug prescriber holds this and uploads it when requested after the login stage. The biometric might be a fingerprint, a facial scan, a palm deep vein scan or some other type of biometric. In other embodiments the drug consumer, especially if they are homeless and without photo identification, might have a sub-dermal implant that provides a unique identity 814. Once this is collected the drug prescriber can proceed to log into the central database 818 with this information.

If the identification provided by the drug consumer meets the requirements set forth by the drug prescriber, then normal procedures can be used 816. In some embodiments the valid identification can be anything that has an address and a photograph of the person. In other embodiments the drug consumer might have some advanced identification like a sub-dermal implant with an NFC identification chip. In some embodiments the identification used with the drug prescriber must be identical to the identification used with the drug dispenser. These details will be made known to the drug consumer as the drug prescriber builds the dosage rule file at the central database.

In those embodiments a reference number like a health card number or driver's license will be recorded and will have to be matched later before the prescription will be dispensed. With a valid identification from the drug consumer 816 the drug dispenser can log into the central database and provide the ID and indicate the type of ID used 818. If the identification is a driver's license or some other physical form of identification this is indicated. If the identification is a biometric, then this is indicated. In this embodiment the central database saves this information and uses it for the next step.

Once the identification is entered an advanced search is performed 820 by the central database. This advanced search will use the drug consumer's name, their identification and their bio-identification if provided to see if there is any reason why this drug should not be prescribed to this drug consumer 820. In some cases the drug consumer might be doctor-shopping in order to get multiple prescriptions of the same drug in order to abuse the drug. If the drug consumer provides a false name and has false photo identification then there could be problems tracking down the fact that they are trying to abuse the system. In these cases the biometric method is the best method to catch them and stop their potentially abusive activities. If the drug consumer is not safe to prescribe the requested drug 822 they will be turned away 824.

If the drug consumer is not matched in the system, the drug prescriber can continue through the remaining steps to setup and configure a prescription file for the drug consumer 826. An example UI for this step is provided in FIG. 6. There are many embodiments for what a dosage rule file contains. In table 1 of this application provides some example fields for the dosage rule file, for example it could have the drug name and in some cases the manufacturer, the strength of each dose and the frequency of dosage. In other embodiments the drug prescriber can also indicate the drug-overlap so that the dispensing device can be re-filled before it is completely empty. In this embodiment the interface might default to 3 dosages and the drug prescriber can adjust that when they talk to the drug consumer 826.

Figure 9:
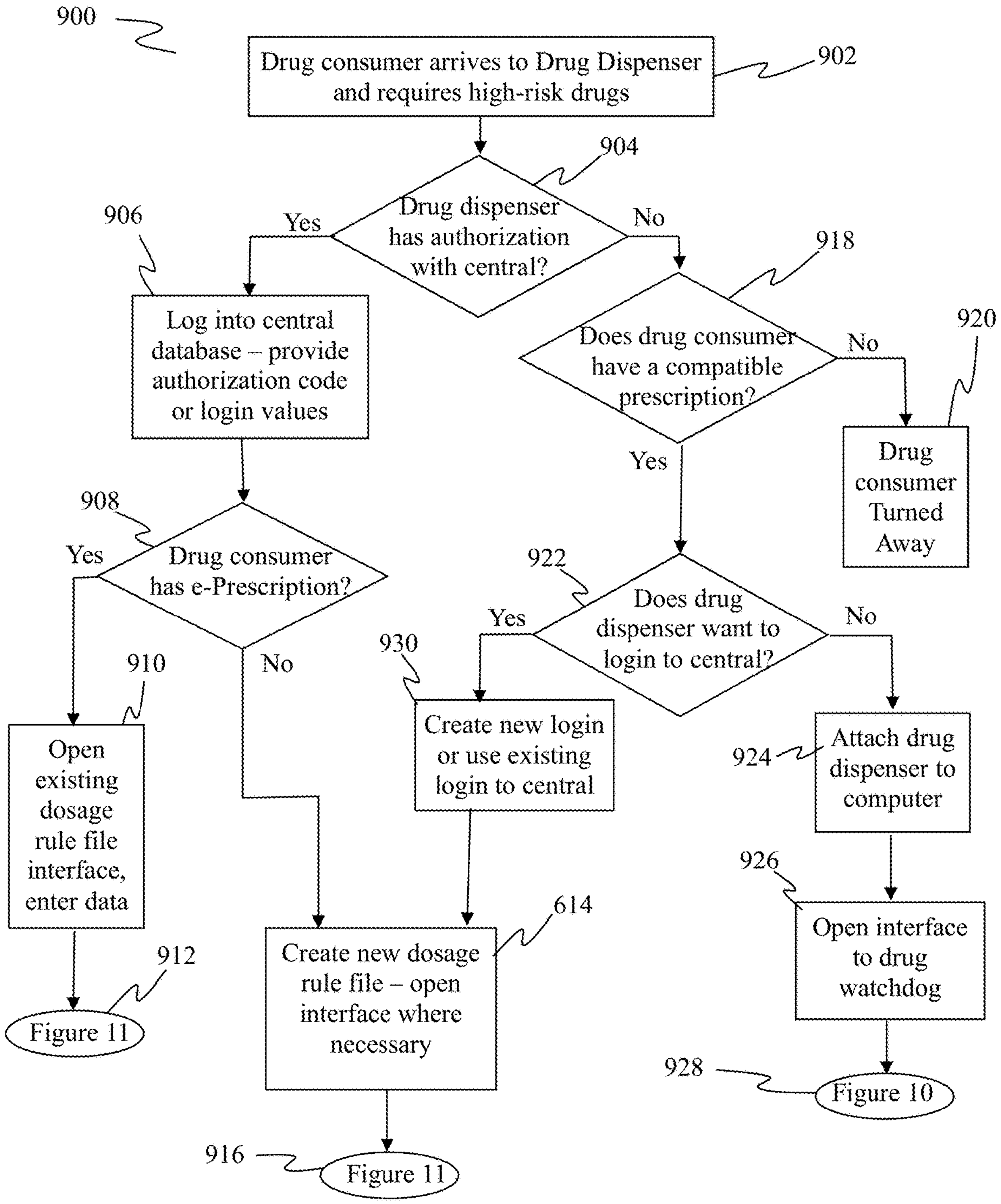
FIG. 9 is a data flow diagram of one embodiment showing the first interactions between a drug dispenser and a drug consumer.

Turning now to FIG. 9 there is a data flow diagram 900 of one embodiment showing the first interactions between a drug dispenser and a drug consumer. A drug consumer arrives at a drug dispenser's location and requests that a prescription be filled for drugs that require the use of a dispensing device 902. This could be any form of drugs and in some embodiments include high-risk and highly addictive drugs that they have been prescribed 902.

In other embodiments the drug consumer is supported by a health care professional, family member or loved one and the location is a health clinic, old age home, senior care facility, the drug consumer's home or many other possible places. The first decision to be made is to determine if the drug dispenser has an authorized login at the central database 904. They would be authorized if they have been professionally accredited by a governing body in one example. It is also possible they are using an e-prescription service and have an authorized login they can use there.

If they are already authorized, or have the ability to create that login, they can proceed to log into the central database 906 and fulfill the authorization stage of the system. They would be presented with a UI similar to the one presented in FIG. 6. They can then look at what the drug consumer hands them or tells them and decide if the drug prescriber has already started the process of creating an e-prescription 908. In some embodiments the dosage rule file 908 may be have started on the central database. In other cases, the e-prescription might have been started on a regional or national e-prescription service.

If they believe there should be a dosage rule file started at the central database or a e-prescribing service, they proceed to do the necessary work to find it 910. If an e-prescribing service has been used, then the information can be extracted using APIs and a dosage rule file can be started using this information. In these embodiments the drug dispensing might be working with a Pharmacy Management System (PSM). When a PMS is used there could be a two-step process for building the dosage rule file.

In this embodiment the drug dispenser first locates the existing e-prescription on the server and downloads the patient's prescription script. The second step is when this information is imported into the central database using various APIs, like JSON as previous discussed. This path leads to a series of additional steps on FIG. 11 912. If however the drug consumer indicates they do not have a dosage rule file or an e-prescription already started 908, then the drug dispenser will have to create a new dosage rule file 914. The drug dispenser will have to collect identification information from the drug consumer and begin to fill in the dosage rule file information 914. To perform these steps the logic leads to a series of other steps found in FIG. 1 916.

If the drug dispenser does not have authorization at the central database 904 a different set of steps are required for them. First, they must determine if the drug consumer has brought them a compatible prescription that is located on the central database 918. In this embodiment the drug prescriber has started the dosage rule file on the central database or an e-prescribing service, but the drug dispenser is unable to find it and continue building it 918. This can happen when the drug dispenser is not authorized or is relatively new and has not been added to the central database.

In other situations, perhaps in a remote community the drug dispenser does not have access to a public network like the Internet. Maybe the drug dispenser is older and very set in their ways and refuses to make the effort to create a login account for themselves at the central database. This might also happen if a health profession or family member is trying to use the dispensing device, but a real pharmacist is needed to facilitate this. In these situations the drug consumer will have to be turned away and will have to find another more advanced drug dispenser 920.

However, if the drug consumer hands them a prescription that has not been started on the central database 918, the drug dispenser can still provide a safe means to deal with this drug. The first decision the drug dispenser makes is whether they want to login to the central database 922. If they do not want to bother, they will have to attach the drug dispensing device 924. Since the dispensing device acts as an extension of the central database, it can perform the authorization stage on behalf of the central database for the drug dispenser. In some embodiments this connection could be a USB connection, in other embodiments it could be a Bluetooth connection just to name a few. In some embodiments a Bluetooth connection is useful when a cellphone is used in the authorization and provisioning stages. After connecting the dispensing device 914 they open an interface using an Internet browser or a custom-built application to the drug watchdog on the dispensing device over the connection that has been established 926. This path then leads to a series of provisioning steps in FIG. 10 928.

Otherwise if they do want to create or use an existing login on the central computer, they open an interface to the central computer 930 using an Internet browser or a dedicated, custom-built application. This leads them to the path of creating a new dosage rule file from scratch on the central database 914. This path leads to a series of steps for creating a new dosage rule file in FIG. 11 916.

Figure 10:
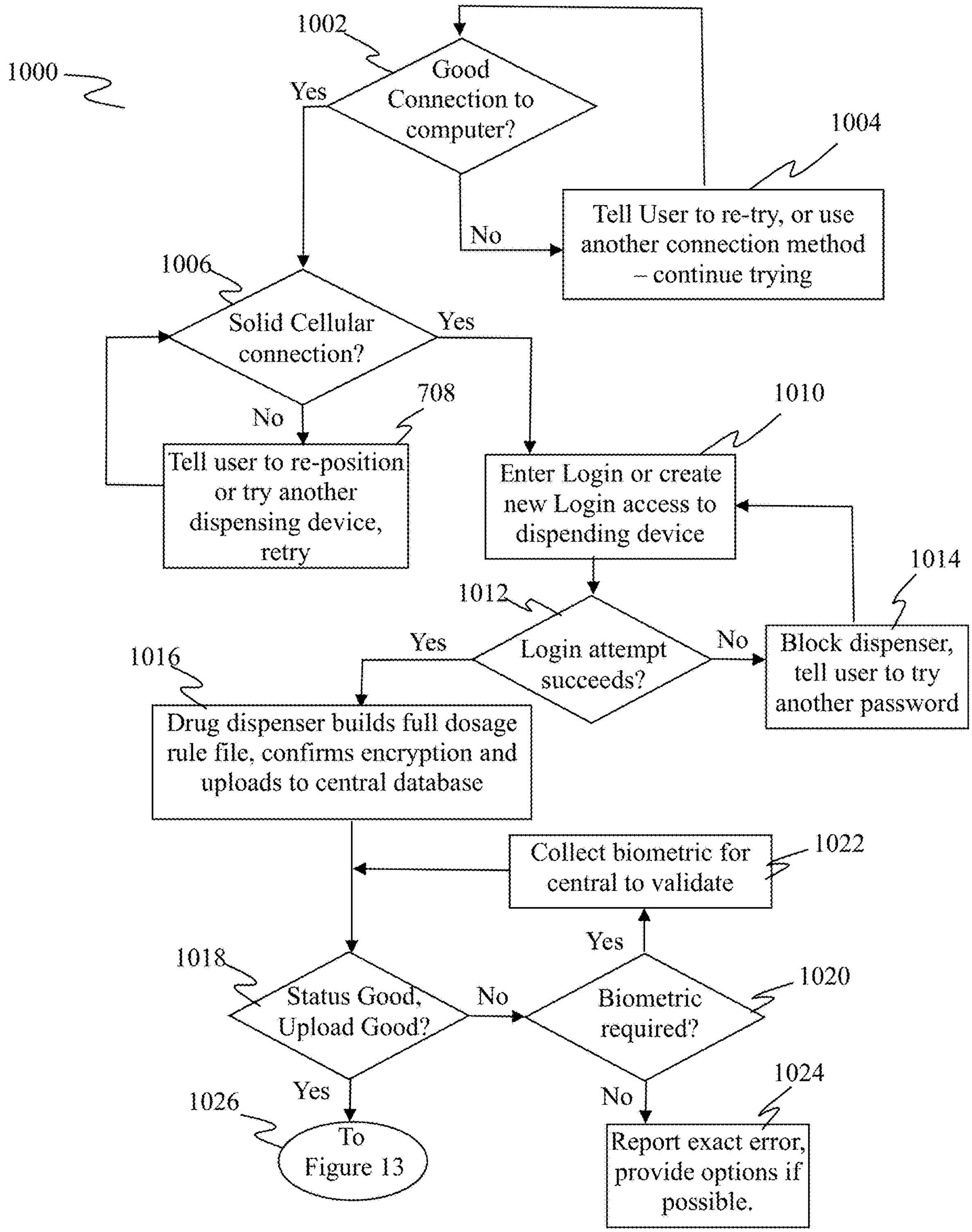
FIG. 10 is a data flow diagram of one embodiment for a drug dispenser to work directly with a dispensing device to provision a dosage rule file.

Turning now to FIG. 10 is a data flow diagram 1000 of one embodiment for a drug dispenser to work directly with a dispensing device to provision a dosage rule file. Since the drug dispenser has elected to work directly with the dispensing device, they have opened an interface over the connection established. There are several embodiments for how to view the interface, for example an Internet browser might be used and the dispensing device provides HTML compatible messages for the drug dispenser. In another embodiment a custom-built application can be used to talk to the dispensing device using a proprietary interface format. This embodiment would be more frequently used with a fully integrated dispensing device, where the drug watchdog program is running within the same physical enclosure.

Whatever interface is provided to the drug dispenser they must wait until the connection is successful. If not connected 1004 they might be given warning to try other methods or other computer links. In some embodiments if universal serial bus (USB) is used then perhaps they have plugged the dispensing device into a bad USB connection on the computer. Most computers have two or three USB ports to choose from. In other embodiments if a Bluetooth connection is used perhaps coverage is an issue or the computer doesn't support Bluetooth, or the Bluetooth pairing protocol has failed for some reason. In these embodiments it might be best for the drug dispenser to switch from Bluetooth to USB to reduce frustration. In some embodiments if a connection method is used that does not involve a physical connection like Bluetooth for example, the drug watchdog program on the dispensing device might perform a change in state on the dispensing device to challenge the user 1004. This change of state could be illuminating a unique combination of LED lights, making a sound, or displaying a set of numbers or letters on a screen. This ensures that someone who is physically close but not in control of the dispensing device. In these embodiments the change in state of the dispensing device will require confirmation on the interface that ideally cannot be seen by the person trying to hijack the dispensing device. The goal is to ensure a nefarious individual does not succeed in confusing or taking control of the login process.

This process will continue until a solid connection is detected and has been verified before the drug dispenser can proceed to the next step. Since the drug dispenser is not connected to the central database the dispensing device must rely on its cellular capabilities to create a secure link to the central database. This is where the dispensing device is acting as a proxy for the central database to create an authorization.

In many embodiments the RF cellular link could be over a wide-area wireless technology like GSM, EDGE, UTMS, 4G, 5G or future 6G type networks. In other embodiments the RF link is over a WiFi network following 802.11 protocols. In this embodiment where WiFi is used by the drug dispenser, they will have to provide their WiFi password and access codes for the dispensing device to establish its secure link.

The interface will inform the drug dispenser whether a solid cellular connection has been established or not 1006. If these attempts fail the interface will provide some guidance and suggest re-positioning the device or even in some cases trying another dispensing device 1008. If the drug dispenser can't get a reliable link they may have to abandon the effort.

Otherwise once the RF link is established the drug dispenser will be given the login screen from the drug watchdog 1010. The login screen might require them to re-enter a previously established login. In some embodiments the login might be just a password or access code. In other embodiments the login could be a login name and a login password. In other embodiments it could be a login name, login password and an answer a familiar question challenge, like where were you born 1010. If the login attempt fails 1012 then the dispensing device is blocked from them 1014. In some embodiments there could be there are drugs still inside and inappropriate attempts are being made to get into the dispensing device 1014. In some embodiments after several wrong answers the dispensing device might start to send alert messages to the central computer. The central computer might in turn send out alert emails to all health care professional associated to this dispensing device. Too many failures in entering an existing password can result in the dispensing device shutting down the interface for a period of time to discourage the password attack.

Once the old password is entered or a new password is created for a brand-new dispensing device 1012 the drug dispenser can begin the process of creating a new dosage rule file 1016. The drug dispenser goes through a series of questions and answers to fill out a table similar to the example provided in Table 1.

Once the required answers are provided the drug watchdog on the dispensing device is ready to establish or confirm their encryption key with the central database and begin exchanging messages. This includes getting status information to the central database, uploading the dosage rule file and getting status back from the central database about the dosage rule file. A review is done by the drug watchdog to ensure the upload was good and the status is good from the central database 1018.

There are several embodiments of what the status from the central database could indicate. For example, it is possible that when the drug dispenser uses this dispensing device method to distribute high-risk drugs that a biometric is required from every patient 1020. In this embodiments a biometric is taken for each and every drug consumer that wants a prescription filled for a high-risk medication 1022. In these embodiments the drug dispenser will take a biometric from everyone asking for a particular set of drugs. This biometric will then be uploaded to the central database where it will be used for an advanced search against all other biometrics in the system 1022. A further status is received and checked 1018 by the drug watchdog. If the status is still not okay and a biometric is not required 1020 then it is possible the biometric reviewed issues or some other error has taken place 1024. The drug consumer is informed, and the exact error is reported through the interface to the drug dispenser to pass along to the drug consumer 1024. Otherwise if the status is good and the upload is good the dispensing device can be provisioned, and control continues in FIG. 13 1026.

Figure 11:
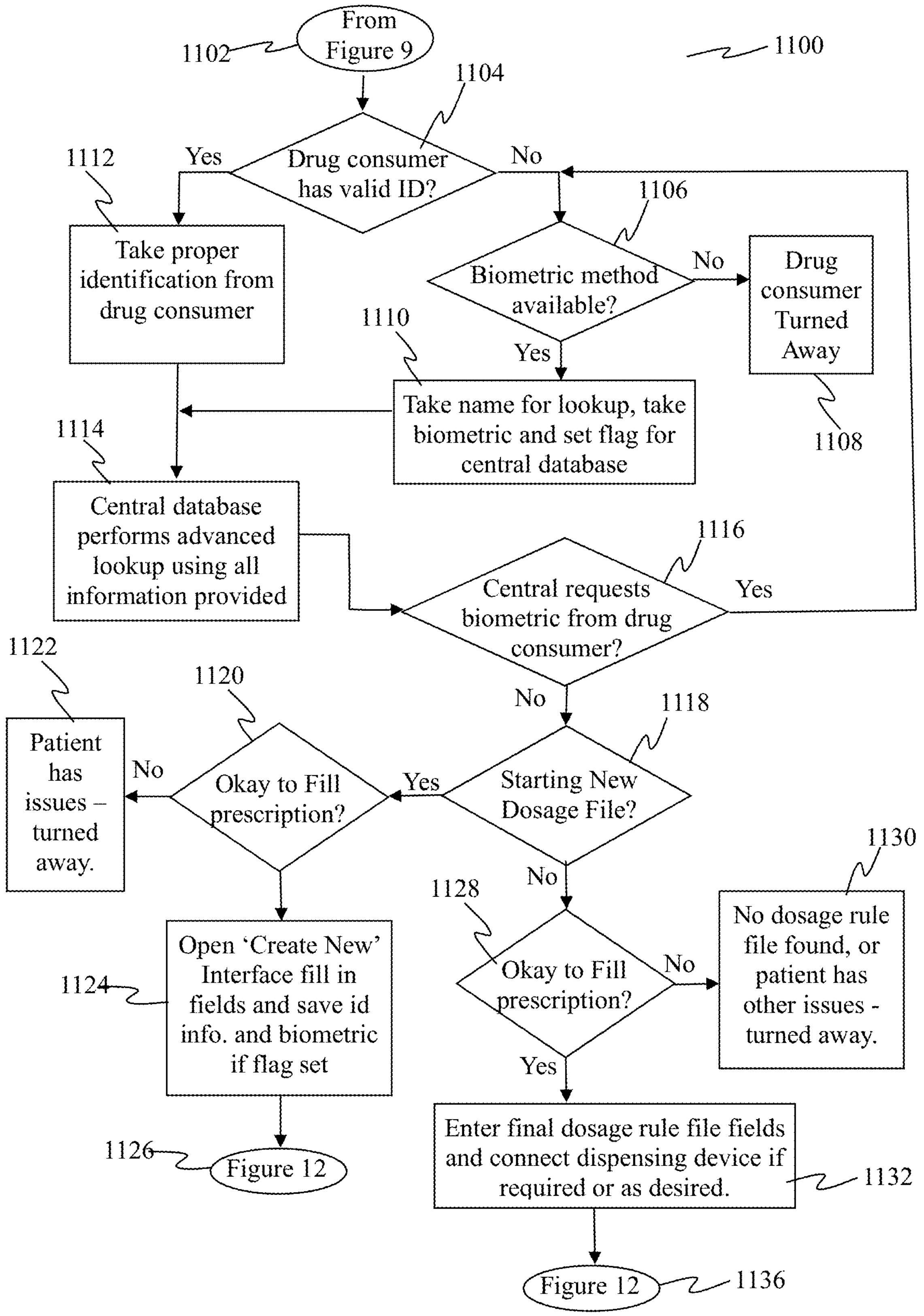
FIG. 11 is a data flow diagram of one embodiment for a drug dispenser to work with the central database to provision a dosage rule file.

Turning now to FIG. 11 there is a data flow diagram 1100 of one embodiment for a drug dispenser to work with the central database to provision a dosage rule file. Based on FIG. 6 a drug consumer has arrived at a drug dispenser's location and is asking for a drug they have been prescribed that requires the use of a dispensing device 1102. The drug dispenser is logged into the central database either through their authorized login and password or as authorized by a connected dispensing device 1102. In this later embodiment the drug dispenser may have reused a previously created login and password from previous provisioning of drug dispensers.

The drug dispenser first determines if the drug consumer has valid identification 1104. In some embodiments the biometric is always collected by the drug prescriber and in those embodiments every drug consumer is assumed to have insufficient identification or that the drug is so high-risk that it is the safest course of action. In other embodiments it might be the drug is highly sought after in the open market for the illicit drug trade so every person needing it must be protected. In this embodiment it is possible the drug consumer will have valid identification and the central database will request a biometric at a later time.

If the drug consumer does not have valid identification 1104 the drug dispenser decides if they can provide a biometric method for finding their medication 1106. In some embodiments there could be some drug dispensing locations that cannot provide this service. In some embodiments the drug consumer comes into the drug dispenser's location already knowing they need to use the biometric method and simply tell the drug dispenser they must be able to support this. If this drug dispenser cannot provide this service, the drug consumer will be turned away 1108.

Otherwise if the drug dispenser can provide this service, they will first take their name for the first stage lookup 1110. Then they will take the drug consumer's biometric from a device that is connected to their computer 1110. In some embodiments the biometric input device could be the dispensing device itself that is being used in a specialized collect and send biometric only mode. In other embodiments a specialized biometric reader is used that is fully compatible with the biometric collector used in the drug prescriber's location. With this information collected, the drug dispenser can provide this information to the central database and proceed with the necessary steps 1114. In other embodiments where the drug watchdog right be running on a drug consumer cell phone, the biometric will be collected from this device and verified.

If the drug consumer has valid identification the drug dispenser takes this information and talks to the drug consumer to ensure it is the same information provided to the drug prescriber 1112. Through the interface to the central database they can now submit the identification collected and also indicate the type of identification and whether a biometric is also present 1114. The drug dispenser then requests that an advanced search be preformed by the central database's computers to ensure the drug consumer can receive this dosage rule file 1114. With this information the central database looks through all dispensing device assignments to ensure this drug consumer is okay to receive this prescription. As discussed, in some embodiments the drug consumer is only allowed to possess one dispensing device with a given drug within it. In other embodiments the drug consumer can have two or more dispensing devices that will work in series to dispense drugs. So as one dispenser is depleted of drugs the central database sends a begin deployment command to the next dispensing device in sequence until they are all depleted.

The first feedback from the lookup checks to see if a biometric is required from the drug consumer 1116. In some embodiments the central database might be requesting a biometric from every single drug consumer wanting this particular drug. There are many other embodiments as to why the biometric must be provided. In this situation the drug dispenser must have the ability to collect the biometric 1106. If they cannot provide this service, the drug consumer is turned away 1108.

Otherwise, the biometric is collected and provided to the central database 1110. With the newly acquired biometric the central database can then perform another search with the biometric data included in the search and finally approve or not approve the drug consumer 1114.

With the biometric received and confirmed a check is performed to see if this is a new dosage file being created 1118. Coming from FIG. 6 there are logical paths where the drug dispenser was not completing an already started dosage rule file. If this is a new dosage rule file, an additional check is made on the status code returned from the advanced central database lookup 1120. If the code indicates a problem the process is terminated, and the patient does not receive their drugs and are turned away 1122. Even through the biometric was not used to find an existing dosage rule file, it might have found a drug consumer that is trying to game the system for additional doses of high-risk drugs. This embodiment and several others could occur that indicate the drug consumer is unsuitable to receive a dosage rule file, and the associated drugs, so they are turned away 1122. As discussed earlier there are situations where a drug consumer is allowed to have more than one dispensing device with the same drug in it and in other embodiments where they are not allowed to use the hot-swap method. This check will help ensure rules around using the hot-swap method are followed.

If the status code from the advanced search indicates there is no problem 1120, the drug dispenser can open the 'create new' interface and start to fill out the fields for the dosage rule file 1124. They will save the drug consumer's identification and any biometric that has been provided 1124. When all the fields are completed, the dosage rule can be downloaded which takes place following the logic in FIG. 12 1126.

If the drug dispenser is not starting a new dosage file 1118, they must have been trying to match an existing dosage rule file. Therefore, the status returned from the advanced looking from the central database is checked 1128. If the status indicates there was a problem, it could be because the dosage rule file could not be found 1130. In other situations the negative indication on the search could indicate there is another reason the drug consumer is unsuitable 1130. In some cases, between the times that a prescription is created and it is filled, the drug consumer could have already tried to abuse the system 1130. There could be other scenarios where the drug consumer is unsuitable to receive a dosage rule file, so they are turned away in these cases 1130.

If the drug consumer is okay to receive this dosage rule file, the drug dispenser can optionally connect a dispensing device to their computer 1132, if not already connected. In some embodiments the drug dispenser has already connected the dispensing device to be granted authorization to login into the central database. In other embodiments the drug dispenser has been granted access via their organizational credentials from a regulating body. In some embodiments the credentials have been granted through a national or regional e-prescribing service, like PrescribeIT™ in Canada. In these embodiments the drug dispenser will first retrieve the prescription script from the e-prescribing server into an extension to a Pharmacy Management Solution (PMS). Then they will import these values into the dosage rule file fields on the central database and complete the final fields 1132.

In other embodiments the owner of the dispensing device has possession of the device and is working with the central database directly. In these embodiments the dispensing device does not have to be connected and the central database can use the cellular link to reach it. In these embodiments the drug dispenser is required to enter the dispensing device's identification code to start a verification process that they possess the device.

The verification process for the drug dispenser involves confirming they are in possession of the dispensing device. This is performed by confirming a change of state sent from the central database to the dispensing device. This change could be the illumination of LED lights, some auditory sounds or a display of numbers and letters. Once confirmed the drug dispenser will be able to continue filling out the dosage rule file 1132 until all fields are satisfied.

Figure 12:
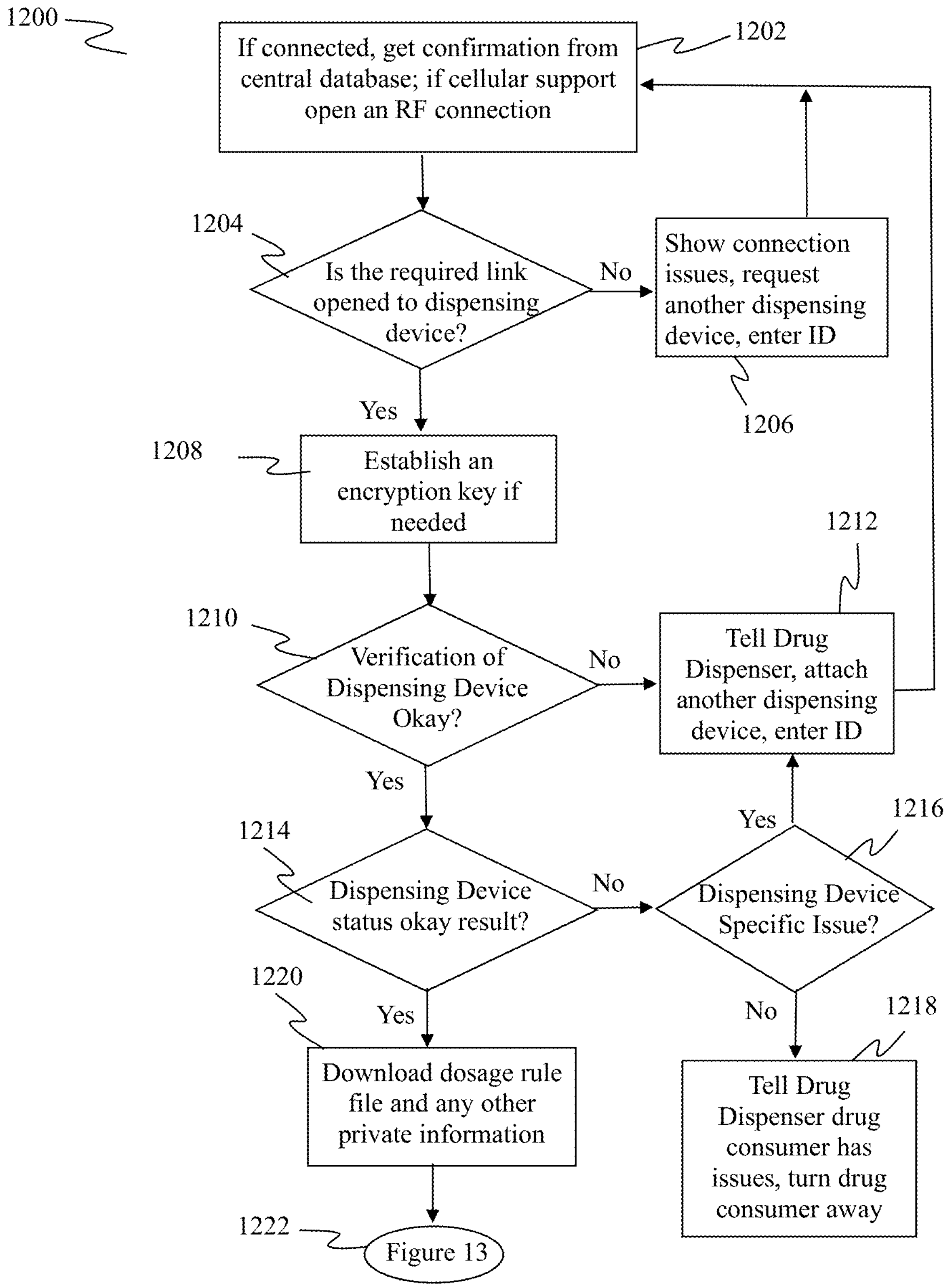
FIG. 12 is a data flow diagram of one embodiment for the process to download a created dosage rule file from a central database to a dispensing device.

With the device identified by the central database the prescription file can be downloaded to the drug watchdog program running on the identified dispensing device. FIG. 12 shows the logic involved in downloading now that the dispensing device is identified and the drug consumer is approved for the dosage rule file 1136.

Turning to FIG. 12 is a data flow diagram 1200 of one embodiment for the process to download a created dosage rule file from a central database to a dispensing device. Based on the steps from FIG. 11 the central database will do a final confirmation that a dispensing device is connected or reachable through some communication means 1202.

As mentioned in some embodiments a connection is not required to the drug dispenser's computer 1202. In some embodiments this data communication connection between the central database and the dispensing device could be facilitated by an Internet browser, an Internet browser software add-on or extension. In other embodiments a custom piece of software is used by the drug dispenser to facilitate a connection between the central database and the dispensing device.

The central database has details on each dispensing device and knows if the dispensing device supports cellular communications. If the dispensing device does support a cellular data communication link, the central database will confirm a cellular link has been made. One example UI for the drug dispenser is shown in FIG. 6. In some embodiments the drug dispenser will work with an external wand or cell phone type device that will be running the drug watchdog. In these embodiments the central database will establish a secure connection with this device after it has been properly configured to work for this given drug consumer 1204.

Once both connection methods have been checked the central database can then confirms that at least one link has been established with the drug watchdog either on the drug dispensing equipment 1204 or on a separate computer system. For example, in the embodiment where the drug dispensers is using the dispensing device as authorization for the login to the central database, it must be connected. In those embodiments where the cellular link can be used exclusively, a check is made that at least a cellular connection has been achieved 1204. In some embodiments both a connection through the drug dispenser's computer and a cellular connection could used to complement each other. In this embodiment the central database would have the discretionary choice as to which link they used based on coverage, the quality and speed of the link, security issues and other factors.

If the required link is not present, then the error is displayed to the drug dispenser over their interface 1206. The drug dispenser will be given the choice to attach another dispensing device 1206 or abandon the effort or try again. In some embodiments it could be a cellular coverage and signal issue. The drug dispenser is informed that the dispensing device cannot be reach and it is up to them to determine if coverage is an issue. In some embodiments the central database might be capable of displaying the current RF signal strength to the drug dispenser.

If they do attach another dispensing device, they enter the dispensing device Id and return to the connection step 1202. With one or both a physical connection and cellular connection created, the dispensing device can confirm it has an establish a secure communication path for data communications. In some embodiments it must create or use a pre-loaded encryption key 1208. In other embodiments a secure communications path can be established with the telecommunications network being used, for example like an SSL connection over a cellular and Internet combined connection using both a client and a server certificate.

In some embodiments a secure link is not possible, and every message will be encrypted for maximum security. In some embodiments the dispensing device was manufactured and preloaded with the necessary encryption keys from the central database. For example, using public and private cryptography every dispensing device is manufactured with a private key and the matching public key has been provided to the central database.

In other embodiments an encryption key is created using a seed value, like the dispensing device identification. Different encryption methods for creating a shared encryption key can be used with the encryption key available. Over the secure communications path the dispensing device provides its identification and its status information to the central database for verification 1210.

The verification step will look at the current status of the dispensing device and check message exchanges to confirm whether any serious error messages have been received 1210. For example, in some embodiments the dispensing device's identification could be unknown. Perhaps this is a rogue or illegal dispensing device that someone is trying to use. In some embodiments the dispensing device could have battery issues. In other embodiments the dispensing device could have software or mechanical issues and needs to be retired 1210. In this situation the drug dispenser is told to attach another dispensing device 1212 and provide the new identification to the central database. The process then returns to step 1202 to allow another dispensing device to be tried.

If the dispensing device is suitable then the central database does further checks on additional details about what has been happening during its last dosage rule file usage 1214. It might indicate an issue between the drug consumer's consumption profile with previously loaded drugs within the dispensing device itself. The dispensing device might have a deeper software issue or an issue with the drug dispenser's location. This deeper status issue could indicate the reception of one or more error messages that suggest an attempt to break into the dispensing device or that the dispensing device has been compromised in some way that isn't immediately visible 1214.

If there is a problem a further check is made to see if there is a dispensing device specific issue 1216. If there is a dispensing device specific issue, the drug dispenser is told to attach another dispensing device 1212. Another dispensing device is attached, then the identification is provided to the central database 1212 so it can go through the same process at step 1202. Otherwise if the drug consumer has been abusing the device or abusing the system and the drug dispenser is informed 1218. The drug dispenser can take the dispensing device and turn away the drug consumer 1218.

If the dispensing device's deeper status is okay, then the dosage rule file is downloaded 1220 using the communications medium best suited and chosen by the central database. Any other important and private information is also downloaded into the system at this time as well. This information could relate to operational behaviour, movement status information, behaviours to watch out for related to location and drug consumption issues. Finally, the drug dispenser is ready for final provisioning and normal operation; the process continues in FIG. 13 1222.

Figure 13:
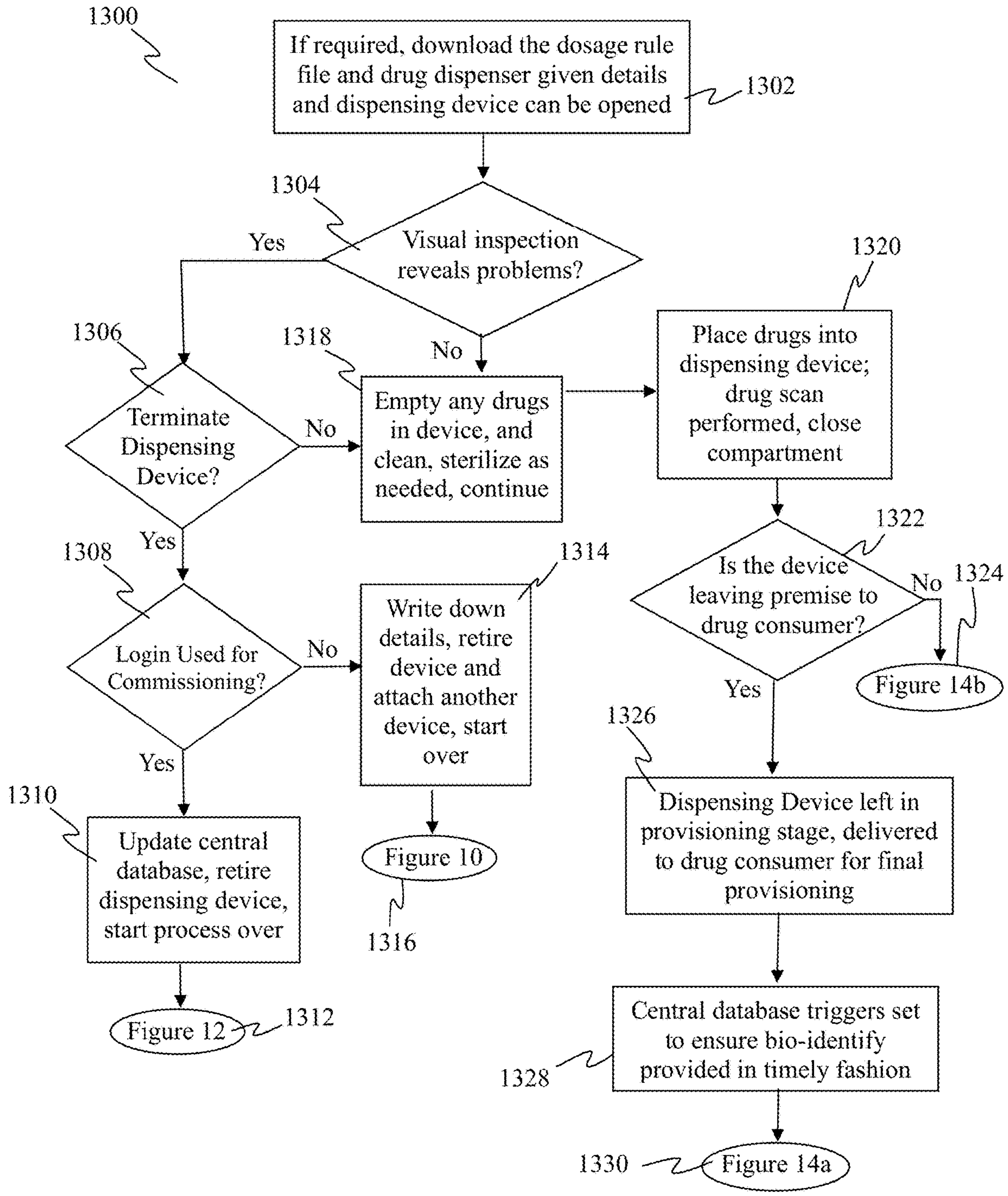
FIG. 13 is a data flow diagram of one embodiment that illustrates steps in the first steps of the provisioning stage for a dispensing device.

Turning now to FIG. 13 there is a data flow diagram 1300 of one embodiment that illustrates steps in the first steps of the provisioning stage for a dispensing device. With the dosage rule file built, either on the dispensing device direction or on the central database, it can be exchanged and verified.

In those embodiments where the dispensing device builds the dosage rule file, the provisioning stage can begin once it is uploaded, as illustrated in FIG. 10. Alternatively, the drug dispenser as built the dosage rule file on the central database and it is downloaded to the dispensing machine, can the provisioning stage start. This is illustrated in FIGS. 11 and 12.

With the central database and the dispensing device have exchanged the dosage rule file, the central database sends a command to commence the provisioning stage 1302. Additionally, the drug dispensing is given the details of the dosage rule file and if they are logged into the central database will have additional options. In some embodiments they will be given the ability to customize a printout for the drug consumer. In some embodiments they can also print out a label to affix to the dispensing device similar to a pill bottle. With the dosage rule file safely downloaded to the drug watchdog on the dispensing device the drug dispenser is given access to the dispensing device's main holding area 1302. In one embodiment the software releases an internal latch or lock and a larger door can be opened. In another embodiment a specialized key can be used to unlock the dispensing device to load in the drugs at this time.

With the dispensing device open the drug dispenser can look into the dispensing device to see if there are any visual problems 1304. There are many possible expected and unexpected issues that could be seen once the dispensing device is open 1306. The drug dispenser decides if the dispensing device should be terminated and retired 1306. In one embodiment the dispensing device might have gotten wet or it has been submerged in water for a period of time, for example caught in the rain. There is also a chance mould or mildew has developed in the device, or the mechanism appears broken. If these obvious major problems are not seen, then it is possible the dispensing device is not empty; this could be expected or unexpected. If it is expected the drug dispenser might be simply topping-up the number of drugs in the dispensing device 1318.

In other situations it might be unexpected to find drugs in the main compartment 1318. In this case the drug might have to be removed and returned to the manufacturer for destruction. In some embodiments the dispensing device must be cleaned, which could involve sterilization or wiping the unit with a sterile implement. In these embodiments each dispensing device must be physically sterilized before new drugs can be inserted into the device. In some embodiments a disposable piece that had previous held drugs is thrown out and a new drug holding component is added to keep each load of drugs from cross-contaminating each other.

With the unit cleaned, sterilized and ready for loading, the drugs are removed or topped-up within the dispensing device and the main compartment is closed 1320. There are several ways drugs could be inserted into the device. In some embodiments each drug is encoded with a bar code, a Q-code or some form of indicator. Each time a drug is inserted into the device the bar code is read and is confirmed against the expected drug indicated in the dosage rule file.

In other embodiments the drugs are inserted into a separate container that confirms the types of drugs inserted before being placed into the larger dispensing device. In some embodiments to facilitate a sterile environment, each drug is separately wrapped in some form of removable covering which is also bar coded in some fashion. In some embodiments a low-frequency RFID tag could also be included that would be detected and read by the dispensing device once inserted. As each pill is placed into the dispensing device the covering is scanned to confirm the drug matches exactly what is listed in the dosage rule file.

Alternatively, if the dispensing device has a serious problem and the user has logged into the central database 1308 then can update the central database about this broken unit, retire the dispensing device and start the process over 1310. Since the drug dispensing is logged onto the central database, they can enter the details into the central database's interface 1310. In some embodiments there could be a pick-list of choices to help narrow down the specific issue the drug dispenser is seeing. In other embodiments the drug dispenser will simply decide about whether the dispensing device or drug consumer is the source of the problem. This will mean returning to FIG. 11 and connecting a new device 1312. If the drug dispenser is not logged into the central database they can create an authorized login directly through the dispensing device. They can write-down the number of the dispensing device that has the serious problem, retire the device and connect another dispensing device 1314. In this case they must start over on FIG. 10 1316.

If there are no visual inspection problems revealed 1304, then the drug dispenser can proceed to place the prescribed drugs into the dispensing device 1320. Once the dispensing device has receive the correct amount of drugs, the larger door on the dispensing device is closed and the unit is ready for performing the final provisioning step.

The last step in provisioning of the dispensing device requires the drug consumer to provide their bio-identity with the dispensing device. In some embodiments, this can be a one-step process that collects the biometric information for confirming every drug dose to be taken. In other embodiments, it involves a biometric and a biomedical input. There are several embodiments that are possible with the dispensing device once it is loaded with drugs. The first step is to determine if the dispensing device is leaving the premise to reach the drug consumer 1322. If it is not leaving this implies the drug consumer is present and can provide their bio-identity. In this case the data flow moves to FIG. **14*a* 1324**.

In some embodiments the dispensing device will be delivered by bonded courier, drug delivery agent or hand-carried in some fashion to the drug consumer 1326. This could be an elderly patient, it could be a person who is extremely sick, it could be someone who is self-isolating due to a communicable disease or a worry about spreading a pandemic virus. Whatever the case, the dispensing device has no issues with staying in a partially completed provisioning stage waiting for the bio-identity input 1326.

To ensure that there is no mis-step in collecting the bio-identity the central database sets a trigger to ensure the bio-identity is provided in a timely fashion 1328. The trigger could be a timer causes a notification email message to be sent to the drug dispenser, or it could result in an SMS message being sent to a drug dispenser's cell phone. With the trigger set, the data flow moves to FIG. **14*b* 1330**.

Figure 14:
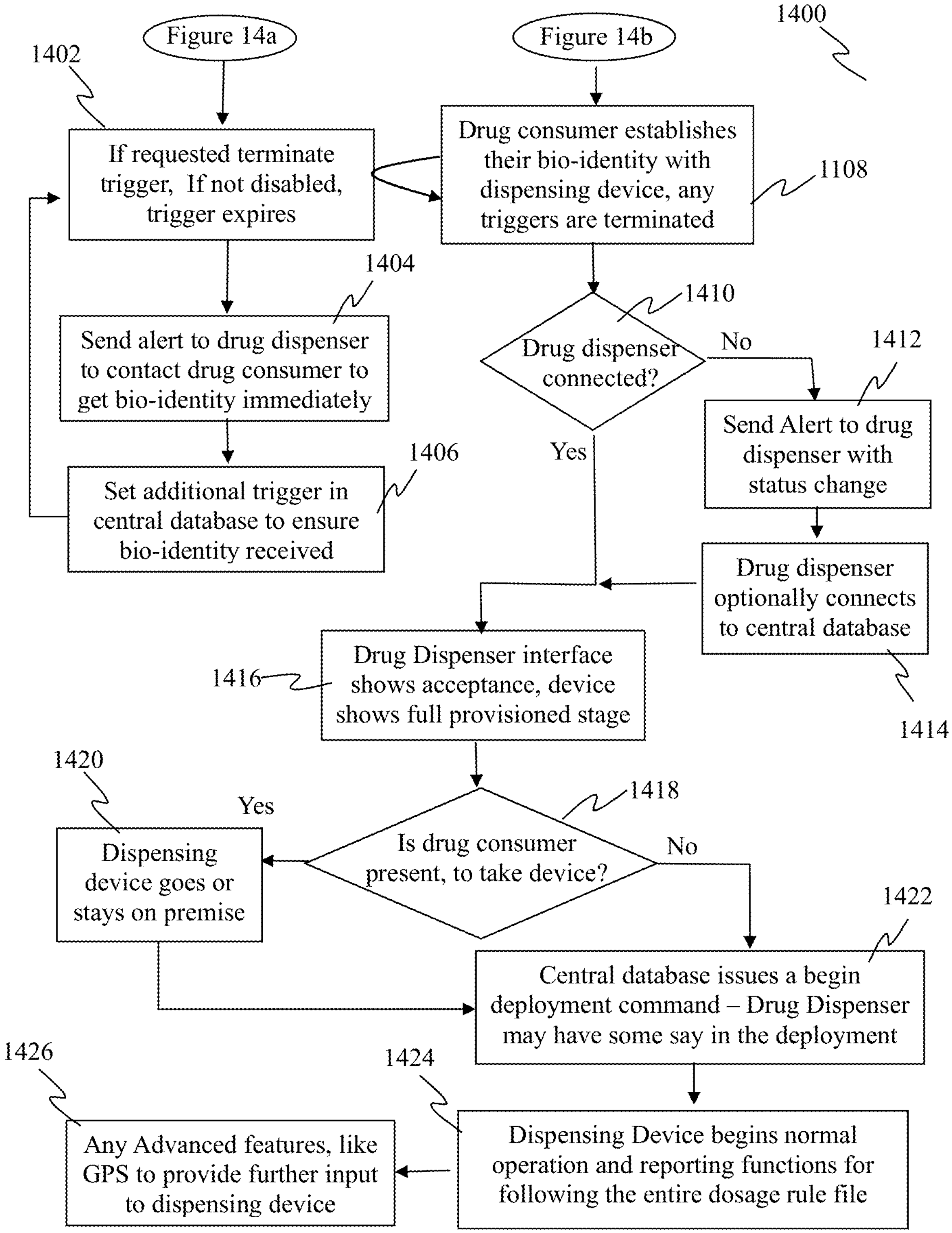
FIG. 14 is a data flow diagram of one embodiment that illustrates steps for finishing provisioning and entering the deployment phase for a dispensing device.

Turning now to FIG. 14 there is a data flow diagram 1400 of one embodiment that illustrates steps for finishing provisioning and entering the deployment phase for a dispensing device. Data flow from FIG. 13 arrives into FIG. 14 in two forms. First in action labelled FIG. **14*a*, there have been triggers set within the central database and they could either be terminated because a bio-identity has been received, or they have expired 1402. If they have expired, perhaps several hours or a day has passed, an alert is sent to the drug dispenser 1404. The drug dispenser is encouraged to contact the drug consumer and they are reminded to provide a bio-identity 1404. If they are an elderly patient, perhaps the drug dispenser provides them with guidance on how to perform this action 1404. Then an additional trigger is set in the central database to ensure the bio-identity is received 1406**.

Second in action labelled FIG. **14*b* the drug consumer establishes their bio-identity with the dispensing device 1408. This is detected at the central database as the dispensing device sends a message indicating it has entered full provisioned stage 1408. In this case any triggers are terminated related to this dispensing device 1408**. If the drug consumer was physically present beside the drug dispenser it is likely no triggers had to be set and so they were not needed.

When collecting the biometric part of the bio-identity there are several embodiments. In some embodiments, part of this step may have already been performed when a biometric was collected from the drug consumer. In other embodiments the biometric has been downloaded with the dosage rule file from the dispensing device when it is provided to the drug prescriber. However, in this step the bio-identity goes directly into the memory of the dispensing device for daily use each time the drug consumer wishes to extract another dose of drugs.

In some embodiments the dispensing device might also encrypt this biometric to ensure it is not compromised, stolen or damaged in some way. In other embodiments the biometric will use a secure enclave method for storing and matching the biometric. The enclave method turns the biometric, like a fingerprint or heart rhythm into an algorithm that is uploaded into the dispensing device or created by the dispensing device. In this embodiment the biometric itself is not stored on the dispensing device, just an algorithm that is created by the biometric. When this algorithm is executed with input from a newly acquired biometric it produces a match or no match answer. This is a method that can be used by smartphones and small devices with limited computing resources and a high need for security.

The provisioning of the full bio-identity may include one or more steps involving biomedical data collection and upload to the central database. The drug dispensing might have to collect blood analysis results, urinalysis results, EKG, EEG, saliva testing results, photographic identification and a wide range of combinations of these inputs. In an example the drug consumer can use a urine test strip and take a photograph and upload this to the central database. The data can act as a baseline for further photographs to see the effects of the drugs on the drug consumer's body. Further embodiments of this biometrical step have been described earlier in this patent.

In some embodiments the bio-identity is then shared with the central database and the drug dispenser's interface shows acceptance of the bio-identity 1416. In other embodiments the bio-identify is maintained only on the dispensing device and a confirmation message that provisioning steps are complete is sent. This message then shows that the dispensing device 1416. In some embodiments the interface will allow one or two additional trial runs of the bio-identity to ensure it is working consistently.

With the successfully provisioning of the bio-identity the dispensing device has completed the provisioning steps and enters full provisioned stage. When this is communicated to the central database it allows the central database to decide when to begin the deployment stage. In some embodiments this happens immediately after the provisioned stage is reached. For example, if the drug consumer has only one dispensing device with this drug assigned to them the central database can decided to auto-deploy immediately. In other embodiments the drug dispenser would like control over when deployment takes place even with only one dispensing device deployed. For example, if the dispensing device must be couriered to the drug consumer's home.

With the bio-identity received a check is made to see if the drug dispenser is connected via the UI to the central database 1410. If the drug dispenser is actively working with a drug consumer in the same physical space, they might still be sitting at their screen watching all the final steps to confirm everything is flowing smoothly 1410. If they had the dispensing device delivered however they are probably not connected. In this case an alert is sent to the drug dispenser to indicate the status change in a dispensing device that has now been fully provisioned 1412. The drug dispenser can then optionally connect to the central database to ensure the dispensing device enters deployment stage correctly 1414. Naturally over time the drug dispenser will trust the operation of the central database as it follows specific logic and knows precisely when to deploy one or more dispensing devices when sent to the same patient using the hot-swap, continuous drug supply method.

If the drug dispenser connects display the status change to the interface 1416. Another logic is made to confirm whether the drug consumer is present beside the drug dispenser in their office 1418. If they are present the drug dispenser can decide whether they are allowed to take the dispensing device home or not 1420. Depending on the situation, the drug dispenser must decide if it is reasonable for the drug consumer to take the dispensing device home 1420. In some embodiments the drug consumer is homeless or untrustworthy and so the dispensing device will have to stay on the premise of the drug dispenser 1420. In other embodiments the dispensing device can be taken home by the drug consumer 1420.

When the central database receives the fully provisioned message from the dispensing device there are several embodiments as to how and when the dispensing device is commanded to enter the deployment stage 1422. In one embodiment the central database will auto-deploy the dispensing device. This could happen if this is the only or first dispensing device given to a drug consumer. Since there are no other dispensing devices it is safe for this dispensing device to start operating immediately 1422.

In another embodiment the drug dispenser might want to have some say in when the begin deployment command is sent 1422. In some central database design options there could be an override to allow the drug dispenser to decide when deployment starts 1422. This might be useful for a high-risk drug consumer or someone that is a flight risk.

In another embodiment the drug dispenser has little to no control over deployment but can issue a stop deployment to an earlier dispensing device in the field 1422. This might be necessary if a first dispensing device is exhibiting issues and problems and must be stopped. Once the first dispensing device has received the stop deployment the second dispensing device will be sent a begin deployment command. In situations where multiple dispensing devices have been given to the same drug consumer with the same drug it is the central database that tracks precisely when to issue the begin deployment command 1422. It will only allow one dispensing device to be in active deployment at a given time. Only when the currently deployed dispensing device runs out of drugs will the next dispensing device be deployed 1422.

After receiving a begin deployment command, the dispensing device is in the deployment stage and begins its normal course of operation 1424. It follows the guidelines of the dosage rule file and allows the single dose drug dispenser to open every time the prescription indicates a dose is allowed and the biometric input is provided 1424. In some embodiments when cellular support is present in the dispensing device, messages will be sent providing full tracking information to the central database. There are many embodiments for the type of tracking information available to the central database and it will be closely related to the functionality of the dispensing device.

In some embodiments there can be messages indicating when drugs were extracted by the drug consumer, related to when they were allowed. In some embodiments where the dispensing device supports GPS 1426, there could be information about the location of the device and where it travels. In some embodiments there could be warning or alert messages if the drug consumer misses their dosage for more than a specified length of time past the dosage time. There could also be messages indicating that forced entry has been attempted or achieved on the dispensing device.

In some embodiments the dispensing device might offer a physical display for the drug consumer. In other embodiments the dispensing device might have a set of LED lights 1426 or auditable output options 1426. In other embodiments one or more messages can be sent to the drug consumer using configured information to inform them of the state change within the dispensing device.

These and other embodiments are possible for the dispensing device depending on the goals of the solution. In some embodiments biomedical data must be collected during the deployment phase of the dispensing device. In these embodiments further advanced functions for the dispensing device are possible 1426. In some embodiments the drug consumer has a wearable device to monitor drug consumption. This could be a watch, ring, bracelet, band around the stomach or a belt device capable of picking up a signal when a drug has been consumed and digested. The use of specialized chemical compounds to achieve such drug consumption monitoring are already in use as was discussed earlier. In some embodiments, input through USB, Bluetooth, NFC or some other communications method allows the dispensing device to receive heart rate results, blood testing analysis, urinalysis results or other biomedical data. There could also be embodiments involving GPS coordinates and providing location information back to the central database 1426.

In other embodiments there is a camera that can take a photograph or video of the drug consumer when they take the pill from the extraction area. There are embodiments where a combination of steps are needed to fulfill the biomedical requirements during the deployment phase. For example, the drug consumer might have to photograph urine test strips that have been dipped and show the results of the consumed drugs taken. These photographs must then be uploaded to the dispensing device or the central database directly for a health care professional to review and approve the continued use of the drug. These and many other embodiments could enhance the operation of the dispensing device 1426.

Different methods and systems are described to provide different example configurations. The methods are computer implemented methods using hardware processors, secure communication channels, and non-transitory memory.

In an aspect, embodiments can provide a method of creating, modifying, executing and tracking a dosage rule file between a central database and a drug watchdog program running on a dispensing device. The method can involve, at a central database, authorizing a login by matching credentials of the user against a database of authorized users and receiving dispensing device identification for the dispensing device; modifying or creating a dosage rule file based on input from the authorized user, the dosage rule file encoding at least drug consumption information, identification of the drug consumer, and additional authorized users for this dispensing device; identifying a destination dispensing device to receive the dosage rule file by a processing that accesses the dispensing device identification provided by the authorized login; establishing a secure communication link to encrypt messages exchanged with the dispensing device with encryption keys to confirm the identification information of the dispensing device; downloading, using the secure link, the dosage rule file to provision of the dispensing device, executing the dosage rule file to configure the drug watchdog program to: open a compartment of the dispensing device to receive drugs matching the drug consumption information in the dosage rule file; detect the closure of the compartment to indicate the drug provisioning of the dispensing device; successfully provision a bio-identity input and send a provisioned stage reached message to the central database to program the processor to a provisioned stage; receive a begin deployment command from the central database to program the processor to a deployment stage of the dispensing device; activate timers upon deployment on the dispensing device to control release of the drugs contained in the compartment for the drug consumer; encrypt messages using the encryption keys; send the encrypted drug consumption messages for viewing by all authorized users to the central database upon expiration of at least one of the timers.

In an aspect, embodiments can provide a method of creating, modifying, executing and tracking a dosage rule file between a central database and a drug watchdog program running on a dispensing device. The method can involve at a central database, authorizing a login by matching the credentials of the user against a database of authorized users and receiving dispensing device identification; generating a dosage rule file encoding at least identification of a drug consumer, drug consumption information and additional authorized users for this dispensing device; identifying a destination dispensing device to receive the dosage rule file through the dispensing device identification provided by the authorized login; establishing an encrypted communication channel with the dispensing device to confirm the identity of the dispensing device; downloading, using the encryption communications channel, the dosage rule file to enable provisioning of the dispensing device; executing the dosage rule file to configure the drug watchdog program to: open a compartment of the dispensing device to allow drugs to be inserted matching the drug consumption information in the dosage rule file; detect the closure of the compartment to indicate the drug provisioning of the dispensing device; successfully provision a bio-identity input from drug consumer and send a confirmation message to enter a provisioned stage; receive a begin deployment command that commences the deployment stage of the dispensing device; activate timers upon deployment on the dispensing device to allow the controlled release of the drugs contained in the compartment for the drug consumer; and send drug consumption messages for viewing by all authorized users, using the encrypted communication channel, to the central database upon expiration of at least one of the timers.

In an aspect, embodiments can provide a method of creating, modifying, executing and tracking a dosage rule file between a central database and a drug watchdog program running on a dispensing device. The method involves, at a central database, creating an authorized user by verifying a dispensing device coupled to the user's computer and generating a login communication session; generating a completed dosage rule file containing at least identification of a drug consumer, drug consumption information and additional authorized users for this dispensing device; identifying a destination dispensing device to receive the completed dosage rule file using dispensing device identification provided by using the login communication session; using the dispensing device identification to select encryption keys to be used to encrypt messages exchanged with the dispensing device; downloading, using the selected encryption keys, the dosage rule file to enable the provisioning of dispensing device; executing the dosage rule file to configure the drug watchdog program to: open a compartment of the dispensing equipment to allow drugs to be inserted matching the drug consumption information in the dosage rule file; detect the closure of the compartment to indicate the drug provisioning of the dispensing device; successfully provision a bio-identity input from drug consumer and sending a confirmation message to the central database to enter a provisioned stage of the dispensing device; receive a begin deployment command from the central database that commences the deployment stage of the dispensing device; activate timers upon deployment on the dispensing device to allow the controlled release of the drugs contained in the compartment for the drug consumer; and send drug consumption messages for viewing by all authorized users, using the selected encryption keys, to the central database upon expiration of the timer.

In an aspect, embodiments can provide a method of creating, modifying, executing and tracking a dosage rule file between a central database and a drug watchdog program running on a dispensing device. The method involves: at dispensing device with a drug watchdog program, detecting a connection from a selected dispensing device to a user's computer system; permitting a login by the user to create an authorized drug dispenser; providing an interface through the connection to receive input from the authorized drug dispenser to generate a completed dosage rule file, containing at least the drug consumer's identity, drug consumption information and additional authorized users for this dispensing device, on the connected dispensing device; initiating a separate connection to the central database when the authorized drug dispenser has finished the completed dosage file; using the separate connection to provide the selected dispensing device's identification in order to select encryption keys to be used to encrypt messages exchanged between the dispensing device and the central database; exchanging the completed dosage rule file with the central database to enable the provisioning of the dispensing device; executing the dosage rule file to configure the drug watchdog program to: open a compartment of the dispensing device to allow drugs to be inserted matching the drug consumption information in the dosage rule file; detect the closure of the compartment to indicate the drug provisioning of the dispensing device; successfully provision a bio-identity input from drug consumer and sending a confirmation message to the central database to enter a provisioned stage of the dispensing device; receive a begin deployment command from the central database that commences the deployment stage of the dispensing device; activate timers upon deployment on the dispensing device to allow the controlled release of the drugs contained in the compartment; and send drug consumption messages for viewing by all authorized users, using the selected encryption keys to the central database when the timer expires.

In an aspect, embodiments can provide a method of creating, modifying, executing and tracking a dosage rule file between a central database and a drug watchdog program running on a dispensing device. The method involves: at a drug watchdog program, detecting a connection from a selected dispensing device to a user's computer system; authorizing the user as an authorized drug dispenser, by accepting a login at a central database upon confirmation of the identification information of the connected dispensing device; providing, to the authorized drug dispenser, an interface on the central computer in order to generate a completed dosage rule file containing at least the drug consumer's identity, drug consumption information and additional authorized users for this dispensing device; detecting the finishing of the completed dosage rule file and using the selected dispensing device's identification received from the dispensing device through its connection to the user's computer, to create an secure channel to encrypt all messages exchanged between the dispensing device and the central database; exchanging the completed dosage rule file with the central database to enable the provisioning of the dispensing device; executing the dosage rule file to configure the drug watchdog program to: open a compartment of the dispensing device to allow drugs to be inserted matching the drug consumption information in the dosage rule file; detect the closure of the compartment to indicate the drug provisioning of the dispensing device; successfully provision a bio-identity input from drug consumer and sending a confirmation message to the central database to enter a provisioned stage of the dispensing device; receive a begin deployment command from the central database that commences the deployment stage of the dispensing device; activate timers upon deployment on the dispensing device to allow the controlled release of the drugs contained in the compartment; and send drug consumption messages for viewing by all authorized users, using the selected encryption keys to the central database when the timer expires.

In an aspect, embodiments can provide a method of creating, modifying, executing and tracking a dosage rule file between a central database and a drug watchdog program running on a dispensing device. The method involves: at a drug watchdog program, establishing a secure cellular data communication path with a central database by using the dispensing device's identification to select encryption keys; receiving an indication from the central database over the secure communication path that a completed dosage rule file, containing at least the drug consumer's identity, drug consumption information and additional authorized users for this dispensing device, is ready for download, the completed dosage rule file encrypted using encryption keys linked to the dispensing device identification; verifying that at least one authorized user is in possession of the identified dispensing device by changing the state of the dispensing device and requiring the authorized user to verify that state; exchanging the completed dosage rule file with the central database when the authorized user is verified, to enable the provisioning of the dispensing device; at the dispensing device, executing the dosage rule file to configure the drug watchdog program to: open a compartment of the dispensing device to allow drugs to be inserted matching the drug consumption information in the dosage rule file; detect the closure of the compartment to indicate the drug provisioning of the dispensing device; successfully provision a bio-identity input from drug consumer and sending a confirmation message to the central database to end a provisioned stage of the dispensing device; receive a begin deployment command from the central database that commences the deployment stage of the dispensing device; activate timers upon deployment on the dispensing device to allow the controlled release of the drugs contained in the compartment; and send drug consumption messages and alert messages for viewing by all authorized users, using the selected encryption keys to the central database when the timer expires.

In an aspect, embodiments can provide a method of creating, modifying, executing and tracking a dosage rule file by an authorized drug dispenser using one or more databases and a drug watchdog program running on a dispensing device. The method involves: authorizing a login by matching the credentials of the user against a prescription database of authorized users to create an authorized drug dispenser; searching by the authorized drug dispenser for prescription information on a prescription database linked to a drug consumer's identity; creating a dosage rule file from the prescription information that can be downloaded to the dispensing device; establishing a secure data communication path between a central database used for managing dispensing devices, by using identification of the dispensing device to select encryption keys; exchanging with the central database over the secure communication path the dosage rule file storing at least the drug consumer's identity, drug consumption information and additional authorized users for the dispensing device, the dosage rule file encrypted using encryption keys linked to the dispensing device identification; executing the dosage rule file to configure the drug watchdog program to: open a compartment of the dispensing device to allow drugs to be inserted matching the drug consumption information in the dosage rule file; detect the closure of the compartment to indicate the drug provisioning of the dispensing device; successfully provision a bio-identity input from the drug consumer and sending a confirmation message to the central database to enter a provisioned stage; receive a begin deployment command from the central database that commences the deployment stage; activate timers upon deployment on the dispensing device to allow the controlled release of the drugs contained in the compartment; and send drug consumption messages and alert messages for viewing by all authorized users, using the selected encryption keys to the central database when the timer expires.

In some embodiments, the change of state involves the illumination of LED lights on the dispensing device following a pattern sent from the central database. In some embodiments, the change of state involves the display of a series of letters, numbers or symbols on a display provided by the dispensing device following a pattern sent from the central database.

In some embodiments, the prescription database is a e-prescribing service established for a national registry of patient prescription services.

In some embodiments, the completing of the steps to create a dosage rule file involves moving the prescription information from the prescription database to the central database that is used for managing dispensing devices.

In some embodiments, the provisioning of a bio-identity involves the use of a biometric input that is also used during the deployment phase to confirm the drug consumer's identity for the removal of the regular dose of drug following the guidelines in the dosage rule file.

In some embodiments, the provisioning of the bio-identity involves the input of one or more biomedical inputs selected from any of blood analysis results, urinalysis results, heart rate information, EKG information, EEG information, saliva analysis results, photographic images of the drug consumer and photographic images of analysis results.

In some embodiments, the provisioning of biomedical information to enter the deployment stage is repeated at various configured intervals during the deployment phase to ensure the continued dispensing of regular drug doses.

In some embodiments, during the deployment stage additional biomedical input is required at various configured stages to ensure the continued dispensing of regular drug doses. Biomedical inputs can include one or more of blood analysis results, urinalysis results, heart rate information, EKG information, EEG information, saliva analysis results, photographic images of the drug consumer, photographic images of analysis results and drug consumption feedback from drug digestion monitors.

In some embodiments, the creating of the dosage rule file allows the definition of additional authorized users to access information exchanged with the chosen dispensing device.

In some embodiments, the accessing of information exchanged by all authorized users further includes the ability for one or more of the authorized users to modify the dosage rule file.

In some embodiments, the dosage rule file changes it will be downloaded to the dispensing device to replace the existing dosage rule file, leading to an updated execution of the dosage rule file by the drug watchdog program.

In some embodiments, the change of state involves the playing of a series of sounds on the dispensing device following a pattern sent from the central database.

In some embodiments, activation of timers to allow the release of drugs also includes the addition of auditory sounds when drug dose timers expire.

In some embodiments, the opening of the compartment requires a confirming status message from the central database informing the drug watchdog to perform an unlock procedure.

In some embodiments, the expiration of the activated drug dose timers to allow the release of a drug dose, also includes one or more indications including modifying the display of LED lights, displaying a message on a screen, the playing of auditory sounds and the sending one or more message to the drug consumer using a configured communication method.

In some embodiments, an alert message from the dispensing device going to the central database can also be relayed from the central database to the drug consumer using one or more configured communication methods. In some embodiments, an alert message within the dispensing device can be sent directly to the drug consumer's computer device using one or more configured communication methods.

In some embodiments, the insertion of drugs matching the drug consumption information takes places using a drug detection means that identifies each drug that is inserted into the dispensing device.

In some embodiments, receiving biometric input to the dispensing device to confirm removal of the drugs. In some embodiments, detecting a connection to a user's computer system involves receiving and completing a Universal Serial Bus (USB) handshaking protocol. In some embodiments, detecting a connection to a user's computer system involves receiving and completing the Bluetooth pairing protocol. In some embodiments, the opening of the compartment requires a confirming status message from the central database inform the drug watchdog to perform an unlock procedure.

In some embodiments, the viewing of messages by all authorized users further includes the ability for one of the authorized users to modify the dosage rule file.

In some embodiments, activation of timers to allow the release of drugs also includes the addition of auditory sounds when drug dose timers expire. In some embodiments, activation of timers to allow the release of drugs also includes LED light illuminations when drug dose timers expire. In some embodiments, the central database allows multiple dispensing devices to be in a provisioned stage and sends a begin deployment command to only one dispensing device assigned to the same drug consumer at a time.

In some embodiments, when the central database detects that a deployed dispensing device has run out of drugs it sends a begin deployment command to the next provisioned dispensing device for the same drug consumer.

In an aspect, embodiments can provide a system for creating, modifying, executing and tracking a dosage rule file. The system can involve a central database to generate and provide a completed dosage rule file, containing at least a drug consumer's identity, drug consumption information and authorized users for a dispensing device, the completed dosage rule file encrypted using encryption keys linked to the dispensing device identification; a drug watchdog program running on the dispensing device, the drug watchdog program having instructions to: establish a secure cellular data communication path with the central database by using the dispensing device's identification to create an encrypted channel; verify that at least one authorized user is in possession of the identified dispensing device by changing the state of the dispensing device and requiring the authorized user to verify that state; receive an indication from the central database within the received status message over the secure communication path that the completed dosage rule file is ready for download after the authorized user is verified; exchange the completed dosage rule file with the central database to enable the provisioning of the dispensing device; wherein the completed dosage rule file executes to: open a compartment of the dispensing device to allow drugs to be inserted matching the drug consumption information in the dosage rule file; detect the closure of the compartment to indicate the drug provisioning of the dispensing device; successfully provision a biometric input from drug consumer and sending a confirmation message to the central database to enter a provisioned stage of the dispensing device; receive a begin deployment command from the central database that commences the deployment stage of the dispensing device; activate timers upon deployment on the dispensing device to allow the controlled release of the drugs contained in the compartment; and send drug consumption messages for viewing by all authorized users, using the selected encryption keys to the central database when the timer expires.

In some embodiments, the change of state involves the illumination of LED lights on the dispensing device following a pattern sent from the central database.

In some embodiments, the change of state involves the playing of a series of sounds on the dispensing device following a pattern sent from the central database.

In some embodiments, the change of state involves the display of a series of letters, numbers or symbols on a display provided by the dispensing device following a pattern sent from the central database.

In some embodiments, the drug watchdog program receives biometric input at the dispensing device to confirm removal of the drugs.

In some embodiments, the drug watchdog program detects a connection to a user's computer system by receiving and completing a Universal Serial Bus (USB) handshaking protocol. In some embodiments, the drug watchdog program detects a connection to a user's computer system involves receiving and completing the Bluetooth pairing protocol. In some embodiments, the completed dosage rule file executes to detect the opening of the compartment by receiving a confirming status message from the central database to perform an unlock procedure. In some embodiments, the messages provides for the ability for one of the authorized users to modify the dosage rule file. In some embodiments, the dosage rule file changes it will be downloaded to the dispensing device to replace the existing dosage rule file.

In some embodiments, activation of timers to allow the release of drugs also includes the addition of auditory sounds when drug dose timers expire. In some embodiments, activation of timers to allow the release of drugs also includes LED light illuminations when drug dose timers expire. In some embodiments, the insertion of drugs matching the drug consumption information takes places using a drug detection means that identifies each drug that is inserted into the dispensing device.

In an aspect, embodiments can provide a method of controlling and tracking a dosage rule file between a central database and a drug watchdog program running on a dispensing device. The method can involve, at a central database, authorizing a login by verifying user login data; creating a dosage rule file containing at least drug consumption information and additional authorized users for this dispensing device; displaying tracking information from the dispensing device for the additional authorized users; initiating a secure link between the central database and the drug watchdog program by creating and using a shared encryption key; downloading, over the secure link, the dosage rule file and other messages related to operation of the dispensing device; executing the dosage rule file to configure the drug watchdog program to: open a compartment of the dispensing device using a lock to allow drugs to be inserted into the main compartment; detect the closure of the compartment using the lock and allowing a controlled release of the drugs contained in the compartment; and send feedback messages to the central database of activities detected on the dispensing device.

In an aspect, embodiments can provide a method of controlling and tracking a dosage rule file between a central database and a drug watchdog program running on a dispensing device. The method involves: at a drug watchdog program, detecting a connection to a drug dispenser's computer; verifying a login by a drug dispenser's to permit access to the dispensing device; using an interface to generate a dosage rule file; initiating a secure link between the drug watchdog program and the central database by creating and using a shared encryption key; uploading to the central database over the secure link the dosage rule file and other messages related to operation of the dispensing device; executing the dosage rule file to configure the drug watchdog program to: open a compartment of the dispensing device using a lock to allow drugs to be inserted into the main compartment; detect the closure of the compartment through the lock and allowing release of the drugs contained in the compartment using an ejector; and send feedback messages to the central database of activities detected on the dispensing device.

In some embodiments, authorizing the login involves authenticating using a connection to an authenticated dispensing device.

In some embodiments, authorizing the login involves matching login information to data received from one or more governing body of professionals and government organizations.

In some embodiments, the drug consumption information includes the number of drugs to be inserted into the dispensing device.

In some embodiments, an additional authorized user can also have the dosage rule file updated and downloaded to the dispensing device.

In an aspect, embodiments can provide a method of controlling and tracking a dispensing device for delivery of prescription drugs for a drug consumer using a dosage rule file for configuring a drug watchdog program to control the dispensing device. The method involves: generating a login procedure to establish an authorized drug prescriber and an authorized drug dispenser by matching credentials for authorized drug prescriber and the authorized drug dispenser to data encoding drug prescribers and drug dispensers; generating the dosage rule file for the drug consumer containing at least drug consumption information based on input from an authorized drug prescriber and identification information received from a drug consumer; receiving a request from an authorized drug dispenser to match a drug consumer's identification information to the identification information in the dosage rule file; authenticating at a central database an attached dispensing device with one or more messages exchanged with a drug watchdog program running within the dispensing device; downloading, using one or more of the messages, the dosage rule file to the dispensing device for use by the drug watchdog program; executing the dosage rule file to configure the drug watchdog program to: block all attempts by other programs running on the dispensing device to perform file commands on the dosage rule file; use the drug consumption information within the dosage rule file to time the release of drugs contained within the dispensing device through a drug ejector; and provide feedback messages of all activities that take place at the dispensing device to the central database.

In some embodiments, the authorized drug prescriber and the authorized drug dispenser use a biometric input as part of creating a login procedure at the central database.

In some embodiments, the taking identification includes using biometric information from the drug consumer. In some embodiments, the drug dispenser matches the drug consumer's information by taking biometric information from them. In some embodiments, the authenticating of the dispensing device takes place by sending a manufactured serial number when exchanging one or more messages.

In some embodiments, the authenticating of the dispensing device takes place using public and private encryption keys that were pre-loaded during the manufacturing process.

In some embodiments, the authenticating of the dispensing device also requires a physical connection to a computer within the drug dispenser's location.

In some embodiments, the authenticated dispensing device also requires the creation of a separate encryption key that is used for all data exchanges with the central database.

In some embodiments, the authenticating of an attached dispensing device can also include the ability to detect the type and number of drugs within the drug dispensing device to ensure ample supply is present for the next dose.

In some embodiments, the authenticating of an attached dispensing device can also include the ability to detect that there should be ample drugs still available inside the device and refusing to allow more drugs to be added.

In some embodiments, the feedback can also include detection of unauthorized activity upon the file or damage to the file to allow for re-acquisition of the file if needed.

In some embodiments, the feedback can also include detection of unauthorized attempts to access the contents of the dispensing device.

In some embodiments, the restricting of access on the prescription file also includes the ability to update the dosage rule file should an authorized change be needed to the original dosage rule file.

In some embodiments, the feedback also includes providing GPS location information when a change is detected.

In some embodiments, the feedback also includes detecting a missed dosage and sending GPS coordinates.

In some embodiments, the feedback also includes photographic information taken each time a single dose of drugs are ejected for the drug consumer.

In some embodiments, the feedback also includes ingestion information when a signal is received based on ingestion of the drug dosage within the stomach of a drug consumer.

In some embodiments, the ingestion information comes from a device that is worn on the body of the drug consumer.

In some embodiments, the signal is generated by two or more compounds that when mixed with stomach acids generate a detectable signal from within the drug consumer's stomach. In some embodiments, the one or more messages and feedback message are transmitted over a cellular network. In some embodiments, the one or more messages and feedback messages are transmitted using a WiFi communication method. In some embodiments, the one or more messages and feedback messages are transmitted using a Bluetooth communication method. In some embodiments, the one or more messages and feedback messages are transmitted using a USB connection.

In an aspect, embodiments can provide a method of using a dosage rule file to configure a drug watchdog program on a drug dispensing device and a central database to track and control the use of prescription drugs. The method can involve: authorizing a drug prescriber and a drug dispenser at a central database through a secure login procedure; permitting the authorized drug prescriber to create a dosage rule file containing drug consumption requirements on the central database; requiring an authorized drug prescriber to acquire an identity for a drug consumer and associating the identity to the dosage rule file within the central database; permitting an authorized drug dispenser to search for the dosage rule file with the identity provided by the drug consumer; sending search match results from the central database to an authorized drug dispenser confirming that the dosage rule file was located for the drug consumer; opening a data communications connection between the dispensing device and the central database; securely downloading the authorized dosage rule file into the dispensing device using one or more messages; allowing the authorized drug dispenser to access a drug containment area within the dispensing device to receive the prescribed drugs; and using the drug consumption information within the authorized dosage rule file to guide the dispensing device in permitting drugs to be dispensed for the matching drug consumer.

In an aspect, embodiments can provide a method of using a drug watchdog program working within a dispensing device to control and regulate the use of prescription drugs comprising the steps of: within the dispensing device: detecting a connection to a computer system that is located within a drug dispenser's facility; opening a connection to a central database to establish an encryption key for creating a secure communication path; receiving confirmation over the secure connection path that an authorized dosage rule file containing operating parameters will be downloaded for use by the drug watchdog program; permitting access to a main containment area to allow the drug dispenser to place a quantity of drugs to be consumed; detecting the closing of the main containment area and locking the main containment area to stop any further access to the main containment area; using the operating parameters within the authorized dosage rule file by the drug watchdog program to control the dispensing device, wherein the dosage rule file configures the drug watchdog program to stop all file access attempts by other programs on the authorized dosage rule file; use the operating parameters within the authorized dosage rule file to time the release of drugs contained within the dispensing device; send secure messages to a central database regarding all activities that are detected by dispensing device.

In an aspect, embodiments can provide a method of controlling and tracking a dispensing device for delivery of prescription drugs by an authorized drug dispenser using a dispensing device. The method involves: connecting a dispensing device to a drug dispenser's computer; establishing an authorized drug dispenser by exchanging credentials with the dispensing device to create an authorizing login procedure; generating, by the authorized drug dispenser, a dosage rule file for a drug consumer containing at least drug consumption information and the quantity of drugs to be placed into the dispensing device based on information provided by the drug prescriber; receiving identification information from the drug consumer by the authorized drug dispenser to include within the dosage rule file; provisioning the dispensing device by securely downloading the dosage rule file by the authorized drug dispenser to a drug watchdog program running on the dispensing device; wherein the dosage rule file configures the drug watchdog program to: only open the main compartment by an authorized drug dispenser performing the authorizing login procedure, allow drugs matching the amount of drugs indicated in the dosage rule file into main compartment of the dispensing device; closing the main compartment to a locked position to indicate drug provisioning of the dispensing device; provision a bio-identity input from drug consumer and sending a confirmation message to the central database to enter a provisioned stage of the dispensing device; receive a begin deployment command from the central database that commences the deployment stage of the dispensing device; use the drug consumption information within the dosage rule file upon deployment stage, to time the release of drugs contained within the dispensing device; detect any attempts to break into the dispensing device and report messages on the detection to a central database, and provide feedback messages of all activities that take place at the dispensing device to the central database.

In some embodiments, the taking identification from the drug consumer includes using biometric information from the drug consumer.

In some embodiments, the dosage rule file also contains biometric information from the drug consumer.

In some embodiments, the time release of drugs also requires a biometric input from the drug consumer.

In some embodiments, a failsafe procedure is provided to the drug consumer to release one or more additional dosages of drugs should a failure be detected when attempting to dispense a drug at the appointed time release period.

In some embodiments, the taking identification from the drug consumer includes using biometric information from the drug consumer. In some embodiments, the dosage rule file also contains biometric information from the drug consumer. In some embodiments, the time release of drugs also requires a biometric input from the drug consumer.

In some embodiments, a failsafe procedure is provided to the drug consumer to release one or more additional dosages of drugs should a failure be detected when attempting to dispense a drug at the appointed time release period.

In some embodiments, biometric input can be one or more of fingerprint detection, facial recognition, retina scan, voice matching and deep vein matching.

In an aspect, embodiments can provide a method of using a drug watchdog program working within a dispensing device to control and track the use of drugs, the method involving: at a dispensing device: detecting an authorized connection to a computer system using one or more approved connection methods; authorizing access over the approved connection to a drug dispenser using their credentials to create an authorizing login procedure; permitting access to a main containment area to allow the authorized drug dispenser to place a quantity of drugs to be consumed; accepting the download of a dosage rule file that contains at least the timed dosage requirements and the amount of drugs to be placed within the main containment area; detecting the closing of the main containment area and locking it to stop any further access; using the operating parameters within the dosage rule file by the drug watchdog program to guide the daily operation; executing the dosage rule file to configure the drug watchdog program to: stop all file access attempts by other programs on the dosage rule file; use the operating parameters within the authorized dosage rule file to time the release of drugs contained within the dispensing device; send secure messages to a central database regarding all activities that are detected, and only open the main compartment when the authorizing login procedure is successfully executed.

Different example system architectures and configurations are described for different embodiments.

The invention claimed is:

1. A computer implemented method for creating a drug authorization and control center using a mobile device, dispensing equipment and a central server, the method comprising:

at the central server, receiving an identification code and dispensing equipment identification from a drug watchdog program running on a mobile device;

using the identification code and the dispensing equipment identification to verify and associate a drug consumer to the dispensing equipment;

sending, to the drug watchdog program, a dosage rule file corresponding to the drug consumer based on the identification code to confirm the validity of the identification code;

receiving drug consumption messages;

at the dispensing equipment, sending the dispensing equipment identification and the drug consumption messages to the mobile device using a close-proximity communication method;

at the mobile device, downloading the drug watchdog program to create a drug authorization and control center;

inputting the identification code into an interface to associate the drug authorization and control center to a drug consumer;

sending the dispensing equipment identification to verify and associate the dispensing equipment to the drug consumer;

receiving the dosage rule file from the central server to guide the use of the dispensing equipment, and sending the drug consumption messages to the central server upon receiving the drug consumption messages from the dispensing equipment.

2. The method of claim 1 wherein the dosage rule file contains the drug consumer's identity for verification by the mobile device.

3. The method of claim 1 receiving, at an interface of the central server, drug consumer identification, personal information, drug regimen information and authorized user information.

4. The method of claim 1 further comprising generating, at the central server, the identification code and providing the identification code to the mobile device.

5. The method of claim 1 further comprising using, at the central server, an integration with a remote system for inputting drug consumer and medication information.

6. The method of claim 1 further comprising associating one or more dispensing equipment to a drug consumer.

7. The method of claim 1 further comprising receiving, at the dispensing equipment, remote control commands to allow access to the drugs held within a compartment of the dispensing equipment.

8. The method of claim 1 further comprising determining drug consumption activity with a scanning method using QR-code, barcode or RFID.

9. The method of claim 1 wherein the close-proximity communication method comprises one or more of USB, Bluetooth or secure NFC.

10. The method of claim 1 wherein the association of the dispensing equipment to the identified drug consumer verifies that one of several previously assigned dispensing equipment is being used by the drug consumer.

11. The method of claim 1 wherein inputting the identification code into an interface to associate the drug authorization and control center to a drug consumer comprises encoding a new relationship between the dispensing equipment and the drug consumer.

12. A computer implemented system for creating a drug authorization and control center, the system comprising:

a mobile device running a drug watchdog program;

dispensing equipment configured to send dispensing equipment identification and drug consumption messages to the mobile device using a close-proximity communication method;

non-transitory memory configured with a database;

a central server configured to:

store the dispensing equipment identification and an identification code in the database;

receive the identification code and the dispensing equipment identification from the drug watchdog program running on the mobile device;

use the identification code and the dispensing equipment identification to verify and associate a drug consumer to the dispensing equipment;

send, to the drug watchdog program running on the mobile device, a dosage rule file corresponding to the drug consumer based on the identification code to confirm the validity of the identification code;

receive the drug consumption messages from the mobile device;

wherein the mobile device is configured to:

download the drug watchdog program to create a drug authorization and control center;

input the identification code into an interface to associate the drug authorization and control center to the drug consumer;

send the dispensing equipment identification to verify and associate the dispensing equipment to the drug consumer;

receive the dosage rule file from the central server to guide the use of the identified dispensing equipment; and send the drug consumption messages to the central server upon receiving the drug consumption messages received from the dispensing equipment.

13. The system of claim 12 wherein the dosage rule file contains the drug consumer's identity for verification by the mobile device.

14. The system of claim 12 wherein the central server has an interface for inputting drug consumer identification, personal information, drug regimen information and authorized user information.

15. The system of claim 12 wherein the central server generates the identification code and provides the identification code to the mobile device.

16. The system of claim 12 wherein the central server uses an integration with a remote system for inputting drug consumer and medication information.

17. The system of claim 12 wherein one or more dispensing equipment can be associated to a drug consumer.

18. The system of claim 12 wherein the system implements a scanning method using QR-code, barcode or RFID to determine drug consumption activity.

19. The system of claim 12 wherein the close-proximity communication method comprises one or more of USB, Bluetooth or secure NFC.

20. A computer implemented method for remotely controlling dispensing equipment, the method comprising:

at a central server, storing the dispensing equipment identification and a drug consumer identity in the database;

receiving an identification code and the dispensing equipment identification from a drug watchdog program running on a mobile device;

sending a dosage rule file corresponding to the drug consumer based on the identification code to the drug watchdog program to confirm the validity of the identification code;

receiving drug consumption messages;

at dispensing equipment, receiving control commands related to drug consumption events;

sending the dispensing equipment identification and the drug consumption messages to the mobile device using the close-proximity communication method;

at the mobile device, downloading the drug watchdog program to create a drug authorization and control center;

inputting the identification code into the interface to associate the drug authorization and control center to identify the drug consumer;

receiving the dispensing equipment identification to verify that the dispensing equipment identification is assigned to the identified drug consumer;

receiving the dosage rule file from the central server to guide the use of the identified dispensing equipment; and sending the drug consumption messages to the central server upon receiving the drug consumption messages received from the dispensing equipment.

* * * * *